(12) United States Patent
Yin et al.

(10) Patent No.: US 11,091,476 B2
(45) Date of Patent: Aug. 17, 2021

(54) PROTEIN KINASE INHIBITORS, PREPARATION METHOD AND MEDICAL USE THEREOF

(71) Applicant: Gan & Lee Pharmaceuticals, Beijing (CN)

(72) Inventors: Lei Yin, Beijing (CN); Wenjian Liu, Beijing (CN); Heng Li, Beijing (CN); Dianxi Zhu, Beijing (CN)

(73) Assignee: Gan & Lee Pharmaceuticals, Beijing ( * ) Notice: Subject to any disclaimer, the term of this patent is extended or adjusted under 35 U.S.C. 154(b) by 359 days.

(21) Appl. No.: 15/778,812

(22) PCT Filed: Nov. 28, 2016

(86) PCT No.: PCT/CN2016/107455
§ 371 (c)(1),
(2) Date: May 24, 2018

(87) PCT Pub. No.: WO2018/092635
PCT Pub. Date: Jun. 8, 2017

(65) Prior Publication Data
US 2020/0165239 A1    May 28, 2020

Related U.S. Application Data

(63) Continuation of application No. PCT/CN2016/107455, filed on Nov. 28, 2016.

(30) Foreign Application Priority Data

Nov. 30, 2015 (CN) .......................... 201510856641.1

(51) Int. Cl.
| C07D 471/04 | (2006.01) |
| A61P 35/00 | (2006.01) |
| C07D 401/14 | (2006.01) |
| A61K 45/06 | (2006.01) |

(52) U.S. Cl.
CPC ............ *C07D 471/04* (2013.01); *A61P 35/00* (2018.01); *C07D 401/14* (2013.01); *A61K 45/06* (2013.01); *C07B 2200/05* (2013.01)

(58) Field of Classification Search
CPC .. C07D 401/14; C07D 471/04; A61K 31/506; A61P 35/00; A61P 35/02; A61P 31/18; A61P 9/10; A61P 9/00
USPC .......................................... 514/275; 544/331
See application file for complete search history.

(56) References Cited

U.S. PATENT DOCUMENTS

| 2009/0318484 A1 | 12/2009 | Arzeno et al. |
| 2010/0160340 A1 | 6/2010 | Coates et al. |
| 2013/0018041 A1 | 1/2013 | Bhamidipati et al. |

FOREIGN PATENT DOCUMENTS

| CN | 102007124 A | 8/2005 |
| CN | 102264725 A | 11/2011 |
| CN | 106608879 A | 5/2017 |
| EP | 3385262 A1 | 10/2018 |
| JP | 2009-525337 A | 7/2009 |
| RU | 2504545 C2 | 1/2014 |
| WO | 9811095 A1 | 3/1998 |
| WO | 03062236 A1 | 7/2003 |

(Continued)

OTHER PUBLICATIONS

Hulikal, Deuterium Labeled Compounds in Drug Discovery Process, Abstract, 2010.*

(Continued)

*Primary Examiner* — Deepak R Rao
(74) *Attorney, Agent, or Firm* — TraskBritt

(57) ABSTRACT

The embodiments disclosed herein provide compounds as shown in formula I or a tautomer, a mesomer, a racemate, an enantiomer, a diastereomer, a deuterated compound, a prodrug or a mixture thereof, or a pharmaceutically acceptable salt or solvate of the compounds as shown in formula I or a tautomer, a mesomer, a racemate, an enantiomer, a diastereomer, a deuterated compound, a prodrug or a mixture thereof, wherein $R_1$ to $R_7$ are as defined in the description. This application also provides a preparation method and a medical use of the compounds. The compounds of this disclosure have an activity superior or equivalent to the candidate drug LY2835219 currently under phase III clinical trial, and some of the compounds exhibit better selectivity. Moreover, the preferred compounds exhibit good absorption and good blood-brain distribution when administered orally. The compounds of this disclosure thus show promise for development into novel drugs for the treatment of diseases associated with cell proliferation, particularly brain tumors, providing new options for clinicians and patients.

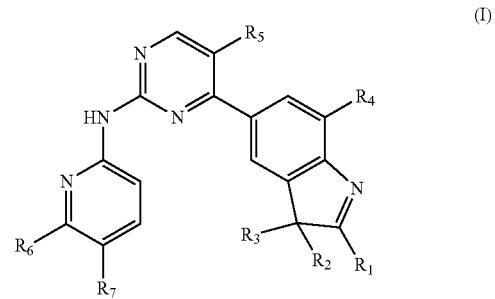

29 Claims, No Drawings

(56) References Cited

FOREIGN PATENT DOCUMENTS

| WO | 2005076854 A2 | 8/2005 |
|---|---|---|
| WO | 2007/089768 A2 | 8/2007 |
| WO | 2008/124085 A2 | 10/2008 |
| WO | 2009/017838 A2 | 2/2009 |
| WO | 2010075074 A1 | 7/2010 |
| WO | 2013173506 A3 | 4/2011 |
| WO | 2011101409 A1 | 8/2011 |
| WO | 2014/063068 A1 | 4/2014 |

OTHER PUBLICATIONS

Pimlott, PubMed Abstract (Nucl Med Commun., 26(3):183-8), 2005.*
Bundgaard, Design of Prodrugs, p. 1, 1985.*
Silverman, Prodrugs and Drug Delivery Systems, The Organic Chemistry of Drug Design and Drug Action, pp. 352-399, 1992.*
Banker et al., Prodrugs, Modern Pharmaceutics, Third Edition, Revised and Expanded, pp. 451 and 596 (1996).*
Wolff, Some consideration for prodrug design, Burger's Medicinal Chemistry and Drug Discovery, 5th Edition, vol. 1: Principles and Practice, pp. 975-977, 1995.*
Huang et al., Synthesis and biological study of 2-amino-4-aryl-5-chloropyrimidine analogues as inhibitors of VEGFR-2 and cyclin dependent kinase 1 (CDK1), Bioorganic & Medicinal Chemistry Letters, 17(8), pp. 2179-2183, (2007).*
Pearce et al., Failure modes in anticancer drug discovery and development, Cancer Drug Design and Discovery Edited by Stephen Neidle, Chapter 18, pp. 424-435 (2008).*
Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Acute Leukemia, Merck Manual (Online Edition) 6 pages, pp. 1-6 (2013).*
Fry et al., Specific Inhibition of Cyclin-Dependent Kinase 4/6 by PD 0332991 and Associated Anitumor Activity in Human Tumor Xenografts, Molecular Cancer Therapeutics, vol. 3, No. 11, (2004), 27 pages.
Gelbert et al., Preclinical characterization of the CDK4/6 inhibitor LY2835219: in-vivo cell cycle-dependent/independent anti-tumor activities alone/in combination with gemcitabine, Invest New Drugs, vol. 32, (2014), 21 pages.
International Search Report for International Application No. PCT/CN2016/107455 dated Mar. 1, 2017, 4 pages.
International Written Opinion for International Application No. PCT/CN2016/107455 dated Mar. 1, 2017, 5 pages.
Ma, Ke, Research Advances of Cyclin-Dependent Kinase4/6 Inhibitors in Anticancer, World Notices on Antibiotics, Issue 5, (2013), pp. 197-202, abstract only.
Malumbres et al., To Cycle or Not to Cycle: A Critical Decision in Cancer, Naature Reviews Cancer, vol. 3, (2001), 10 pages.

Shapiro, Geoffrey I., Cyclin-Dependent Kinase Pathways as Targets for Cancer Treatment, Jounal of Clinical Oncology, vol. 24, No. 11, (2006), abstract only.
European Communication pursuant to Article 94(3) EPC for European Application No. 16869945, dated Aug. 6, 2020, 5 pages.
European Search Report and Written Opinion from European Application No. 16869945, dated May 17, 2019, 5 pages.
Szentirmai, M.D. et al., "Noninvasive Bioluminescence Imaging of Luciferase Expressing Intracranial U87 Xenografts: Correlation With Magnetic Resonance Imaging Determined Tumor Volume and Longitudinal Use in Assessing Tumor Growth and Antiangiogenic Treatment Effect", Neurosurgery, vol. 58, No. 2 (Feb. 2006) pp. 365-372.
Australian Examination Report from Australian Application No. 2016365366, dated Apr. 17, 2020, 5 pages.
Australian Examination Report from Australian Application No. 2016365366, dated Dec. 16, 2020, 4 pages.
Brazilian Search Report and Office Action from Brazilian Application No. 112018010879, dated Jan. 11, 2021, 9 pages.
Chinese Office Action and Search Report from Chinese Application No. 201680064053, dated Jun. 5, 2020, 17 pages.
Colombian Office Action from Colombian Application No. 2018005854, dated Jan. 22, 2020, 18 pages.
Columbian Notice of Opposition from Columbian Application No. 2018005854, notified on Jun. 1, 2020, 30 pages.
Columbian Notice of Resolution from Columbian Application No. 2018005854, dated Dec. 7, 2020, 18 pages.
Columbian Office Action from Columbian Application No. 2018005854, dated Jun. 29, 2020, 23 pages.
Indian Office Action from Indian Application No. 201827020474, dated Feb. 19, 2020, 6 pages.
Indonesian Office Action from Indonesian Application No. P00201804616, 3 pages.
Israeli Office Action from Israeli Application No. 259711, dated Jan. 29, 2020, 5 pages.
Japanese Office Action from Japanese Application No. 2018-546737, dated Jun. 22, 2020, 9 pages.
Mexican Office Action from Mexican Application No. 2018006370, dated Aug. 7, 2020, 12 pages.
Mexican Office Action from Mexican Application No. 2018006370, dated Nov. 30, 2020, 14 pages.
Moroccan Decision from Moroccan Application No. 42341, dated Dec. 27, 2019, 2 pages.
Moroccan Office Action from Moroccan Application No. 42341, dated Dec. 18, 2019, 3 pages.
Moroccan Office Action from Moroccan Application No. 42341, dated Jun. 4, 2018, 8 pages.
Russian Office Action from Russian Application No. 2018122864, dated Mar. 17, 2020, 18 pages.
Russian Office Action from Russian Application No. 2018122864, dated Oct. 11, 2020, 22 pages.
Russian Search Report from Russian Application No. 2018122864, dated Mar. 11, 2020, 2 pages.
Thai Office Action from Thai Application No. 0706/2001-012557, 3 pages.
Ukrainian Office Action from Ukrainian Application No. 26996/3A/20, dated Jan. 12, 2020, 12 pages.

* cited by examiner

PROTEIN KINASE INHIBITORS, PREPARATION METHOD AND MEDICAL USE THEREOF

CROSS-REFERENCE TO RELATED APPLICATIONS

This application is a national phase entry under 35 U.S.C. § 371 of International Patent Application PCT/CN2016/107455, filed Nov. 28, 2016, designating the United States of America and published as International Patent Publication WO 2017/092635 A1 on Jun. 8, 2017, which claims the benefit under Article 8 of the Patent Cooperation Treaty to Chinese Patent Application Serial No. 201510856641.1, filed on Nov. 30, 2015, the disclosure of each of which is hereby incorporated herein in its entirety by this reference.

TECHNICAL FIELD

This application relates to the field of medicine, and particularly relates to a series of substituted 2-(pyridin-2-yl) aminopyrimidines having the activity of inhibiting protein kinase, and preparation method and pharmaceutical use thereof.

BACKGROUND

Cell cycle is an important part of cell vital activity. In normal cell growth, the achievement of cell cycle progression depends on precise and tight regulation of cell cycle by various levels of regulatory factors. The core of these regulatory factors is Cyclin Dependent Kinase (CDK) and its positive and negative regulators, i.e., cyclin and Cyclin Dependent Kinase Inhibitors (CDI). The CDK-Cyclin complex formed by cyclin-dependent protein kinase and cyclin is involved in the growth, proliferation, dormancy, or apoptosis of cells. During the process of cell cycle, cyclin periodically and continuously expresses and degrades, and binds to CDKs that are transiently activated by them, respectively. The phosphorylation of different substrates is catalyzed by CDK activity to realize promotion and conversion of different phases of cell cycle.

Currently, 13 members of the CDK family have been found, and they are CDK1-CDK13, respectively, in which CDK1, CDK2, CDK3, CDK4 and CDK6 are involved in the regulation of cell proliferation, and CDK7, CDK8, CDK9, CDK11, CDK12 and CDK13 are involved in the regulation of transcription.

Cyclin is divided into A-L, and different CDKs connect different subtypes of Cyclin. Among them, the Cyclin D family (Cyclin D1, D2, D3) starts to express in the G1 phase, binds and activates CDK4 and CDK6 to form a CDK4/6-Cyclin D complex, so as to phosphorylate a series of substrates including Retinoblastomaprotein (Rb). After phosphorylation, Rb releases the proteins that are bound to it and are inhibited by it, mainly including transcription factor E2F, which activates and transcripts some genes necessary for entering S phase (M. A. Ke, Advance in Anti-tumor Effect of CDK4/6 Inhibitors, *World Notes on Antibiotics* 2013, 34 (5):197-202). If the balance is broken due to various factors, whether signal for promoting cell proliferation being enhanced or signal for inhibiting cell proliferation being decreased to some extent, cell proliferation will be out of control, and then tumor occurs. It has been found in the study that abnormality of the Cyclin D-CDK4/6-INK4-Rb pathway is present in approximately 80% of human cancers (1. M. Malumbres and M. Barbacid, To cycle or not to cycle: a critical decision in cancer [J], *Nature Reviews Cancer* 2001, 1 (3): 222; 2. G. I. Shapiro, Cyclin-dependent kinase pathways as targets for cancer treatment [J], *J. Clinical Oncology* 2006, 24 (11):1770). The change of this pathway accelerates the process of the G1 phase, such that tumor cells are accelerated in proliferation and gain survival advantage. Therefore, intervention to the pathway has become a therapeutic strategy and thus CDK4/6 has become one of the potential anti-tumor targets.

The advantages of CDK4/6 as an anti-tumor target lie in that: (1) most proliferating cells rely on CDK2 or CDK4/6 proliferation, but CDK4/6 inhibitors do not exhibit cytotoxicity as "pan-CDK inhibitors," such as myelosuppression and intestinal reaction; and (2) Preclinical experiments show that if the level of Cyclin D in cells is increased or p16INK4a is inactivated, the sensitivity of cells to drug can be increased. Since tumor cells exhibit the aforementioned phenomenon relative to normal cells, targeting of drugs is increased to some extent.

In addition to the inhibition of tumor growth, CDK inhibitors are also used in the treatment of other disorders, for example, cardiovascular disorders, including atherosclerosis, restenosis after implantation of a vascular stent, and other cardiovascular disorders caused by abnormal cellular proliferation; for example, in the treatment of diseases caused by fungi, protozoan parasites (such as *Plasmodium falciparum*) and DNA and RNA virus infections, including malaria, AIDS and so on. In addition, it has been further found in the studies that CDK inhibitors can also be used for treating autoimmune diseases (such as psoriasis, rheumatoid arthritis, glomerulonephritis and lupus erythematosus, etc.), and inhibiting the proliferation of inflammatory cells.

Since WO 9811095 discloses a series of 2-pyrimidinamine compounds having cytokine inhibitory activity, a lot of compounds based on such a core structure and having CDK4/6 inhibitory activity have successively appeared in the prior art, and some have become promising candidate drugs, and even entered the phase III clinical trials. For example, compound PD0332991, also known as "Palbociclib," which has been disclosed in WO 2003062236, is represented by structural formula 1, and developed by Pfizer. PD0332991 has $IC_{50}$s of 11 nmol/L and 15 nmol/L for inhibiting CDK4 and CDK6, respectively; and its $IC_{50}$ for inhibiting CDK2, CDK1 and CDK5 is greater than 10 µmol/L (D. W. Fry, P. J. Harvey, and P. R. Keller et al., Specific inhibition of cyclin-dependent kinase 4/6 by PD0332991 and associated antitumor activity in human tumor xenografts [J], *Molecular Cancer Therapeutics* 2004, 3 (11):1427). Compound LEE011 that is being developed by Novartis (disclosed by WO 2011101409) is represented by structural formula 2. Compound LY2835219 (disclosed by WO 2010075074), also known as "Bemaciclib," is represented by structural formula 3; it has been reported that its $IC_{50}$s for inhibiting CDK4 and CDK6 are 2 nmol/L and 9.9 nmol/L, respectively (M. G. Lawrence, S. F. Cai, X. Lin et al., Preclinical characterization of the CDK4/6 inhibitor LY2835219: in-vivo cell cycle-dependent/independent anti-tumor activities alone/in combination with gemcitabine [J], *Invest. New Drugs* (2014), 32:825). Currently, LY2835219 is in phase III clinical trial by Eli Lilly Company.

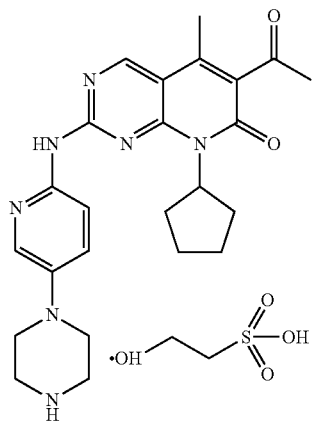

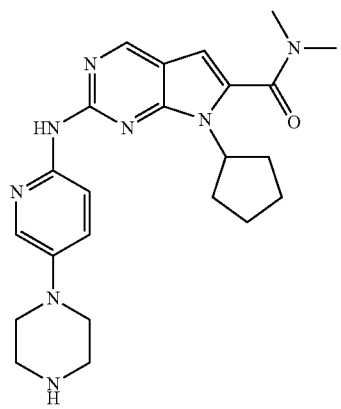

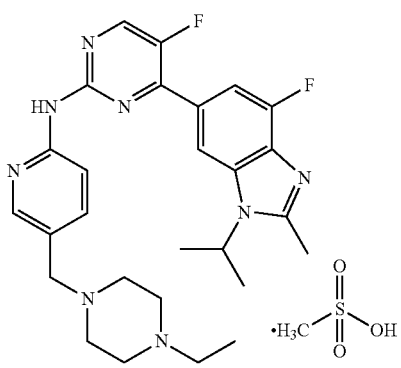

Due to the emergence of these compounds, CDK4/6 has become a clear anti-tumor target. The applicant has also filed a patent application (No. 201510708487.3, filed on Oct. 27, 2015) for a series of new substituted 2-(pyridin-2-yl)aminopyrimidines, which exhibit the activity of selectively inhibiting CDK4/6.

Malignant tumors are still a serious threat to human health. Therefore, it is necessary and urgent to develop CDK4/6 inhibitors with higher activity, selectivity and bioavailability so as to provide more clinical options for the treatment of diseases associated with abnormal cell proliferation, such as cancer.

BRIEF SUMMARY

In view of the above problems, an object of this disclosure is to provide a novel substituted 2-(pyridin-2-yl)aminopyrimidine compound. The compound provided in the disclosure can selectively inhibit the cyclin kinase CDK4/6 and stop the cell in G1 phase, and thus can be used for treating cell proliferative disorder.

In order to achieve the above technical effect, this disclosure provides the following technical solutions:

In one aspect, this disclosure provides a compound of structural formula I, or a tautomer, a mesomer, a racemate, an enantiomer, a diastereomer, a deuterated compound, a prodrug, or a mixture thereof; or pharmaceutically acceptable salts or solvates of the compound of structural formula I or its tautomer, mesomer, racemate, enantiomer, diastereomer, deuterated compound, prodrug or a mixture thereof,

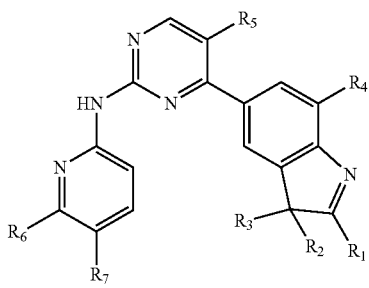

wherein $R_1$, $R_2$ and $R_3$ are each independently selected from a hydrogen atom, unsubstituted $C_1$-$C_6$ hydrocarbon group, or $C_1$-$C_6$ hydrocarbon group substituted by one or more substituents selected from $C_1$-$C_6$ hydrocarbon group, $C_3$-$C_6$ cycloalkane, $C_1$-$C_6$ haloalkyl, $C_1$-$C_6$ alkoxy, hydroxyl, halogen, cyano, —$NR_8R_9$,

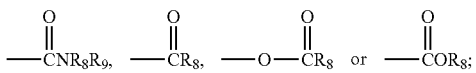

or any two of $R_1$, $R_2$ and $R_3$, together with the C atoms to which they are attached respectively, form a saturated or unsaturated 3- to 7-membered ring;

$R_4$ and $R_5$ are each independently selected from the group consisting of hydrogen and halogen, and at least one of $R_4$ and $R_5$ is halogen;

$R_6$ is selected from the group consisting of a hydrogen atom, $C_1$-$C_6$ alkyl, $C_1$-$C_6$ alkoxy, hydroxyl or halogen;

$R_7$ is

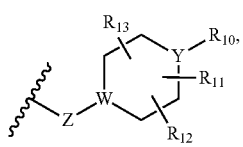

wherein Z is carbonyl, O, S, imino, sulfonyl or

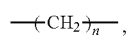

n is an integer from 0 to 4; W and Y are each independently C, N, O or S, but W and Y cannot both be C at the same time, and when Z is O or S, W is C; $R_{10}$, $R_{11}$, $R_{12}$ and $R_{13}$ are each independently selected from a hydrogen atom, $C_1$-$C_6$ alkyl, $C_3$-$C_6$ cycloalkyl, $C_1$-$C_6$ hydroxyalkyl, $C_1$-$C_6$ haloalkyl, $C_1$-$C_6$ alkoxy, hydroxyl, halogen, cyano, —$NR_8R_9$,

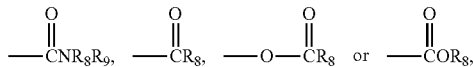

and when Y=N, $R_{10}$ cannot be $NH_2$, —$NHR_8$, —$NR_8R_9$,

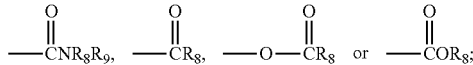

or $R_6$ and $R_7$ together with the C atoms to which they are attached form a 5- to 7-membered heterocycle containing one or more atoms selected from N, O or S, and the 5- to 7-membered heterocycle is substituted by one or more substituents selected from $C_1$-$C_6$ alkyl, $C_3$-$C_6$ cycloalkyl, $C_1$-$C_6$ haloalkyl, $C_1$-$C_6$ alkoxy, $C_1$-$C_6$ hydroxyalkyl, hydroxyl, halogen, cyano, —$NH_2$, —$NHR_8$, —$NR_8R_9$,

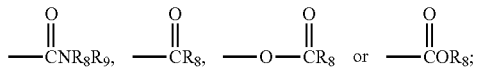

wherein $R_8$ and $R_9$ are each independently selected from the group consisting of a hydrogen atom, $C_1$-$C_6$ alkyl and $C_1$-$C_6$ hydroxyalkyl.

Preferably, $R_1$, $R_2$ and $R_3$ are each independently selected from a hydrogen atom, unsubstituted $C_1$-$C_6$ hydrocarbon group, or a $C_1$-$C_6$ hydrocarbon group substituted by one or more substituents selected from $C_1$-$C_6$ hydrocarbon group, $C_3$-$C_6$ cycloalkyl, $C_1$-$C_6$ haloalkyl, $C_1$-$C_6$ alkoxy, hydroxyl, or halogen.

More preferably, $R_1$, $R_2$ and $R_3$ are each independently selected from a hydrogen atom, an unsubstituted $C_1$-$C_6$ hydrocarbon group or $C_1$-$C_6$ hydrocarbon group substituted by one or more substituents selected from $C_1$-$C_6$ hydrocarbon group, hydroxyl, or halogen.

More preferably, $R_1$, $R_2$ and $R_3$ are each independently selected from a hydrogen atom, unsubstituted linear or branched $C_1$-$C_6$ alkyl, unsubstituted linear or branched $C_2$-$C_4$ alkenyl.

Most preferably, $R_1$, $R_2$ and $R_3$ are each independently selected from a hydrogen atom, unsubstituted linear or branched $C_1$-$C_4$ alkyl.

As another preferred embodiment, $R_2$ and $R_3$, together with the C atoms to which they are both attached, form a saturated or unsaturated 3- to 7-membered ring.

More preferably, $R_2$ and $R_3$, together with the C atoms to which they are both attached, form a saturated 3- to 7-membered ring.

Preferably, $R_4$ and $R_5$ are each independently selected from hydrogen, fluorine or chlorine, and at least one of $R_4$ and $R_5$ is fluorine or chlorine.

More preferably, $R_4$ and $R_5$ are each independently hydrogen or fluorine, and at least one of $R_4$ and $R_5$ is fluorine.

Most preferably, $R_4$ is hydrogen or fluorine, and $R_5$ is fluorine.

Preferably, $R_6$ is selected from a hydrogen atom or $C_1$-$C_6$ alkyl.

Preferably, Z is a carbonyl group, O or

n is an integer from 0 to 4.
More preferably, Z is

n is an integer from 0 to 2, more preferably, n=0 or 1.

Preferably, W and Y are each independently selected from C or N, but W and Y cannot both be C at the same time.

Preferably, $R_{10}$, $R_{11}$, $R_{12}$ and $R_{13}$ are each independently selected from a hydrogen atom, $C_1$-$C_6$ alkyl, $C_3$-$C_6$ cycloalkyl, $C_1$-$C_6$ hydroxyalkyl, $C_1$-$C_6$ haloalkyl, $C_1$-$C_6$ alkoxy, hydroxyl, or —$NR_8R_9$, and when Y=N, $R_{10}$ cannot be —$NR_8R_9$, wherein $R_8$ and $R_9$ are each independently selected from a hydrogen atom and $C_1$-$C_4$ alkyl.

More preferably, $R_{10}$, $R_{11}$, $R_{12}$ and $R_{13}$ are each independently selected from a hydrogen atom, $C_1$-$C_6$ alkyl, $C_1$-$C_6$ hydroxyalkyl, $C_1$-$C_6$ haloalkyl, $C_1$-$C_6$ alkoxy or —$NR_8R_9$, wherein $R_8$ and $R_9$ are independently selected from a hydrogen atom and $C_1$-$C_4$ alkyl.

More preferably, $R_7$ is selected from the substituents having the following structures:

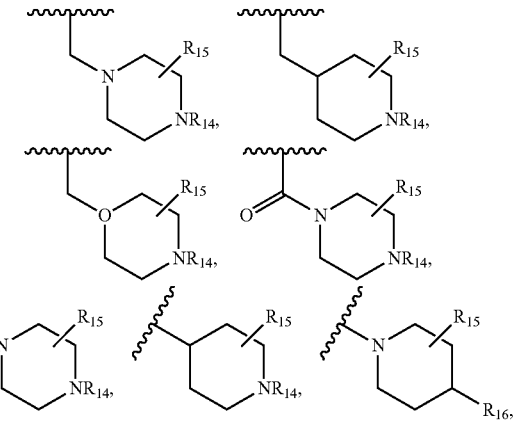

wherein $R_{14}$ and $R_{15}$ are each independently selected from a hydrogen atom, $C_1$-$C_6$ alkyl, $C_3$-$C_6$ cycloalkyl, $C_1$-$C_6$ haloalkyl, $C_1$-$C_6$ hydroxyalkyl, $C_1$-$C_6$ alkoxy or hydroxyl; $R_{16}$ is selected from a hydrogen atom, $C_3$-$C_6$ cycloalkyl, $C_1$-$C_6$ haloalkyl, $C_1$-$C_6$ hydroxyalkyl, $C_1$-$C_6$ alkoxy, hydroxyl, or —$NR_8R_9$, wherein $R_8$ and $R_9$ are independently selected from a hydrogen atom and $C_1$-$C_4$ alkyl.

More preferably, $R_{14}$ and $R_{15}$ are each independently selected from the group consisting of a hydrogen atom, $C_1$-$C_6$ alkyl, $C_3$-$C_6$ cycloalkyl, and $C_1$-$C_6$ hydroxyalkyl; $R_{16}$ is selected from a hydrogen atom, $C_1$-$C_6$ alkyl, $C_3$-$C_6$ cycloalkyl, $C_1$-$C_6$ hydroxyalkyl or —$NR_8R_9$, wherein $R_8$ and $R_9$ are independently selected from a hydrogen atom and $C_1$-$C_4$ alkyl.

As another preferred embodiment, $R_6$ and $R_7$ together with the C atoms to which they are attached form a 6-membered heterocycle containing one or more atoms selected from N, O or S.

More preferably, $R_6$ and $R_7$ together with the C atoms to which they are attached form a 6-membered heterocycle containing N.

More preferably, $R_6$ and $R_7$ together with the C atoms to which they are attached form the following chemical structure:

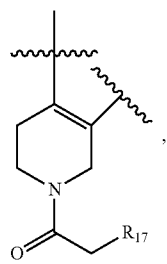

wherein $R_{17}$ is selected from hydroxyl or $C_1$-$C_3$ alkoxy; further preferably, $R_{17}$ is hydroxyl.

As a preferred embodiment, the disclosure further provides the compounds of structural formula II, III, IV or V, or their respective tautomer, mesomer, racemate, enantiomer, diastereomer, deuterated compound, prodrug, or mixture thereof; or pharmaceutically acceptable salts or solvates of the compounds of formula II, III, IV or V or their respective tautomer, mesomer, racemate, enantiomer, diastereomer, deuterated compound, prodrug or mixture thereof,

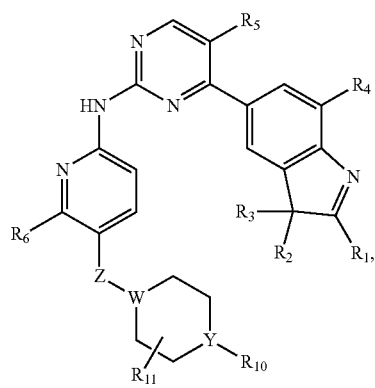

II

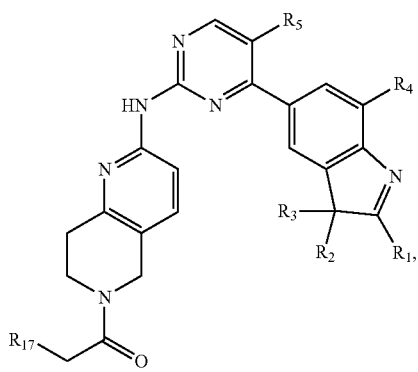

III

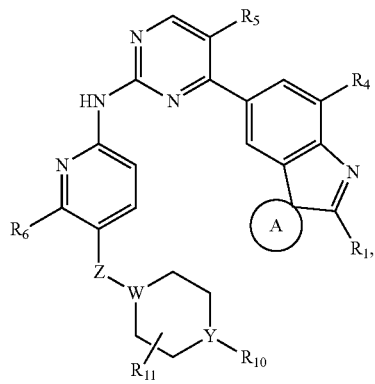

IV

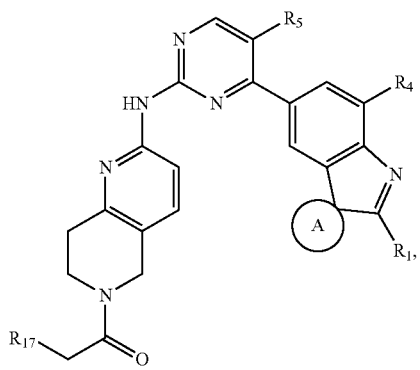

V wherein Z, W, Y, $R_1$, $R_2$, $R_3$, $R_4$, $R_5$, $R_6$, $R_{10}$, $R_{11}$ and $R_{17}$ are defined as above, ring A is a saturated 3- to 7-membered ring.

Preferably, ring A is a saturated 3- to 6-membered ring.

More preferably, the disclosure provides a compound of structural formula VIII, or a tautomer, a mesomer, a racemate, an enantiomer, a diastereomer, a deuterated compound, a prodrug, or a mixture thereof; or pharmaceutically acceptable salts or solvates of the compound of structural formula VIII or its tautomer, mesomer, racemate, enantiomer, diastereomer, deuterated compound, prodrug or mixture thereof,

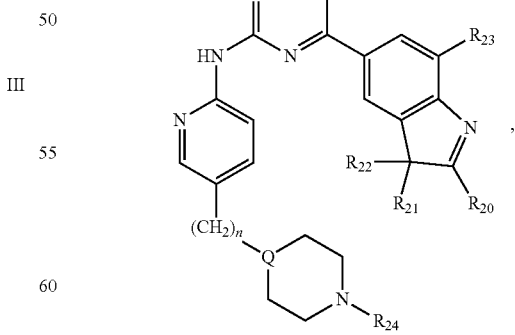

VIII wherein $R_{20}$, $R_{21}$, $R_{22}$ are each independently selected from $C_1$-$C_4$ alkyl, or $R_{20}$ is $C_1$-$C_4$ alkyl, and $R_{21}$ and $R_{22}$ together with the C atom to which they are attached form a saturated 5- to 6-membered ring; $R_{23}$ is selected from hydrogen or fluorine; n=0 or 1; $R_{24}$ is selected from the group consisting of hydrogen, $C_1$-$C_4$ alkyl or $C_1$-$C_4$ hydroxyalkyl, Q is C or N.

As a more preferable embodiment, this disclosure provides compounds of the following structures, or a tautomer, a mesomer, a racemate, an enantiomer, a diastereomer, a deuterated compound, a prodrug, or a mixture thereof; or pharmaceutically acceptable salts or solvates of the compounds of the structures or their respective tautomer, mesomer, racemate, enantiomer, diastereomer, deuterated compound, prodrug or mixture thereof,

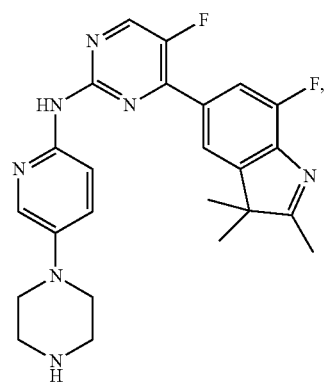

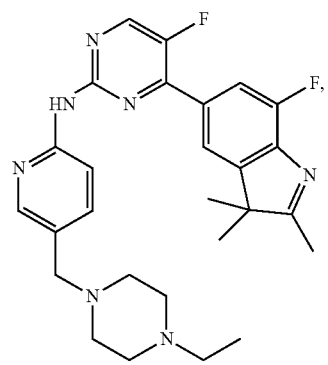

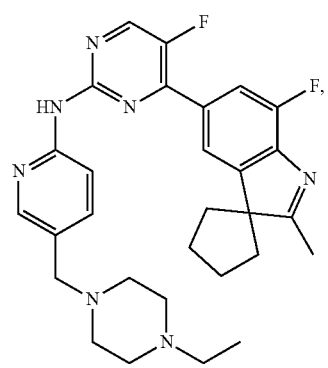

-continued

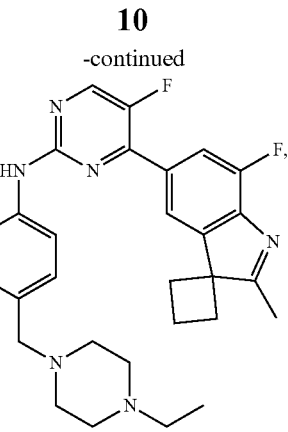

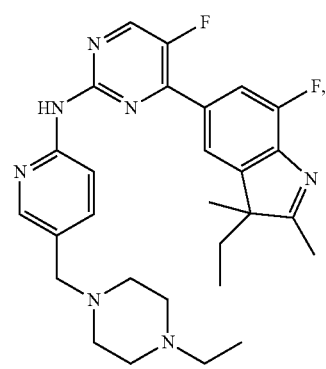

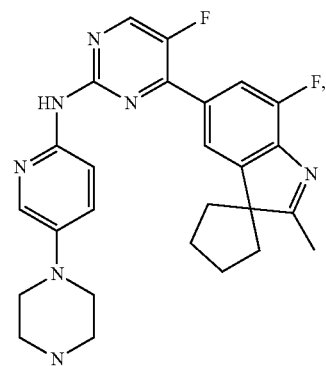

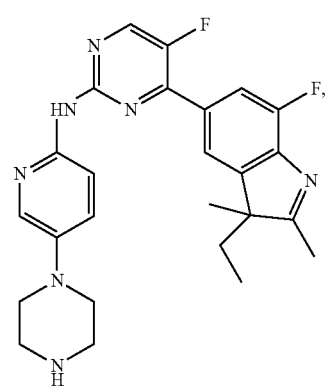

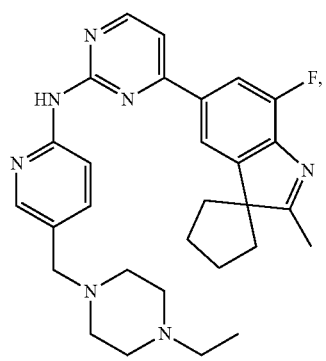
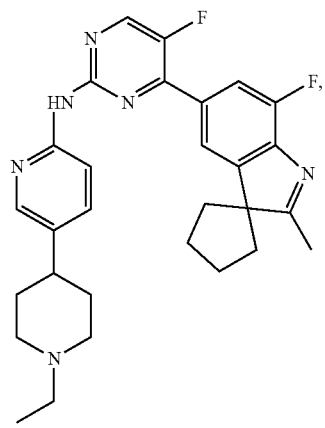
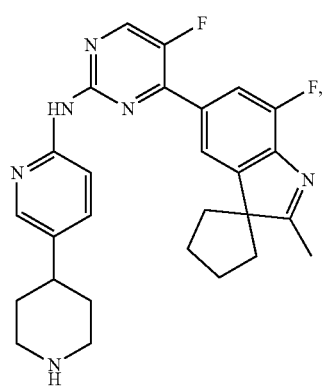
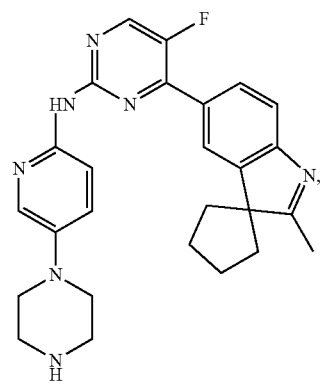
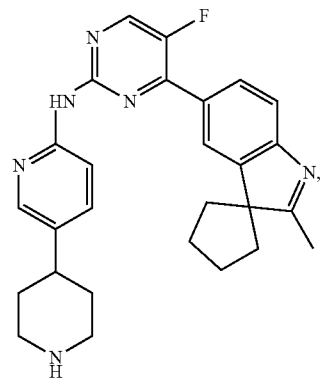

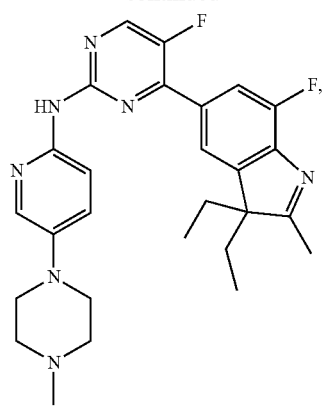
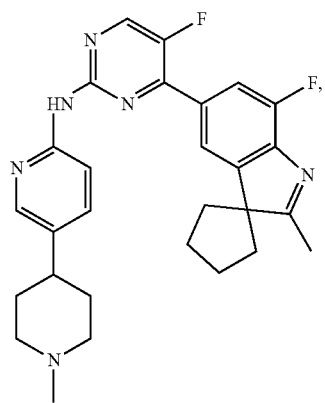
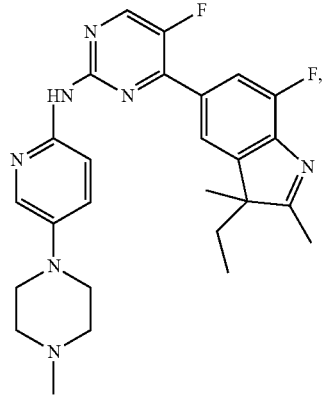
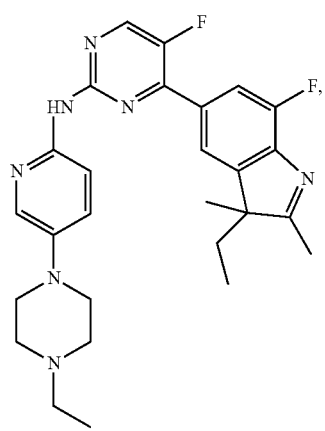
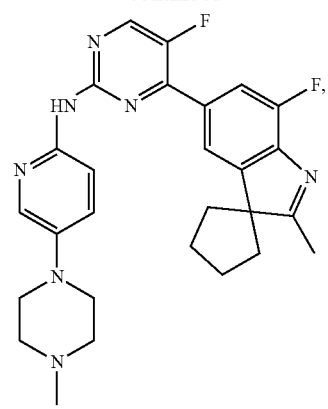
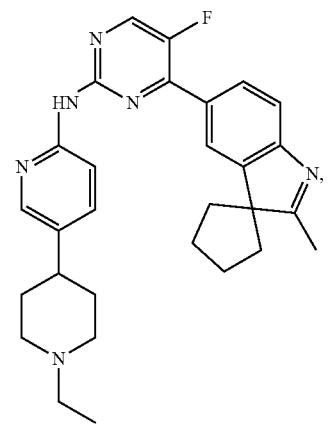
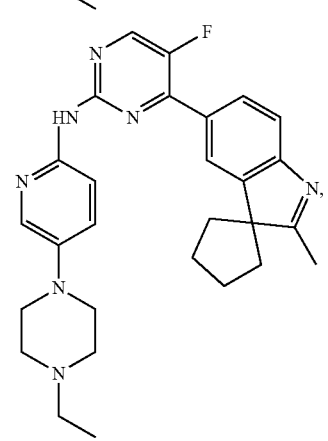
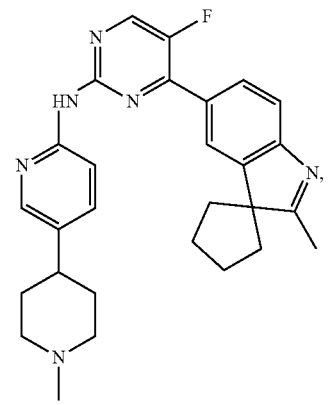

-continued

-continued
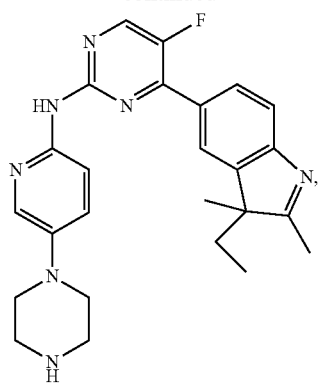
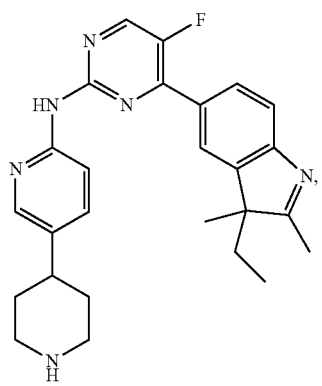
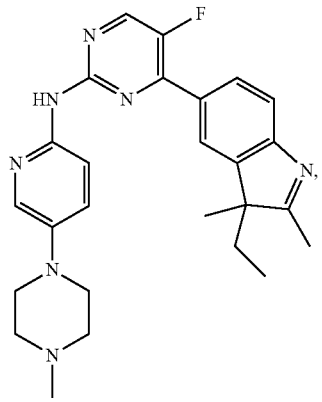
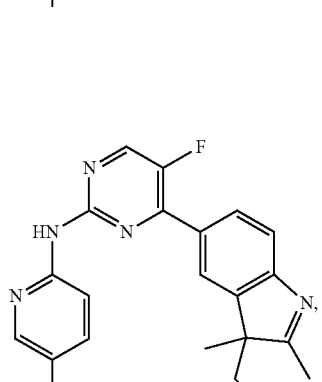
-continued
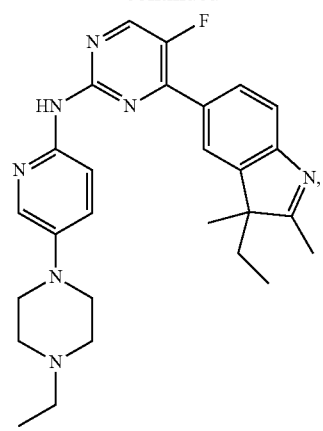
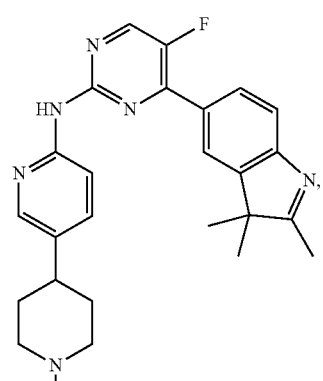
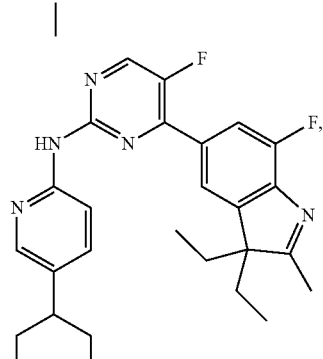
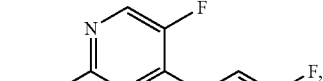
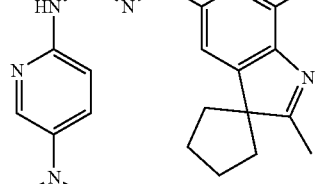
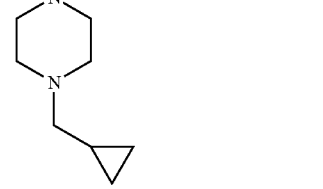

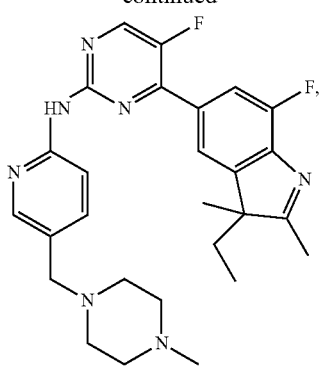

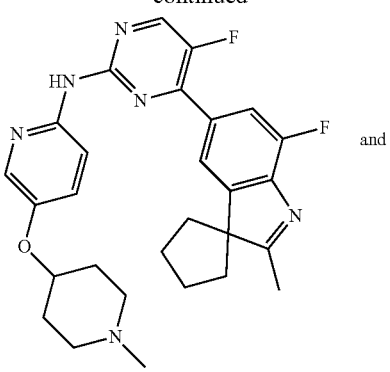

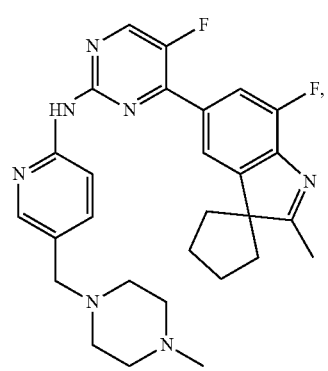

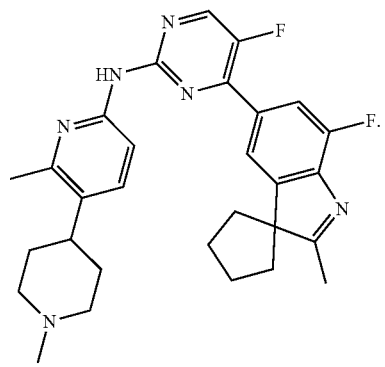 [SMILES: CC1=Nc2c(F)cc(-c3nc(Nc4ccc(C5CCN(C)CC5)c(C)n4)ncc3F)cc2C12CCCC2]

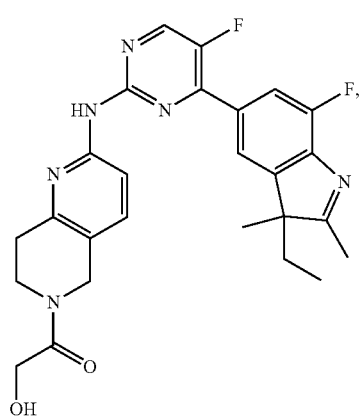

The compounds according to the present disclosure also include all the above mentioned compounds that are isotopically labeled.

In another aspect, the disclosure further provides a compound of structural formula VI, or a tautomer, a mesomer, a racemate, an enantiomer, a diastereomer, a deuterated compound, a prodrug, or a mixture thereof; or pharmaceutically acceptable salts or solvates of the compound of structural formula VI or its tautomer, mesomer, racemate, enantiomer, diastereomer, deuterated compound, prodrug, or a mixture thereof,

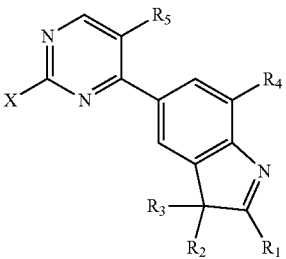

VI

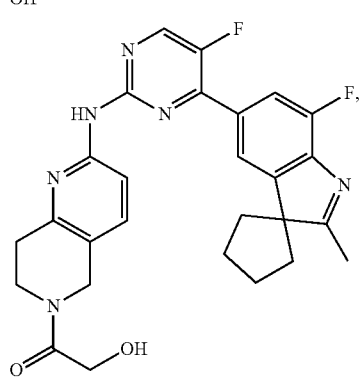

wherein $R_1$, $R_2$, $R_3$, $R_4$ and $R_5$ are defined as above, X is a leaving group or an amino group.

Preferably, X is halogen or amino, more preferably fluorine, bromine, chlorine or amino.

In another aspect, this disclosure provides a method for preparing the compound of structural formula I, comprising carrying out a palladium-catalyzed coupling reaction between a compound of formula VI and a compound of formula VII in a solvent to give a compound of formula I,

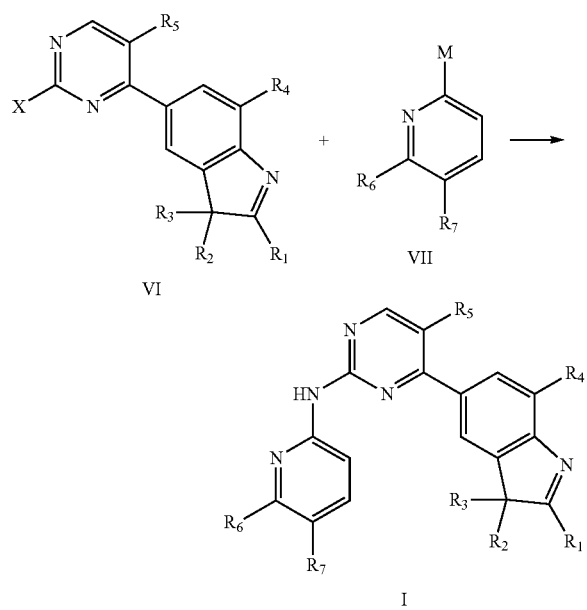

wherein $R_1$, $R_2$, $R_3$, $R_4$, $R_5$, $R_6$ and $R_7$ are defined as above; X and M are each independently a leaving group or amino, only one of X and M is amino and one of the two must be amino;

preferably, the leaving group is halogen;

more preferably, the leaving group is fluorine, bromine or chlorine.

Wherein, the above preparation method may further comprise removing the protective group.

Wherein, the above preparation method may further comprise product separation and/or purification, and the separation and/or purification may be performed by a method generally used in organic synthesis, for example, a suitable combination of the methods of filtration, extraction, washing, concentration, chromatography and the like.

In another aspect, the disclosure provides use of the compounds of structural formulas I-V and VIII, or their respective tautomer, mesomer, racemate, enantiomer, diastereomer, deuterated compound, prodrug, or mixture thereof; or pharmaceutically acceptable salts or solvates of the compounds of formulas I-V and VIII or their respective tautomer, mesomer, racemate, enantiomer, diastereomer, deuterated compound, prodrug or mixture thereof, in the manufacture of a pharmaceutical formulation for the treatment of a cell proliferative disorder.

Preferably, the pharmaceutical formulation comprises a pharmaceutically acceptable excipient.

Preferably, the cell proliferative disorder refers to cancer of mammal or human, more preferably refers to human cancer, including malignant solid tumors and malignant non-solid tumors, specifically including, but not limited to, breast cancer, lung cancer, prostate cancer, leukemia, brain cancer, gastric cancer, and glioma.

Preferably, the cell proliferative disorder may also be AIDS, atherosclerosis, and restenosis after implantation of a vascular stent.

Preferably, "use" refers to the use of the compounds of structural formulas I-V and VIII, or their respective tautomer, mesomer, racemate, enantiomer, diastereomer, deuterated compound, prodrug, or mixture thereof; or pharmaceutically acceptable salts or solvates of the compounds of formulas I-V and VIII or their respective tautomer, mesomer, racemate, enantiomer, diastereomer, deuterated compound, prodrug or mixture thereof, as the sole active ingredient or in combination with other biologically active substances, in the manufacture of a pharmaceutical formulation for the treatment of a cell proliferative disorder.

The other biologically active substances include, but are not limited to, anticancer agents, immunosuppressive agents and anti-viral agents; wherein the anticancer agent is selected from alkylating agent (such as cyclophosphamide, ifosfamide, thiotepa, semustine, mechlorethamine hydrochloride, busulfan, chlorambucil, melphalan, nitrocaphane, formylmelphalan, carmustine, lomustine, altretamine, dibromomannitol, temozolomide, and the like), antimetabolite antineoplastic drugs (such as cytarabine, fluorouracil, methotrexate, hydroxyurea, tegafur, meisoindigo, mercaptopurine and the like), platinum complexing agent (such as cisplatin, carboplatin, oxaliplatin and the like), antibiotic antineoplastic drugs (actinomycin D, mitomycin, doxorubicin, pingyangmycin, epirubicin, pirarubicin, daunorubicin, bleomycin, and the like), naturally derived antineoplastic drugs (homoharringtonine and its derivatives, vincristine and its derivatives, hydroxycamptothecin and its derivatives, etoposide and its derivatives, vindesine and its derivatives, vinblastine and its derivatives, vinorelbine bitartrate, taxol and its derivatives, colchicine and its derivatives, elemene and its derivatives and the like), hormonal antineoplastic drugs (such as aminoglutethimide, tamoxifen, dexamethasone, dutasteride, flutamide, gonadorelin, leuprolide acetate, letrozole and the like), VEGFR or EGFR inhibitors (such as sunitinib, sorafenib, imatinib, gefitinib, erlotinib, vandetanib, pazopanib, lapatinib, canertinib, afatinib, mubritinib, dasatinib, neratinib and the like), antibody antineoplastic drugs (such as trastuzumab, pertuzumab, rituximab, panitumumab, bevacizumab, ipilimumab, ofatumumab, ramucirumab and the like), mTOR inhibitors (such as everolimus, sirolimus, zotarolimus and the like), and the drugs for treating brain tumors, such as temozolomide and the like.

In yet another aspect, this disclosure provides a combination product for treating a cell proliferative disorder, wherein the combination product comprises one or more compounds selected from the compounds of structural formulas I-V and VIII, or their respective tautomer, mesomer, racemate, enantiomer, diastereomer, deuterated compound, prodrug, or mixture thereof; or pharmaceutically acceptable salts or solvates of the compounds of formulas I-V and VIII or their respective tautomer, mesomer, racemate, enantiomer, diastereomer, deuterated compound, prodrug or mixture thereof.

Preferably, the combination product further includes pharmaceutically acceptable excipients, and/or the combination product is a kit.

In another aspect, the disclosure further provides a method for treating a cell proliferative disorder, comprising administering to a patient in need thereof, orally or non-orally, an effective amount of the compounds of the disclosure or the above mentioned combination product.

Preferably, the above method for treating a cell proliferative disorder comprises administering to a patient, orally or non-orally, an effective amount of the compounds of the disclosure and other biologically active substances. Other biologically active substances include, but are not limited to, anticancer agents, immunosuppressive agents and antiviral agents; wherein the anticancer agent is selected from alkylating agent (such as cyclophosphamide, ifosfamide, thiotepa, semustine, mechlorethamine hydrochloride, busulfan, chlorambucil, melphalan, nitrocaphane, formylmelphalan, carmustine, lomustine, altretamine, dibromomannitol, temozolomide and the like), antimetabolite antineoplastic drugs (such as cytarabine, fluorouracil, methotrexate, hydroxyurea, tegafur, meisoindigo, mercaptopurine and the like), platinum complexing agent (such as cisplatin, carboplatin, and oxaliplatin), antibiotic antineoplastic drugs (actinomycin D, mitomycin, doxorubicin, pingyangmycin, epirubicin, pirarubicin, daunorubicin, bleomycin and the like), naturally derived antineoplastic drugs (homoharringtonine and its derivatives, vincristine and its derivatives, hydroxycamptothecin and its derivatives, etoposide and its derivatives, vindesine and its derivatives, vinblastine and its derivatives, vinorelbine bitartrate, taxol and its derivatives, colchicine and its derivatives, elemene and its derivatives and the like), hormonal antineoplastic drugs (such as aminoglutethimide, tamoxifen, dexamethasone, dutasteride, flutamide, gonadorelin, leuprolide acetate, letrozole and the like), VEGFR or EGFR inhibitors (such as sunitinib, sorafenib, imatinib, gefitinib, erlotinib, vandetanib, pazopanib, lapatinib, canertinib, afatinib, mubritinib, dasatinib, neratinib and the like), antibody antineoplastic drugs (such as trastuzumab, pertuzumab, rituximab, panitumumab, bevacizumab, ipilimumab, ofatumumab, ramucirumab and the like), mTOR inhibitors (such as everolimus, sirolimus zotarolimus and the like), and the drugs for treating brain tumor, such as temozolomide and the like.

The oral or non-oral route can be delivery to the patient orally or by injection, patch, spray, and one or more other known routes. The effective amount can include an amount effective to treat, reduce, moderate, alleviate, eliminate one or more symptoms of a condition sought to be treated or alternatively sought to be avoided, or an amount effective to additionally generate clinically identifiable advantageous changes in the condition or its effect.

In another aspect, this disclosure provides a compound for the treatment of a cell proliferative disorder or their respective tautomer, mesomer, racemate, enantiomer, diastereomer, deuterated compound, prodrug, or mixture thereof; or pharmaceutically acceptable salts or solvates of the compounds of formulas I-V and VIII or their respective tautomer, mesomer, racemate, enantiomer, diastereomer, deuterated compound, prodrug or mixture thereof, wherein the structural formula of the compound is one or more structural formulas selected from the group consisting of the structural formulas I-V and VIII;

preferably, the cell proliferative disorder refers to cancer of mammal or human, more preferably refers to human cancer, including malignant solid tumors and malignant non-solid tumors, specifically including, but not limited to, breast cancer, lung cancer, prostate cancer, leukemia, brain cancer, glioma, and gastric cancer; and/or the cell proliferative disorder is one or more diseases selected from the group consisting of AIDS, atherosclerosis, and restenosis after implantation of a vascular stent.

In the description of this disclosure, unless otherwise specified, the "$C_1$-$C_6$ alkyl" refers to a linear or branched $C_1$-$C_6$ alkyl; the "$C_1$-$C_4$ alkyl" refers to a linear or branched $C_1$-$C_4$ alkyl, preferably methyl, ethyl, propyl or isopropyl. The "$C_1$-$C_6$ alkoxy" refers to a $C_1$-$C_6$ linear or branched alkoxy, preferably a $C_1$-$C_4$ linear or branched alkoxy, more preferably methoxy, ethoxy, propoxy or 2-methylethoxy. The "$C_3$-$C_6$ cycloalkyl" refers to an unsubstituted $C_3$-$C_6$ cycloalkyl or $C_3$-$C_6$ cycloalkyl substituted by $C_1$-$C_4$ alkyl and/or $C_1$-$C_4$ alkoxy, preferably unsubstituted $C_3$-$C_6$ cycloalkyl or $C_3$-$C_6$ cycloalkyl substituted by $C_1$-$C_4$ alkyl and/or $C_1$-$C_4$ alkoxy, more preferably cyclopropyl, cyclobutyl, methyl cyclopropyl, cyclopentyl or cyclohexyl. The "halogen" refers to bromine, chlorine or fluorine. The "$C_1$-$C_6$ haloalkyl" refers to linear or branched $C_1$-$C_6$ alkyl substituted with bromine, chlorine, or fluorine, preferably linear or branched $C_1$-$C_4$ alkyl substituted with chlorine or fluorine, more preferably monofluoromethyl, difluoromethyl, trifluoromethyl, monochloromethyl, dichloromethyl, trichloromethyl, 1-fluoroethyl, 1-chloroethyl, and 1-chloropropyl.

Existing research suggests that the toxicity of inhibitors of CDKs is mainly related to their inhibition of CDK1 and other protein kinases, such as Pim-1, a threonine/serine kinase encoded by a proto oncogene of the same name. Therefore, as CDK inhibitor compounds, they are expected to have more significant difference between the effect on CDK4/CDK6 and that on CDK1 and other kinases, that is, selective inhibition of CDK4/CDK6. The compounds provided by the disclosure are superior to or comparable in activity to LY2835219, a candidate currently being in phase III clinical trials, and some compounds exhibit better kinase selectivity. Moreover, the preferred compound (prepared in Example 17) is well absorbed orally and has good blood-brain distribution. The above results indicate that the compounds of the disclosure are promising to be developed into new drugs for the treatment of diseases associated with cell proliferation, especially malignant tumors, especially brain cancer.

DETAILED DESCRIPTION

This disclosure is described below with reference to specific examples. It will be understood by a person skilled in the art that these examples are merely illustrative of the disclosure and are not intended to limit the scope of the invention in any way.

The compounds of formula VI of the disclosure are key intermediates for the synthesis of the compounds of formula I, and they are subjected to a palladium-catalyzed coupling reaction with the compounds of formula VII in a solvent to give the compounds of formula I.

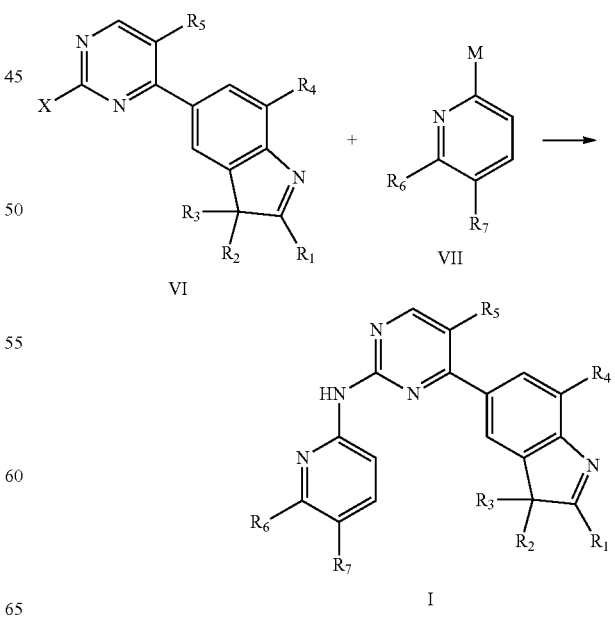

The compounds of formula VI can be synthesized by the following reaction scheme:

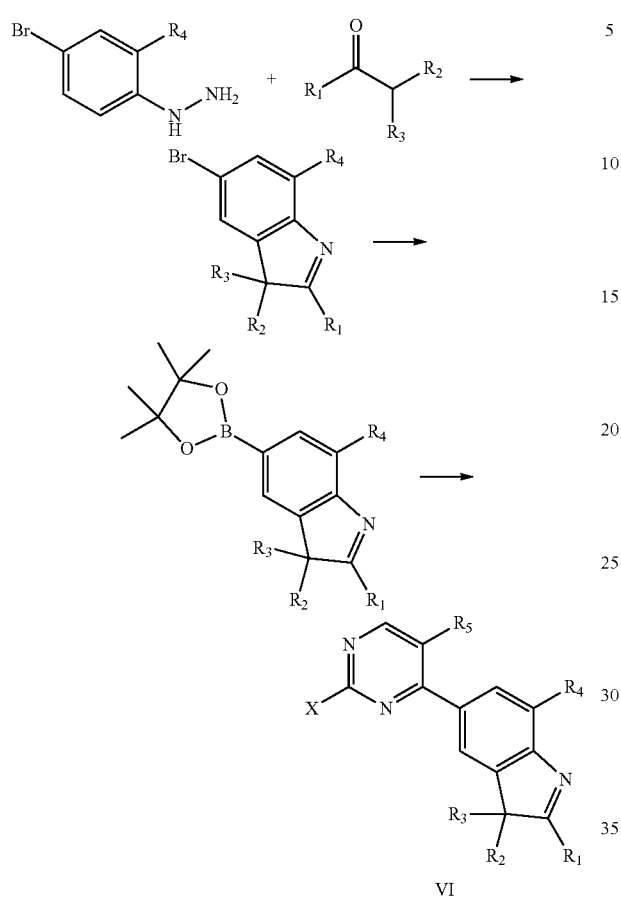

wherein $R_1$, $R_2$, $R_3$, $R_4$, $R_5$, $R_6$ and $R_7$ are defined as above; X is a leaving group or amino group.

Preferably, $R_1$, $R_2$ and $R_3$ are each independently selected from a hydrogen atom, unsubstituted $C_1$-$C_6$ hydrocarbon group, or a $C_1$-$C_6$ hydrocarbon group substituted by one or more substituents selected from $C_1$-$C_6$ hydrocarbon group, hydroxyl, or halogen.

More preferably, $R_1$, $R_2$ and $R_3$ are each independently selected from a hydrogen atom, unsubstituted linear or branched $C_1$-$C_6$ alkyl, unsubstituted linear or branched $C_2$-$C_4$ alkenyl.

Most preferably, $R_1$, $R_2$ and $R_3$ are each independently selected from a hydrogen atom, unsubstituted linear or branched $C_1$-$C_4$ alkyl.

Alternatively, as another preferred mode, $R_1$ is defined as above, and $R_2$ and $R_3$ together with the C atom to which they are attached form a saturated or unsaturated 3- to 7-membered ring; more preferably, $R_2$ and $R_3$ together with the C atom to which they are attached form a saturated 3- to 7-membered ring.

Preferably, $R_4$ and $R_5$ are each independently hydrogen or fluorine, and at least one of $R_4$ and $R_5$ is fluorine.

X is preferably halogen or amino, more preferably fluorine, bromine, chlorine or amino.

$R_6$ is preferably a hydrogen atom or $C_1$-$C_4$ alkyl.

$R_7$ is preferably a substituent of the following structure:

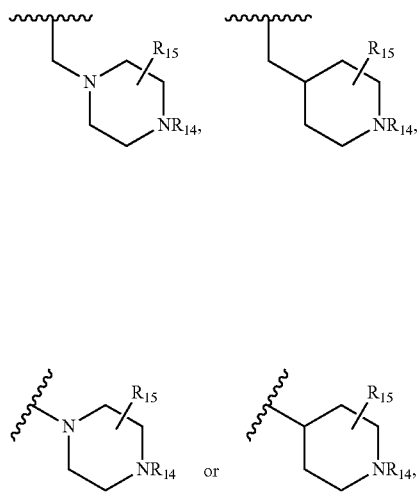

wherein, $R_{14}$ and $R_{15}$ are each independently selected from the group consisting of a hydrogen atom, $C_1$-$C_4$ alkyl and $C_1$-$C_4$ hydroxyalkyl.

Alternatively, as another preferred embodiment, $R_6$ and $R_7$ together with the C atom to which they are attached form a chemical structure as follows:

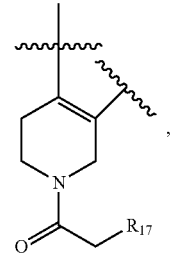

wherein, $R_{17}$ is selected from hydroxyl or $C_1$-$C_3$ alkoxy; more preferably, hydroxyl.

Unless otherwise specified, all of the experimental methods in the following examples are conventional methods. Unless otherwise specified, the chemical raw materials, reagents and the like used in the following examples are commercially available products.

Abbreviations and their meanings appearing in the examples of this disclosure are given as follows:

PE: petroleum ether

EA: ethyl acetate

DCM: dichloromethane

MeOH: methanol

Pd(dppf)Cl$_2$: [1,1'-bis (diphenylphosphino) ferrocene] palladium dichloride

Pd(PPh$_3$)$_4$: tetrakis (triphenylphosphine) palladium

Pd$_2$(dba)$_3$: tris(dibenzylideneacetone)dipalladium

NaHB(OAc)$_3$: sodium triacetoxyborohydride

LHMDS: lithium hexamethyldisilazide

DAPI: DAPI fluorescent dye

Example 1

5-fluoro-4-(7-fluoro-2,3,3-trimethyl-3H-indol-5-yl)-N-(5-(piperazin-1-yl) pyridin-2-yl)pyrimidine-2-amino

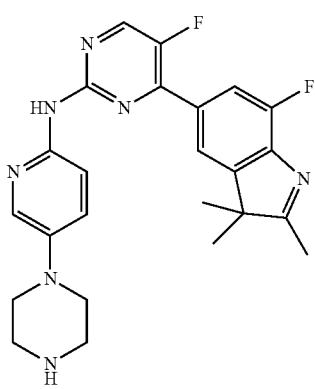 [SMILES: CC1=Nc2c(F)cc(-c3nc(Nc4ccc(N5CCNCC5)cn4)ncc3F)cc2C1(C)C]

Step 1: 4-(6-nitropyridin-3-yl)piperazine-1-carboxylic acid t-butyl ester

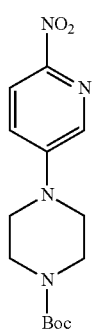

A reaction flask was charged with 5-bromo-2-nitropyridine (5.0 g, 24.63 mmol), piperazine-1-carboxylic acid t-butyl ester (5.04 g, 27.09 mol), acetonitrile (30 mL) and diisopropylethylamine (4.77 g, 36.94 mmol). The mixture was allowed to react under refluxing for 2 hours. The reaction product was subjected to rotary evaporation to remove solvent, and separated by column chromatography (PE/EA=1:1 to DCM/MeOH=20:1) to obtain the titled compound (3.8 g, yellow solid).

MS (ESI): mass calcd. for $C_{14}H_{20}N_4O_4$ 308.1, m/z found 309.1 [M+H]$^+$.

Step 2: 4-(6-aminopyridin-3-yl)piperazine-1-carboxylic acid t-butyl ester

A reaction flask was charged with 4-(6-nitropyridin-3-yl)piperazine-1-carboxylic acid t-butyl ester (0.92 g, 3.0 mmol) prepared in Step 1, ethyl acetate/methanol (10 mL/10 mL) and Pd/C (0.1 g), and introduced with hydrogen gas. The reaction was carried out at room temperature for 2 hours. The reaction product was filtered, and concentrated to obtain the titled compound (792 mg, off-white solid).

MS (ESI): mass calcd. for $C_{14}H_{22}N_4O_2$ 278.2, m/z found 279.2 [M+H]$^+$.

Step 3: Preparation of 5-bromo-7-fluoro-2,3,3-trimethyl-3H-indole

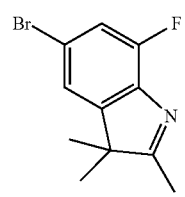

A reaction flask was charged with (4-bromo-2-fluorophenyl)hydrazine hydrochloride (1.0 g, 4.14 mmol), acetic acid (10 ml), and 3-methyl-2-butanone (0.32 g, 4.14 mmol). The mixture was allowed to react under refluxing for 5 hours. The reaction product was subjected to rotary evaporation to remove solvent, added with 20 ml of water, and extracted with ethyl acetate three times (20 ml for each time). The combined organic phase was washed once with 25 ml of saturated sodium chloride aqueous solution, dried with anhydrous sodium sulfate, filtered, subjected to rotary evaporation, and separated by column chromatography (DCM:MeOH=50:1 to 25:1) to obtain the titled compound (420 mg, yellow solid).

$^1$H-NMR (400 MHz, CDCl$_3$) δ 7.23-7.21 (m, 2H), 2.30 (s, 3H), 1.32 (s, 6H).

MS (ESI): m/z 258.0 [M+H]$^+$.

Step 4: Preparation of 7-fluoro-2,3,3-trimethyl-5-(4,4,5,5-tetramethyl-1,3,2-dioxaborolan-2-yl)-3H-indole

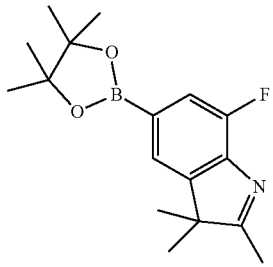 [SMILES: CC1=Nc2c(F)cc(B3OC(C)(C)C(C)(C)O3)cc2C1(C)C]

A reaction flask was charged with 5-bromo-7-fluoro-2,3,3-trimethyl-3H-indole (400.0 mg, 1.56 mmol) prepared in Step 3, 4,4,4',4',5,5,5',5'-octamethyl-2,2'-bis(1,3,2-dioxaborolane) (436.5 mg, 1.71 mmol), potassium acetate (306.3 mg, 3.12 mmol), dixoane (10 ml), and Pd(dppf)Cl$_2$ (228.7 mg, 0.32 mmol). The mixture was heated to 90° C. under protection of nitrogen gas, and allowed to react overnight. The reaction product was cooled to room temperature, filtered, added with 10 ml of water, and extracted with ethyl acetate three times (20 ml for each time). The organic phase of ethyl acetate was combined, washed with 25 ml of saturated salt solution once, dried with anhydrous sodium sulfate, filtered, concentrated and separated by silica gel column chromatography (DCM:MeOH=50:1-30:1) to obtain the titled compound (306.5 mg, yellow oil).

MS (ESI): m/z 304.1 [M+H]$^+$

Step 5: Preparation of 5-(2-chloro-5-fluoropyrimidin-4-yl)-7-fluoro-2,3,3-trimethyl-3H-indole

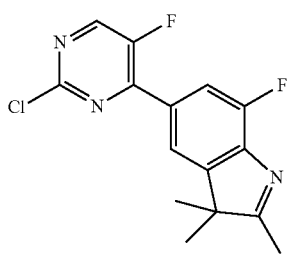 [SMILES: CC1=Nc2c(F)cc(-c3nc(Cl)ncc3F)cc2C1(C)C]

A microwave reaction flask was charged with 7-fluoro-2,3,3-trimethyl-5-(4,4,5,5-tetramethyl-1,3,2-dioxaborolan-2-yl)-3H-indole (300 mg, 0.99 mmol) prepared in step 4, 2,4-dichloro-5-fluoropyrimidine (181.8 mg, 1.08 mmol), potassium phosphate (419.8 mg, 1.98 mmol), dioxane/water (4 mL/1 mL) and Pd (PPh$_3$)$_4$ (114.5 mg, 0.09 mmol). Microwave reaction was carried out under the protection of nitrogen gas at 130° C. for 1 hour. The reaction mixture was cooled to room temperature, filtered, added with 10 mL of water, and extracted with dichloromethane three times (15 ml for each time). The organic phases were combined, washed with 20 ml of saturated sodium chloride aqueous solution once, then dried with anhydrous sodium sulfate, filtered, subjected to rotary evaporation, and separated by silica gel column chromatography (DCM:MeOH=100:1-50:1) to obtain the titled compound (301.2 mg, yellow solid).

MS (ESI): mass calcd. for C$_{15}$H$_{12}$ClF$_2$N$_3$ 307.1, m/z found 308.1 [M+H]$^+$.

Step 6: Preparation of 4-(6-((5-fluoro-4-(7-fluoro-2,3,3-trimethyl-3H-indol-5-yl)pyrimidin-2-yl)amino)pyridin-3-yl)piperazine-1-carboxylic acid t-butyl ester

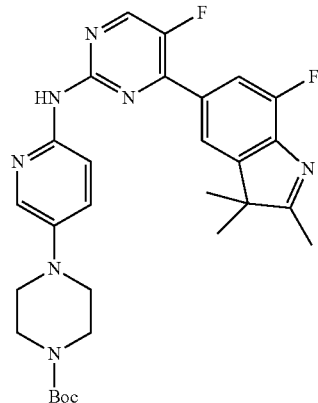 [SMILES: CC1=Nc2c(F)cc(-c3nc(Nc4ccc(N5CCN(C(=O)OC(C)(C)C)CC5)cn4)ncc3F)cc2C1(C)C]

A reaction flask was charged with 5-(2-chloro-5-fluoropyrimidin-4-yl)-7-fluoro-2,3,3-trimethyl-3H-indole (150.0 mg, 0.48 mmol) prepared in Step 5, 4-(6-aminopyridin-3-yl)piperazine-1-carboxylic acid t-butyl ester (135.8 mg, 0.48 mmol) prepared in Step 2, cesium carbonate (371.6 mg, 0.96 mmol), dioxane (3 ml), Pd$_2$(dba)$_3$ (44.7 mg, 0.05 mmol), and 4,5-bis (diphenylphosphino)-9,9-dimethylxanthene (30.4 mg, 0.05 mmol). The mixture was heated to 150° C. under the protection of nitrogen gas to conduct microwave reaction for 1 hour. The reaction product was cooled to room temperature, filtered, added with 10 ml of water, and extracted with dichloromethane three times (10 ml for each time). The organic phases were combined, washed with 30 ml of saturated sodium chloride aqueous solution once, dried with anhydrous sodium sulfate, filtered, concentrated and separated by silica gel column chromatography (DCM/MeOH=50:1) to obtain the titled compound (53.4 mg, yellow solid).

MS (ESI): mass calcd. for C$_{29}$H$_{33}$F$_2$N$_7$O$_2$ 549.3, m/z found 550.3 [M+H]$^+$.

Step 7: Preparation of 5-fluoro-4-(7-fluoro-2,3,3-trimethyl-3H-indol-5-yl)-N-(5-(piperazin-1-yl)pyridin-2-yl)pyrimidine-2-amino trifluoroacetate

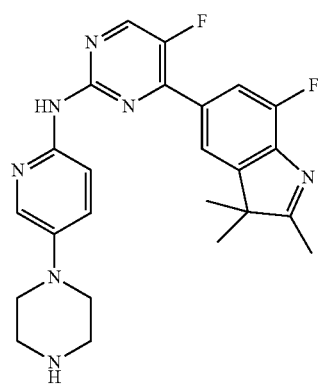 [SMILES: CC1=Nc2c(F)cc(-c3nc(Nc4ccc(N5CCNCC5)cn4)ncc3F)cc2C1(C)C]

A reaction flask was charged with 4-(6-((5-fluoro-4-(7-fluoro-2,3,3-trimethyl-3H-indol-5-yl)pyrimidin-2-yl)amino)pyridin-3-yl) piperazine-1-carboxylic acid t-butyl ester (30.0 mg, 0.054 mmol) prepared in Step 6, dichloromethane (4 ml) and trifluoroacetic acid (1 ml), and the mixture was stirred at room temperature for 2 hours. The reaction product was subjected to rotary evaporation to remove the solvent, adjusted to pH 8 with saturated sodium bicarbonate aqueous solution, and extracted with dichloromethane three times (5 ml for each time). The organic phases were combined, washed with 10 ml saturated sodium chloride aqueous solution once, dried with anhydrous sodium sulfate, filtered, subjected to rotary evaporation, and separated by silica gel column chromatography (DCM/MeOH=20:1) to obtain the titled compound (10.5 mg, yellow solid).

$^1$H-NMR (400 MHz, DMSO-$d_6$) δ9.75 (br s, 1H), 8.65 (d, 1H, J=3.2 Hz), 8.02-7.94 (m, 3H), 7.82 (d, 1H, J=10.8 Hz), 7.43 (d, 1H, J=8.8 Hz), 3.09-3.02 (m, 4H), 2.84-2.83 (m, 4H), 2.31 (s, 3H), 1.34 (s, 6H).

MS (ESI): mass calcd. for $C_{24}H_{25}F_2N_7$ 449.50, m/z found 450.2[M+H]$^+$.

Example 2

N-(5-((4-ethylpiperazin-1-yl)methyl)pyridin-2-yl)-5-fluoro-4-(7-fluoro-2,3,3-trimethyl-3H-indol-5-yl)pyrimidine-2-amino

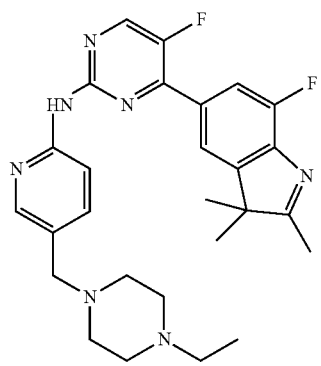 [SMILES: CCN1CCN(Cc2ccc(Nc3ncc(F)c(-c4cc(F)c5c(c4)C(C)(C)C(C)=N5)n3)nc2)CC1]

Step 1:
1-((6-bromopyridin-3-yl)methyl)-4-ethylpiperazine

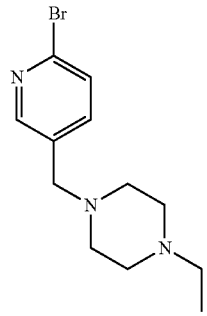 [SMILES: CCN1CCN(Cc2ccc(Br)nc2)CC1]

2-bromo-5-formylpyridine (1.5 g, 8.15 mmol), 1-ethylpiperazine (0.93 g, 8.15 mmol), and dichloromethane (15 mL) were added to the reaction flask, and then NaHB(OAc)3 (2.58 g, 12.23 mmol) was added in batches. Reaction was carried out at room temperature overnight. The reaction product was filtered, concentrated and separated by column chromatography (DCM/MeOH=100:1 to 10:1) to obtain the titled product (1.64 g, yellow oil).

MS (ESI): mass calcd. for $C_{12}H_{18}BrN_3$ 285.1, m/z found 286.1 [M+H]$^+$.

Step 2:
5-((4-ethylpiperazin-1-yl)methyl)pyridine-2-amino

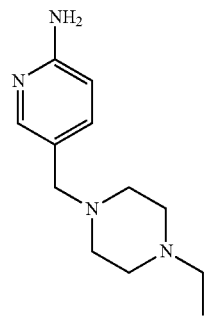 [SMILES: CCN1CCN(Cc2ccc(N)nc2)CC1]

A reaction flask was charged with 1-((6-bromopyridin-3-yl)methyl)-4-ethylpiperazine (2.84 g, 10 mmol) prepared in Step 1, 2-(dicyclohexylphosphino)biphenyl (700 mg, 2 mmol), Pd$_2$(dba)$_3$ (915 mg, 1 mmol) and toluene (30 mL), LHMDS (1 N) (20 ml, 20 mmol) was added under the protection of nitrogen gas. The mixture was heated to 80° C. and allowed to react overnight, then cooled to room temperature, filtered, concentrated and separated by column chromatography (DCM/MeOH=100:1-10:1) to give 1.52 g of the titled product (brown solid).

MS (ESI): mass calcd. for $C_{13}H_{21}N_3$ 220.2, m/z found 221.2 [M+H]$^+$.

Step 3: Preparation of
5-bromo-7-fluoro-2,3,3-trimethyl-3H-indole

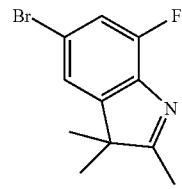

(4-Bromo-2-fluorobenzene)hydrazine (900.0 mg, 3.73 mmol), acetic acid (5 mL) and 3-methylbutan-2-one (353.3 mg, 4.09 mmol) were added to the reaction flask. The mixture was allowed to react under refluxing for 5 hours. The reaction product was subjected to rotary evaporation to remove solvent, added with 10 ml of water, and extracted with ethyl acetate three times (20 ml for each time). The organic phases were combined, washed with 25 ml of saturated sodium chloride aqueous solution once, dried with anhydrous sodium sulfate, filtered and subjected to rotary evaporation. The residue was separated by silica gel column chromatography (ethyl acetate:petroleum ether=1:50-1:25) to give 910 mg of the titled compound (yellow solid).

MS (ESI): m/z 258.0 [M+H]$^+$.

Step 4: Preparation of 7-fluoro-2,3,3-trimethyl-5-(4,4,5,5-tetramethyl-1,3,2-dioxaborolan-2-yl)-3H-indole

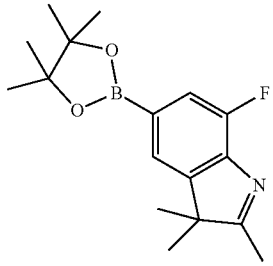 [SMILES: CC1=Nc2c(F)cc(B3OC(C)(C)C(C)(C)O3)cc2C1(C)C]

5-Bromo-7-fluoro-2,3,3-trimethyl-3H-indole (1.0 g, 3.91 mmol) prepared in Step 3, 4,4,4',4',5,5,5',5'-octamethyl-2,2'-bis(1,3,2-dioxaborolane) (1.09 g, 4.29 mmol), potassium acetate (770 mg, 7.82 mmol), dioxane (10 ml), Pd(dppf)Cl$_2$ (570 mg, 0.78 mmol) were added to a reaction flask, and heated to 90° C. under the protection of nitrogen gas to react overnight. The reaction product was cooled to room temperature, filtered, diluted with 10 ml of water, and extracted with ethyl acetate three times (20 ml for each time). The organic phases were combined, washed once with 25 ml of saturated salt solution, dried with sodium sulfate, filtered, subjected to rotary evaporation, and separated by silica gel column chromatography (EA:PE=1:100-1:20) to give 1.02 g of the titled compound (yellow oil).

MS (ESI): m/z 304.2 [M+H]$^+$.

Step 5: Preparation of 5-(2-chloro-5-fluoropyrimidin-4-yl)-7-fluoro-2,3,3-trimethyl-3H-indole

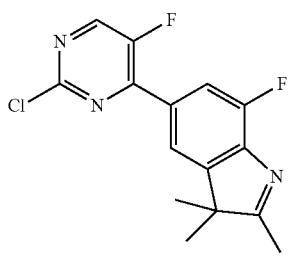 [SMILES: CC1=Nc2c(F)cc(-c3nc(Cl)ncc3F)cc2C1(C)C]

A microwave reaction flask was charged with 7-fluoro-2,3,3-trimethyl-5-(4,4,5,5-tetramethyl-1,3,2-dioxaborolan-2-yl)-3H-indole (1.0 g, 3.30 mmol) prepared in Step 4, 2,4-dichloro-5-fluoropyrimidine (610 mg, 3.63 mmol), potassium phosphate (1.39 g, 6.60 mmol), dioxane/water (8 mL/2 mL), and Pd(PPh$_3$)$_4$ (380 mg, 0.33 mmol). Microwave reaction was carried out at 130° C. under the protection of nitrogen gas for 1 hour. The reaction product was cooled to room temperature, filtered, added with 10 ml of water, extracted three times with dichloromethane (15 ml for each time). The organic phases were combined, washed once with 20 ml of saturated salt solution, dried with anhydrous sodium sulfate, filtered, concentrated and separated by silica gel column chromatography (EA:PE=1:50 to 1:10) to give the titled compound (290.0 mg, yellow solid).

MS (ESI): m/z 308.1 [M+H]$^+$.

Step 6: Preparation of N-(5-((4-ethylpiperazin-1-yl)methyl)pyridin-2-yl)-5-fluoro-4-(7-fluoro-2,3,3-trimethyl-3H-indol-5-yl)pyrimidine-2-amino

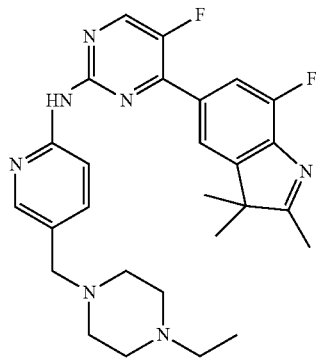

A reaction flask was charged with 5-(2-chloro-5-fluoropyrimidin-4-yl)-7-fluoro-2,3,3-trimethyl-3H-indole (290.0 mg, 0.94 mmol) prepared in step 5, 5-((4-ethylpiperazin-1-yl)methyl)pyridin-2-amino (228.6 mg, 1.04 mmol) prepared in Step 2, potassium phosphate (400.5 mg, 1.88 mmol), 10 ml of dioxane, Pd$_2$(dba)3 (86.4 mg, 0.09 mmol), and 4,5-bis(diphenylphosphino)-9,9-dimethylxanthene (109.2 mg, 0.19 mmol). Microwave reaction was carried out at 150° C. under the protection of nitrogen gas for 1 hour. The reaction product was cooled to room temperature, filtered, added with 10 ml of water, extracted three times with dichloromethane (10 ml for each time). The organic phases were combined, washed once with 30 ml of saturated salt solution, dried with anhydrous sodium sulfate, filtered, subjected to rotary evaporation to remove solvent, and separated by silica gel column chromatography (dichloromethane:methanol=30:1) to give the titled compound (140.3 mg, yellow solid).

$^1$H-NMR (400 MHz, CDCl$_3$) δ8.72 (s, 1H), 8.49 (d, 1H, J=3.2 Hz), 8.38 (d, 1H, J=8.4 Hz), 8.31 (s, 1H), 7.92 (s, 1H), 7.89 (s, 1H), 7.73 (d, 1H, J=8.4 Hz), 3.52 (s, 2H), 2.54-2.41 (m, 10H), 2.38 (s, 3H), 1.40 (s, 6H), 1.10 (t, 3H, J=7.2 Hz).

MS (ESI): m/z 492.2[M+H]$^+$.

Example 3

N-(5-((4-ethylpiperazin-1-yl)methylpyridin-2-yl)-5-fluoro-4-(7'-fluoro-2'-methylspiro[cyclopentane-1,3'-indol]-5'-yl)pyrimidine-2-amino

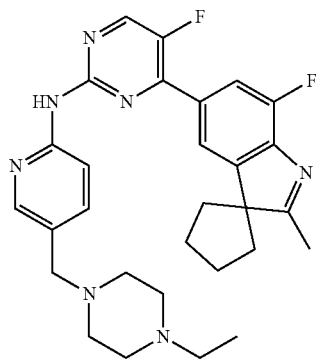 [SMILES: CCN1CCN(Cc2ccc(Nc3ncc(F)c(-c4cc(F)c5c(c4)C4(CCCC4)C(C)=N5)n3)nc2)CC1]

The titled compound was obtained by the steps similar to those of Example 2.

¹H-NMR (400 MHz, CDCl₃) δ9.75 (s, 1H), 8.54 (d, 1H, J=3.2 Hz), 8.38-8.37 (m, 2H), 7.94 (s, 1H), 7.87 (d, 1H, J=10.8 Hz), 7.68 (d, 1H, J=8.4 Hz), 3.49 (s, 2H), 2.99-2.39 (m, 10H), 2.37 (s, 3H), 2.14-2.08 (m, 6H), 1.87-1.84 (m, 2H), 1.06 (t, 3H, J=6.4 Hz).

MS (ESI): m/z 518.3[M+H]⁺.

Example 4

N-(5-((4-ethylpiperazin-1-yl)methyl)pyridin-2-yl)-5-fluoro-4-(7'-fluoro-2'-methylspiro[cyclobutane-1,3'-indol]-5'-yl)aminopyrimidine-2-amino

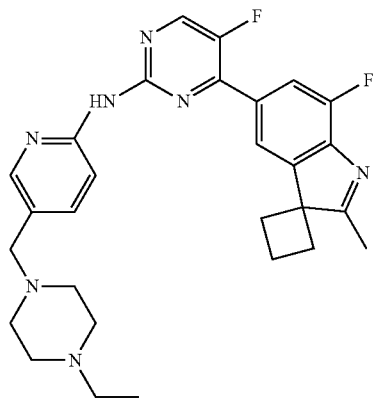 [SMILES: CCN1CCN(Cc2ccc(Nc3ncc(F)c(-c4cc(F)c5c(c4)C4(CCC4)C(C)=N5)n3)nc2)CC1]

The titled compound was obtained by the steps similar to those of Example 2.

¹H-NMR (400 MHz, CDCl₃) δ8.36-8.32 (m, 2H), 8.23 (s, 1H), 8.04 (s, 1H), 7.78-7.75 (m, 2H), 7.71 (d, 1H, J=8.4 Hz), 5.84-5.83 (m, 1H), 5.63-5.62 (m, 1H), 4.39-4.38 (m, 1H), 3.66-3.64 (m, 1H), 3.51 (s, 2H), 3.06-3.00 (m, 1H), 2.71-2.38 (m, 11H), 1.55 (s, 3H), 1.11 (t, 3H, J=7.2 Hz).

MS (ESI): m/z 504.3[M+H]⁺.

Example 5

4-(3-ethyl-7-fluoro-2,3-dimethyl-3H-indol-5-yl)-N-(5-((4-ethylpiperazin-1-yl)methyl)pyridin-2-yl)-5-fluoropyrimidine-2-amino

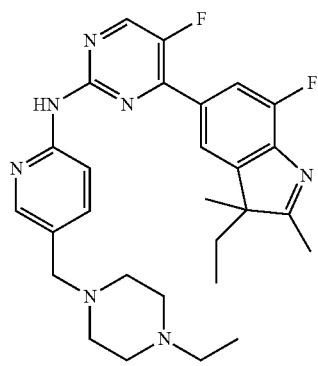 [SMILES: CCN1CCN(Cc2ccc(Nc3ncc(F)c(-c4cc(F)c5c(c4)C(C)(CC)C(C)=N5)n3)nc2)CC1]

The titled compound was obtained by the steps similar to those of Example 2.

¹H-NMR (400 MHz, CDCl₃) δ8.71 (s, 1H), 8.49 (d, 1H, J=3.6 Hz), 8.38 (d, 1H, J=8.4 Hz), 8.31 (s, 1H), 7.94 (d, 1H, J=11.2 Hz), 7.86 (s, 1H), 7.72 (dd, 1H, J=8.0, 1.2 Hz), 3.52 (s, 2H), 2.53-2.41 (m, 10H), 2.34 (s, 3H), 2.06-1.93 (m, 1H), 1.91-1.84 (m, 1H), 1.39 (s, 3H), 1.09 (t, 3H, J=7.2 Hz), 0.50 (t, 3H, J=7.2 Hz).

MS (ESI): m/z 506.3[M+H]⁺.

Example 6

5-fluoro-4-(7'-fluoro-2'-methylspiro[cyclopentane-1,3'-indol]-5'-yl)-N-(5-(piperazin-1-yl)pyridin-2-yl) pyrimidine-2-amino

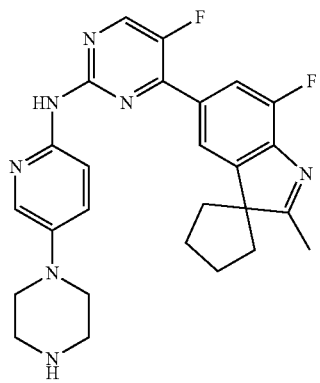 [SMILES: CC1=Nc2c(F)cc(-c3nc(Nc4ccc(N5CCNCC5)cn4)ncc3F)cc2C12CCCC2]

The titled compound was obtained by the steps similar to those of Example 1.

¹H-NMR (400 MHz, CDCl₃) δ8.67 (br s, 1H), 8.44 (d, 1H, J=3.6 Hz), 8.29 (d, 1H, J=9.2 Hz), 8.11 (d, 1H, J=2.4 Hz), 7.95 (s, 1H), 7.89 (d, 1H, J=10.8 Hz), 7.36 (dd, 1H, J=9.2, 2.8 Hz), 3.12-3.06 (m, 8H), 2.39 (s, 3H), 2.16-2.10 (m, 6H), 1.89-1.86 (m, 2H).

MS (ESI): m/z 476.2[M+H]⁺.

Example 7

4-(3-ethyl-7-fluoro-2,3-dimethyl-3H-indol-5-yl)-5-fluoro-N-(5-(piperazin-1-yl)pyridin-2-yl)pyrimidine-2-amino

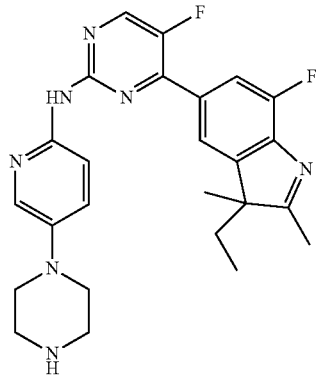 [SMILES: CCC1(C)C(C)=Nc2c(F)cc(-c3nc(Nc4ccc(N5CCNCC5)cn4)ncc3F)cc21]

The titled compound was obtained by the steps similar to those of Example 1.

¹H-NMR (400 MHz, CDCl₃) δ9.33 (br s, 1H), 8.46 (d, 1H, J=3.6 Hz), 8.28 (d, 1H, J=8.8 Hz), 8.16 (d, 1H, J=2.4 Hz), 7.90 (d, 1H, J=10.8 Hz), 7.82 (s, 1H), 7.35 (dd, 1H, J=8.8 Hz, 2.8 Hz), 3.10-3.03 (m, 8H), 2.31 (s, 3H), 2.03-1.80 (m, 3H), 1.36 (s, 3H), 0.47 (t, 6H, J=7.6 Hz).

MS (ESI): m/z 464.2[M+H]⁺.

Example 8

N-(5-((4-ethylpiperazin-1-yl)methyl)pyridin-2-yl)-4-(7'-fluoro-2'-methylspiro [cyclopentane-1,3'-indol]-5'-yl)pyrimidine-2-amino

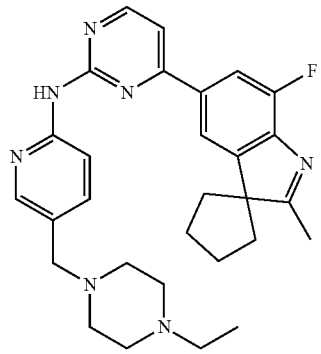 [SMILES: CCN1CCN(Cc2ccc(Nc3nccc(-c4cc(F)c5c(c4)C4(CCCC4)C(C)=N5)n3)nc2)CC1]

The titled compound was obtained by the steps similar to those of Example 2.

¹H-NMR (400 MHz, CDCl₃) δ8.83 (s, 1H), 8.61 (d, 1H, J=5.2 Hz), 8.49 (d, 1H, J=8.8 Hz), 8.32 (d, 1H, J=1.2 Hz), 7.91 (d, 1H, J=1.2 Hz), 7.78 (d, 1H, J=10.8 Hz), 7.78 (dd, 1H, J=8.4, 1.6 Hz), 7.21 (d, 1H, J=5.2 Hz), 3.52 (s, 2H), 2.54-2.41 (m, 10H), 2.38 (s, 3H), 2.19-2.08 (m, 6H), 1.90-1.87 (m, 2H), 1.10 (t, 3H, J=6.8 Hz).

MS (ESI): m/z 500.3[M+H]⁺.

Example 9

N-(5-((4-ethylpiperazin-1-yl)methyl)pyridin-2-yl)-5-fluoro-4-(2'-methylspiro [cyclopentane-1,3'-indol]-5'-yl)pyrimidine-2-amino

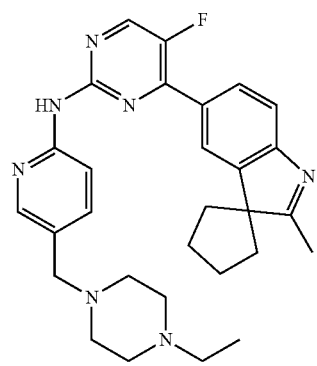 [SMILES: CCN1CCN(Cc2ccc(Nc3ncc(F)c(-c4ccc5c(c4)C4(CCCC4)C(C)=N5)n3)nc2)CC1]

The titled compound was obtained by the steps similar to those of Example 2.

¹H-NMR (400 MHz, CDCl₃) δ8.73 (br s, 1H), 8.47 (d, 1H, J=3.6 Hz), 8.43 (d, 1H, J=8.4 Hz), 8.30 (s, 1H), 8.15-8.13 (m, 2H), 7.70-7.64 (m, 2H), 3.52 (s, 2H), 2.53-2.37 (m, 10H), 2.31 (s, 3H), 2.21-2.06 (m, 6H), 1.89-1.86 (m, 2H), 1.10 (t, 3H, J=7.2 Hz).

MS (ESI): m/z 500.3[M+H]⁺.

Example 10

4-(3,3-diethyl-7-fluoro-2-methyl-3H-indol-5-yl)-N-(5-((4-ethylpiperidin-1-yl)methyl)pyridin-2-yl)-5-fluoropyrimidine-2-amino

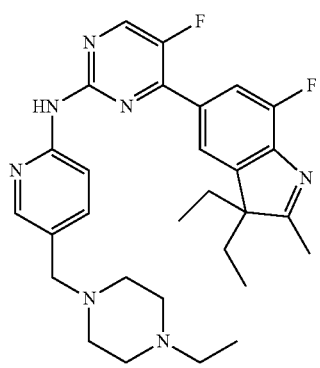 [SMILES: CCN1CCN(Cc2ccc(Nc3ncc(F)c(-c4cc(F)c5c(c4)C(CC)(CC)C(C)=N5)n3)nc2)CC1]

The titled compound was obtained by the steps similar to those of Example 2.

¹H-NMR (400 MHz, CDCl₃) δ9.19 (br s, 1H), 8.53 (s, 1H), 8.39-8.34 (m, 2H), 7.95 (d, 1H, J=11.2 Hz), 7.83 (s, 1H), 7.72 (d, 1H, J=8.0 Hz), 3.51 (s, 2H), 2.52-2.41 (m, 10H), 2.31 (s, 3H), 2.06-2.01 (m, 2H), 1.90-1.85 (m, 2H), 1.08 (t, 3H, J=6.8 Hz), 0.46 (t, 6H, J=6.8 Hz).

MS (ESI): m/z 520.3[M+H]⁺.

Example 11

4-(3-ethyl-7-fluoro-2,3-dimethyl-3H-indol-5-yl)-5-fluoro-N-(5-(piperidin-1-yl) pyridin-2-yl)pyrimidine-2-amino

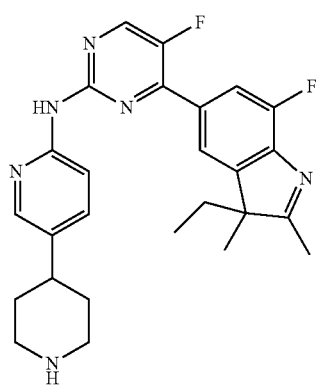 [SMILES: CCC1(C)C(C)=Nc2c(F)cc(-c3nc(Nc4ccc(C5CCNCC5)cn4)ncc3F)cc21]

Step 1: 6-Nitro-3',6'-dihydro-[3,4'-bipyridine]-1'(2'H)-carboxylic acid t-butyl ester

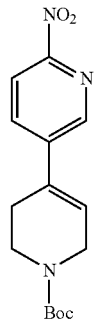

A reaction flask was charged with 5-bromo-2-nitropyridine (20.3 g, 0.1 mol), 4-(4,4,5,5-tetramethyl-1,3,2-dioxaborolan-2-yl)-5,6-dihydropyridine-1(2H)-carboxylic acid t-butyl ester (31 g, 0.1 mol), dioxane/water (250 mL/30 mL), cesium carbonate (66 g, 0.2 mol) and Pd(dppf)Cl$_2$ (7.33 g, 0.01 mol), and protected by nitrogen gas. The mixture was heated to 85° C. for 12 hours. The reaction product was cooled to room temperature, concentrated and separated by column chromatography (PE/EA=1:1 to DCM/MeOH=20:1) to give the title product (11 g, yellow solid).

MS (ESI): mass calcd. for $C_{15}H_{19}N_3O_4$ 305.1, m/z found 306.1 [M+H]$^+$.

Step 2: 4-(6-Aminopyridin-3-yl)piperidine-1-carboxylic acid t-butyl ester

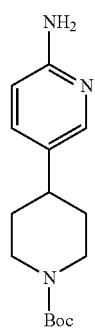

A reaction flask was charged with 6-nitro-3',6'-dihydro-[3,4'-bipyridine]-1'(2'H)-carboxylic acid t-butyl ester (0.9 g, 3.0 mmol) prepared in Step 1, ethyl acetate/methanol (10 mL/10 mL) and Pd/C (0.1 g). Hydrogen was introduced thereinto and the reaction was carried out at room temperature for 2 hours. The reaction product was filtered and concentrated to obtain the titled product (790 mg, off-white solid).

MS (ESI): mass calcd. for $C_{15}H_{23}N_3O_2$ 277.2, m/z found 278.2 [M+H]$^+$.

4-(3-Ethyl-7-fluoro-2,3-dimethyl-3H-indol-5-yl)-5-fluoro-N-(5-(piperidin-1-yl)pyridin-2-yl)pyrimidine-2-amino

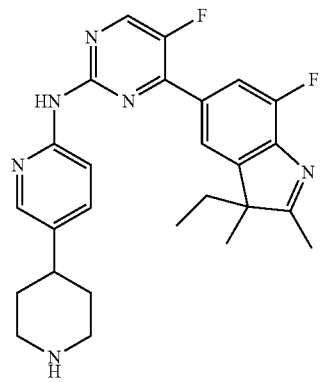 [SMILES: CCC1(C)C(C)=Nc2c(F)cc(-c3nc(Nc4ccc(C5CCNCC5)cn4)ncc3F)cc21]

Other steps were carried out according to the steps similar to Steps 3-7 of Example 1 to obtain the titled compound of this example.

$^1$H-NMR (400 MHz, CDCl$_3$) δ8.61 (br s, 1H), 8.46 (d, 1H, J=3.6 Hz), 8.34 (d, 1H, J=8.8 Hz), 8.26 (d, 1H, J=1.6 Hz), 7.93 (d, 1H, J=11.2 Hz), 7.64 (d, 1H, J=8.0 Hz), 7.86 (s, 1H), 7.61 (dd, 1H, J=8.4 Hz, 2.0 Hz), 3.24-3.21 (m, 2H), 2.77 (t, 1H, J=10.8 Hz), 2.64-2.61 (m, 1H), 2.34 (s, 3H), 2.06-1.91 (m, 4H), 1.89-1.84 (m, 3H), 1.72-1.63 (m, 2H), 1.39 (s, 3H), 0.50 (t, 1H, J=7.2 Hz).

MS (ESI): m/z found 463.3[M+H]$^+$.

Example 12

N-(5-(1-ethylpiperidin-4-yl)pyridin-2-yl)-5-fluoro-4-(7'-fluoro-2'-methylspiro[cyclopentane-1,3'-indol]-5'-yl)pyrimidine-2-amino

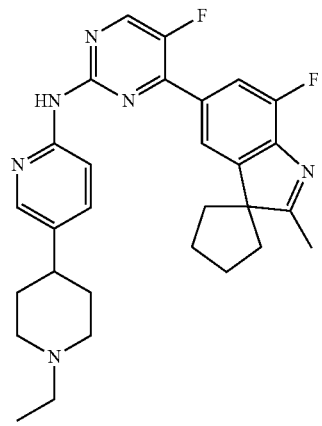 [SMILES: CCN1CCC(c2ccc(Nc3ncc(F)c(-c4cc(F)c5c(c4)C4(CCCC4)C(C)=N5)n3)nc2)CC1]

5-fluoro-4-(7'-fluoro-2'-methylspiro[cyclopentane-1,
3'-indol]-5'-yl)-N-(5-(piperidin-4-yl)pyridin-2-yl)
pyrimidine-2-amino

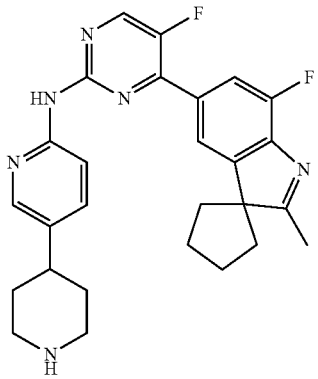

This intermediate was obtained according to a step similar to that of Example 11.

N-(5-(1-ethylpiperidin-4-yl)pyridin-2-yl)-5-fluoro-4-
(7'-fluoro-2'-methylspiro [cyclopentane-1,3'-indol]-
5'-yl)pyrimidine-2-amino

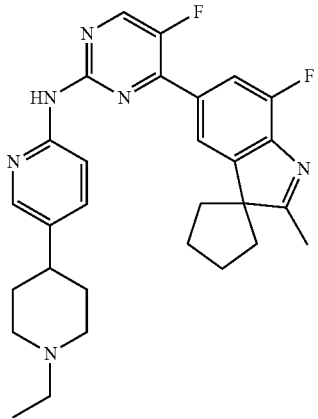 [SMILES: CCN1CCC(c2ccc(Nc3ncc(F)c(-c4cc(F)c5c(c4)C4(CCCC4)C(C)=N5)n3)nc2)CC1]

A reaction flask was charged with 5-fluoro-4-(7'-fluoro-2'-methylspiro [cyclopentane-1,3'-indol]-5'-yl)-N-(5-(piperidin-4-yl)pyridin-2-yl)pyrimidine-2-amino 50 mg (0.1 mmol) prepared in the above step, acetaldehyde 26 mg (0.6 mmol) and dichloromethane 5 ml, and reaction was carried out at room temperature for 0.5 hour. Then sodium triethylborohydride 60 mg (0.28 mmol) was added, and reaction was carried out at room temperature for 2 hours. The reaction solution was added with 20 ml of saturated sodium carbonate aqueous solution, and then extracted three times with dichloromethane (10 mL for each time). The organic phases were combined, washed once with saturated salt solution, dried with anhydrous sodium sulfate, filtered, concentrated under reduced pressure, and separated by silica gel column chromatography (PE/EA=5:1) to give the titled compound (11 mg, yield 22%).

$^1$H-NMR (400 MHz, CDCl$_3$) δ8.45 (d, 1H, J=3.6 Hz), 8.38 (s, 1H), 8.33 (d, 1H, J=8.8 Hz), 8.25 (s, 1H), 7.97 (s, 1H), 7.90 (d, 1H, J=11.2 Hz), 7.62 (dd, 1H, J=8.8, 2.0 Hz), 3.14-3.11 (m, 2H), 2.55-2.46 (m, 3H), 2.40 (s, 3H), 2.18-2.03 (m, 8H), 1.90-1.82 (m, 6H), 1.15 (t, 3H, J=7.2 Hz).

MS (ESI): m/z 503.3[M+H]$^+$.

Example 13

5-Fluoro-4-(7'-fluoro-2'-methylspiro[cyclopentane-1,
3'-indol]-5'-yl)-N-(5-(piperidin-4-yl)pyridin-2-yl)
pyrimidine-2-amino

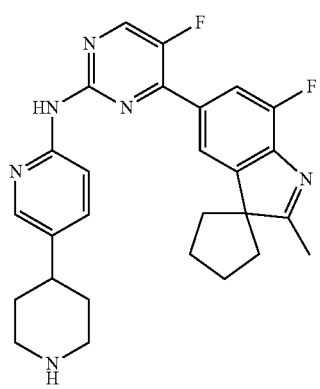 [SMILES: CC1=Nc2c(F)cc(-c3nc(Nc4ccc(C5CCNCC5)cn4)ncc3F)cc2C12CCCC2]

The titled compound was obtained by the steps similar to those of Example 11.

$^1$H-NMR (400 MHz, CDCl$_3$) δ9.14 (br s, 1H), 8.48 (d, 1H, J=3.2 Hz), 8.34-8.30 (m, 2H), 7.96 (s, 1H), 7.89 (d, 1H, J=10.8 Hz), 7.58 (d, 1H, J=8.4 Hz), 3.22-3.19 (m, 2H), 2.76 (t, 2H, J=11.6 Hz), 2.66-2.60 (m, 1H), 2.38 (s, 3H), 2.16-2.02 (m, 6H), 1.88-1.83 (m, 4H), 1.69-1.61 (m, 2H).

MS (ESI): m/z 475.3[M+H]$^+$.

Example 14

5-fluoro-4-(2'-methylspiro[cyclopentane-1,3'-indol]-
5'-yl)-N-(5-(piperazin-1-yl)pyridin-2-yl)pyrimidine-
2-amino

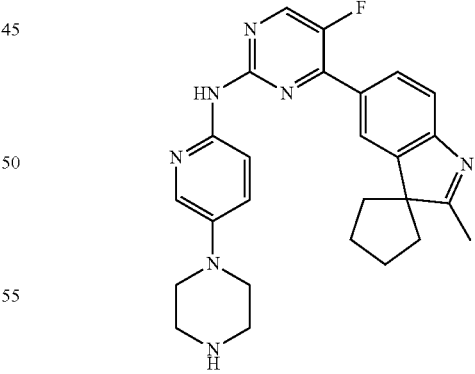

The titled compound was obtained by the steps similar to those of Example 11.

$^1$H-NMR (400 MHz, CDCl$_3$) δ9.28 (br s, 1H), 8.43 (d, 1H, J=3.6 Hz), 8.33 (d, 1H, J=9.2 Hz), 8.16-8.09 (m, 3H), 7.63 (d, 1H, J=8.0 Hz), 7.32 (dd, 1H, J=9.2 Hz, 2.8 Hz), 3.08-3.06 (m, 4H), 3.03-3.02 (m, 4H), 2.34 (s, 3H), 2.29-2.04 (m, 7H), 1.86-1.83 (m, 2H).

MS (ESI): m/z 458.3[M+H]$^+$.

Example 15

5-fluoro-4-(2'-methylspiro[cyclopentane-1,3'-indol]-5'-yl)-N-(5-(piperidin-4-yl)pyridin-2-yl)pyrimidine-2-amino

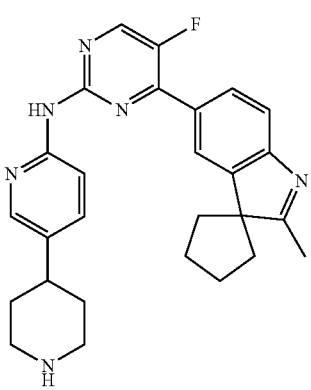 [SMILES: CC1=Nc2ccc(-c3nc(Nc4ccc(C5CCNCC5)cn4)ncc3F)cc2C12CCCC2]

The titled compound was obtained by the steps similar to those of Example 11.

$^1$H-NMR (400 MHz, CDCl$_3$) δ 8.99 (br s, 1H), 8.46 (d, 1H, J=3.6 Hz), 8.39 (d, 1H, J=8.4 Hz), 8.29 (d, 1H, J=1.6 Hz), 8.15-8.11 (m, 2H), 7.65 (d, 1H, J=8.0 Hz), 7.58 (dd, 1H, J=8.8 Hz, 2.0 Hz), 3.22-3.19 (m, 2H), 2.76 (t, 2H, J=10.4 Hz), 2.65-2.59 (m, 1H), 2.36 (s, 3H), 2.18-2.05 (m, 7H), 1.88-1.83 (m, 4H), 1.70-1.60 (m, 2H).

MS (ESI): m/z 457.3[M+H]$^+$.

Example 16

4-(3,3-diethyl-7-fluoro-2-methyl-3H-indol-5-yl)-5-fluoro-N-(5-(4-methylpiperazin-1-yl)pyridin-2-yl)pyrimidine-2-amino

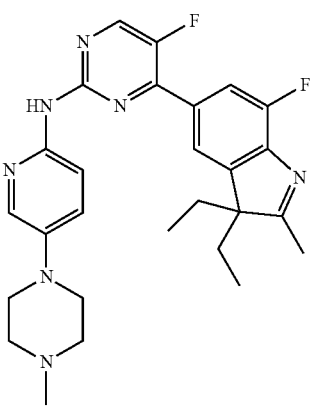 [SMILES: CCC1(CC)C(C)=Nc2c(F)cc(-c3nc(Nc4ccc(N5CCN(C)CC5)cn4)ncc3F)cc21]

Step 1: Preparation of 5-bromo-3,3-diethyl-7-fluoro-2-methyl-3H-indole

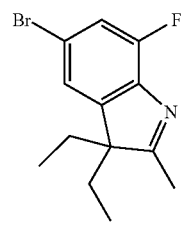

10 ml of acetic acid, 5.0 g (20.75 mmol) of (4-bromo-2-fluorophenyl)hydrazine hydrochloride and 2.35 g (20.75 mmol) of 3-ethylpentan-2-one were added to a reaction flask, and the mixture was allowed to react under refluxing for 5 hours. The reaction product was subjected to rotary evaporation to remove solvent, added with 50 ml of water, and extracted with ethyl acetate three times (50 ml for each time). The organic phases were combined, washed once with 50 ml of salt solution, dried with sodium sulfate, filtered, subjected to rotary evaporation, and separated by column chromatography (EA:PE=1:100-1:10) to obtain the titled compound (2.5 g, yellow oil), yield 87.1%.

MS (ESI): m/z 286.1 [M+H]$^+$.

Step 2: Preparation of 3,3-Diethyl-7-fluoro-2-methyl-5-(4,4,5,5-tetramethyl-1,3,2-dioxaborolan-2-yl)-3H-indole

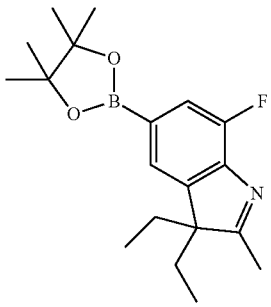 [SMILES: CCC1(CC)C(C)=Nc2c(F)cc(B3OC(C)(C)C(C)(C)O3)cc21]

2.0 g (7.07 mol) of 5-bromo-3,3-diethyl-7-fluoro-2-methyl-3H-indole prepared in Step 1, 1.97 g (7.77 mmol) of 4,4,4',4',5,5,5',5'-octamethyl-2,2'-bis(1,3,2-dioxaborolane), 1.38 g (1.41 mmol) of potassium acetate, 10 ml of 1,4-dioxane and 1.03 g (1.41 mmol) of Pd(dppf)Cl$_2$ were added to the reaction flask, and the mixture was heated to 90° C. under the protection of nitrogen gas to conduct reaction overnight. The reaction product was cooled to room temperature, filtered, diluted with 10 mL of water and extracted three times with ethyl acetate (10 mL for each time). The organic phases were combined, washed once with 15 ml of salt solution, dried with anhydrous sodium sulfate, filtered, concentrated and separated by silica gel column chromatography (EA:PE=1:50 to 1:10) to give the titled compound (2.0 g, yellow oil), yield 86.96%.

MS (ESI): m/z 332.3 [M+H]$^+$.

Step 3: 5-(2-Chloro-5-fluoropyrimidin-4-yl)-3,3-diethyl-7-fluoro-2-methyl-3H-indole

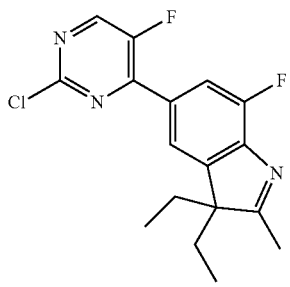 [SMILES: CCC1(CC)C(C)=Nc2c(F)cc(-c3nc(Cl)ncc3F)cc21]

A reaction flask was charged with 2.0 g (6.05 mmol) of 3,3-diethyl-7-fluoro-2-methyl-5-(4,4,5,5-tetramethyl-1,3,2-dioxaborolan-2-yl)-3H-indole prepared in Step 2, 1.10 g (6.65 mmol) of 2,4-dichloro-5-fluoropyrimidine, 2.56 g (12.1 mmol) of potassium phosphate, 20 mL/5 mL of dioxane/water, 0.69 g (0.61 mmol) of Pd (PPh$_3$)$_4$, and the mixture was heated to 120° C. under the protection of nitrogen gas and allowed to react for 2 hours. The reaction product was cooled to room temperature, filtered, diluted with 10 mL of water and extracted three times with 50 mL of dichloromethane. The organic phases were combined, washed once with 20 ml of salt solution, dried with anhydrous sodium sulfate, filtered, concentrated under reduced pressure, and separated by silica gel column chromatography (EA:PE=1:100-1:10) to give the titled compound (1.2 g, yellow solid), yield 59.4%.
MS (ESI): m/z 336.1 [M+H]$^+$.

Step 4: Preparation of 4-(6-((4-(3,3-diethyl-7-fluoro-2-methyl-3H-indol-5-yl)-5-fluoropyrimidin-2-yl)amino)pyridin-3-yl)piperazine-1-carboxylic acid t-butyl ester

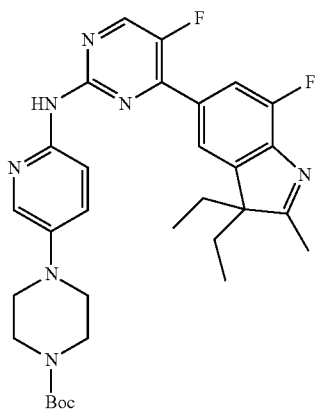 [SMILES: CCC1(CC)C(C)=Nc2c(F)cc(-c3nc(Nc4ccc(N5CCN(C(=O)OC(C)(C)C)CC5)cn4)ncc3F)cc21]

A reaction flask was charged with 400.0 mg (1.19 mmol) of 5-(2-chloro-5-fluoropyrimidin-4-yl)-3,3-diethyl-7-fluoro-2-methyl-3H-indole prepared in Step 3, 331.9 mg (1.19 mmol) of t-butyl 4-(6-aminopyridin-3-yl)piperazine-1-carboxylate prepared according to Steps 1-2 of Example 1, 776.2 mg (2.38 mmol) of cesium carbonate, 10 ml of 1,4-dioxane, 109.5 mg (0.12 mmol) of Pd$_2$(dba)3, and 69.0 mg (0.12 mmol) of 4,5-bis (diphenylphosphino)-9,9-dimethylxanthene, and protected by nitrogen. The mixture was allowed to conduct microwave reaction at 130° C. for 1 hour. The reaction product is cooled to room temperature, filtered, diluted with 10 ml of water, extracted three times with 10 ml of dichloromethane. The organic phases were combined, washed once with 30 ml of salt solution, dried with anhydrous sodium sulfate, filtered, concentrated and separated by TLC to obtain the titled compound (253.1 mg, yellow solid), yield 36.74%.
MS (ESI): m/z 578.3 [M+H]$^+$ Step 5: 4-(3,3-diethyl-7-fluoro-2-methyl-3H-indol-5-yl)-5-fluoro-N-(5-(piperazin-1-yl)pyridin-2-yl)pyrimidine-2-amino

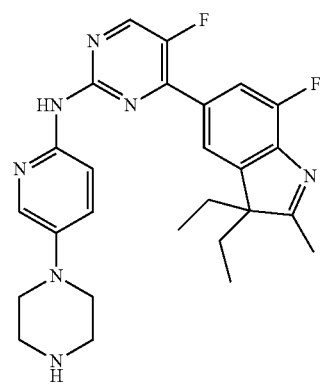 [SMILES: CCC1(CC)C(C)=Nc2c(F)cc(-c3nc(Nc4ccc(N5CCNCC5)cn4)ncc3F)cc21]

A reaction flask was charged with 4-(6-((4-(3,3-diethyl-7-fluoro-2-methyl-3H-indol-5-yl)-5-fluoropyrimidin-2-yl)amino)pyridin-3-yl)piperazine-1-carboxylic acid t-butyl ester 250.0 mg (0.43 mmol) prepared in step 4, dichloromethane 4 mL, and TFA 1 ml. The mixture was stirred at room temperature for 2 hours, and the solvent was removed. The residue was adjusted to pH8 with 5 ml of saturated sodium bicarbonate solution, and extracted three times with dichloromethane (5 ml for each time). The organic phases were combined, washed once with 10 ml of saturated salt solution, dried with anhydrous sodium sulfate, filtered, concentrated under reduced pressure and separated by TLC to give the titled compound (201.2 mg, yellow solid), yield 97.6%.
MS (ESI): m/z 478.3 [M+H]$^+$.

Step 6: 4-(3,3-diethyl-7-fluoro-2-methyl-3H-indol-5-yl)-5-fluoro-N-(5-(4-methylpiperazin-1-yl)pyridin-2-yl)pyrimidine-2-amino

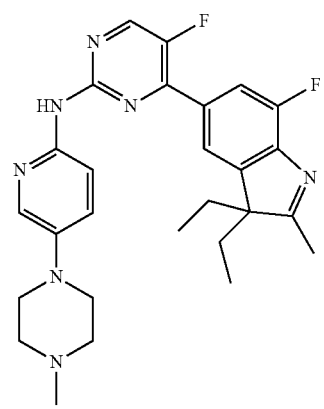 [SMILES: CCC1(CC)C(C)=Nc2c(F)cc(-c3nc(Nc4ccc(N5CCN(C)CC5)cn4)ncc3F)cc21]

A reaction flask was charged with 50.0 mg (0.10 mmol) of 4-(3,3-diethyl-7-fluoro-2-methyl-3H-indol-5-yl)-5-fluoro-N-(5-(piperazin-1-yl)pyridin-2-yl)pyrimidine-2-amino, 30.8 mg (1.0 mmol) of formaldehyde, 2 ml of 1-ethyl-(3-dimethylaminopropyl) carbodiimide, 65.3 mg (0.3 mmol) of sodium triethylborohydride, and the mixture was allowed to react overnight. 2 ml of methanol was added to quench the reaction, and the reaction product was extracted three times with dichloromethane (5 ml for each time). The organic phase was washed once with 10 ml of saturated salt solution, dried with anhydrous sodium sulfate, filtered, concentrated and separated by TLC to obtain the titled compound (20.3 mg, yellow solid), yield 39.4%.

$^1$H-NMR (400 MHz, CDCl$_3$) δ9.57 (br s, 1H), 8.47 (d, 1H, J=3.2 Hz), 8.28 (d, 1H, J=8.8 Hz), 8.18 (d, 1H, J=2.0 Hz), 7.91 (d, 1H, J=11.2 Hz), 7.78 (s, 1H), 7.33 (d, 1H, J=8.8 Hz), 3.16-3.15 (m, 4H), 2.58-2.57 (m, 4H), 2.33 (s, 3H), 2.26 (s, 3H), 2.04-1.95 (m, 2H), 1.85-1.78 (m, 7H), 0.43 (t, 6H, J=7.2 Hz).

MS (ESI): m/z 492.3[M+H]$^+$.

Example 17

5-Fluoro-4-(7'-fluoro-2'-methylspiro[cyclopentane-1,3'-indol]-5'-yl)-N-(5-(1-methylpiperidin-4-yl)pyridin-2-yl)pyrimidine-2-amino

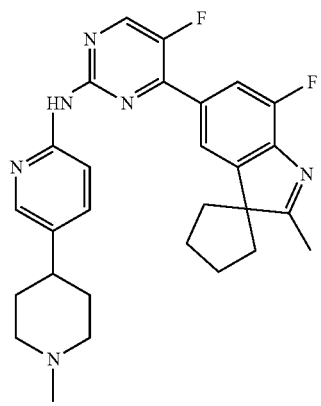

The intermediate 5'-(2-chloro-5-fluoropyrimidin-4-yl)-7'-fluoro-2'-methylspiro [cyclopentane-1,3'-indole] was obtained by the steps similar to those of Example 1.

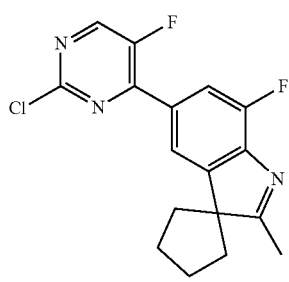 [SMILES: CC1=Nc2c(F)cc(-c3nc(Cl)ncc3F)cc2C12CCCC2]

Step 1: 1'-Methyl-6-nitro-1',2',3',6'-tetrahydro-3,4'-bipyridine

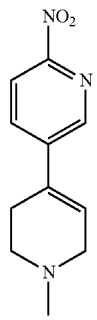 [SMILES: CN1CC=C(c2ccc([N+](=O)[O-])nc2)CC1]

A reaction flask was charged with 5-bromo-2-nitropyridine (20.3 g, 0.1 mol), 1-methyl-4-(4,4,5,5-tetramethyl-1,3,2-dioxaborolan-2-yl)-1,2,3,6-tetrahydropyridine (22.3 g, 0.1 mol), dioxane/water (250 mL/30 mL), cesium carbonate (66 g, 0.2 mol) and Pd(dppf)Cl$_2$ (7.33 g, 0.01 mol). The mixture was stirred to react at 85° C. under the protection of nitrogen gas for 12 hours. The reaction product was cooled to room temperature, concentrated and separated by column chromatography (PE/EA=1:1 to DCM/MeOH=20:1) to give the titled product (5.7 g, white solid).

MS (ESI): mass calcd. for C$_{11}$H$_{13}$N$_3$O$_2$ 219.1, m/z found 220.1 [M+H]$^+$.

Step 2: 5-(1-Methylpiperidin-4-yl)pyridin-2-amino

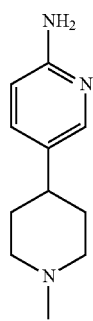

A reaction flask was charged with 1'-methyl-6-nitro-1',2',3',6'-tetrahydro-3,4'-bipyridine (657 mg, 3.0 mmol) prepared in Step 1, ethyl acetate/methanol (10 mL/10 mL), and Pd/C (0.1 g). Hydrogen gas was introduced into the mixture, and the mixture was stirred to react for 2 hours, filtered and concentrated to give the titled product (550 mg, white solid).

MS (ESI): mass calcd. for C$_{11}$H$_{17}$N$_3$ 191.1, m/z found 192.2 [M+H]$^+$.

Step 3: 5-Fluoro-4-(7'-fluoro-2'-methylspiro[cyclopentane-1,3'-indol]-5'-yl)-N-(5-(1-methylpiperidin-4-yl)pyridin-2-yl)pyrimidine-2-amino

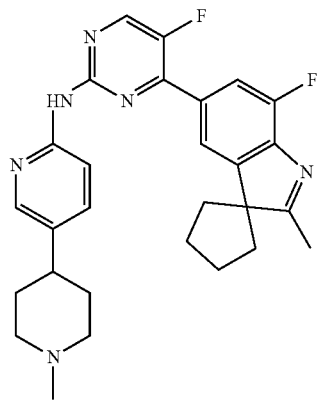 [SMILES: CC1=Nc2c(F)cc(-c3nc(Nc4ccc(C5CCN(C)CC5)cn4)ncc3F)cc2C12CCCC2]

A reaction flask was charged with the intermediate 5'-(2-chloro-5-fluoropyrimidin-4-yl)-7'-fluoro-2'-methylspiro[cyclopentane-1,3'-indole] (150.0 mg, 0.45 mmol), 5-(1-methylpiperidin-4-yl)pyridin-2-amino (86.6 mg, 0.45 mmol) prepared in Step 2, cesium carbonate (293.2 mg, 0.9 mmol), dioxane (3 ml), Pd$_2$(dba)$_3$ (44.7 mg, 0.05 mmol), 4,5-bis(diphenylphosphino)-9,9-dimethylxanthene (30.4 mg, 0.05 mmol). The mixture was heated to 150° C. under the protection of nitrogen gas to conduct microwave reaction for 1 hour. The reaction product was cooled to room temperature, filtered, added with 10 ml of water, and extracted three times with dichloromethane (10 ml for each time). The combined organic phase was washed once with 30 ml of saturated sodium chloride aqueous solution, dried with anhydrous sodium sulfate, filtered, concentrated and separated by silica gel column chromatography (dichloromethane/methanol=50:1) to give the titled compound (51.1 mg, yellow solid).

$^1$H-NMR (400 MHz, CDCl$_3$) δ9.38 (br s, 1H), 8.49 (d, 1H, J=3.2 Hz), 8.34-8.33 (m, 2H), 7.96 (s, 1H), 7.88 (d, 1H, J=11.2 Hz), 7.58 (dd, 1H, J=8.8 Hz, 1.6 Hz), 3.01-2.98 (m, 2H), 2.52-2.44 (m, 1H), 2.38 (s, 3H), 2.34 (s, 3H), 2.25-2.04 (m, 8H), 1.87-1.76 (m, 6H).

MS (ESI): m/z 489.3[M+H]$^+$.

Example 18

4-(3-ethyl-7-fluoro-2,3-dimethyl-3H-indol-5-yl)-5-fluoro-N-(5-(4-methylpiperazin-1-yl)pyridin-2-yl)pyrimidine-2-amino

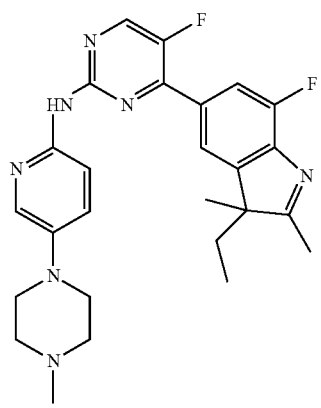 [SMILES: CCC1(C)C(C)=Nc2c(F)cc(-c3nc(Nc4ccc(N5CCN(C)CC5)cn4)ncc3F)cc21]

The titled compound was obtained by the steps similar to those of Example 16.

$^1$H-NMR (400 MHz, CDCl$_3$) δ9.48 (br s, 1H), 8.47 (d, 1H, J=3.2 Hz), 8.28 (d, 1H, J=9.2 Hz), 8.17 (s, 1H), 7.90 (d, 1H, J=10.8 Hz), 7.82 (s, 1H), 7.34 (d, 1H, J=8.4 Hz), 3.17-3.16 (m, 4H), 2.59-2.58 (m, 4H), 2.35 (s, 3H), 2.31 (s, 3H), 2.01-1.96 (m, 1H), 1.87-1.82 (m, 1H), 1.35 (s, 3H), 0.47 (t, 3H, J=7.2 Hz).

MS (ESI): m/z 478.3[M+H]$^+$.

Example 19

4-(3-ethyl-7-fluoro-2,3-dimethyl-3H-indol-5-yl)-N-(5-(4-ethylpiperazin-1-yl) pyridin-2-yl)-5-fluoropyrimidine-2-amino

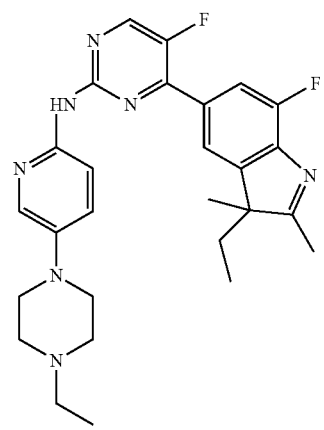 [SMILES: CCN1CCN(c2ccc(Nc3ncc(F)c(-c4cc(F)c5c(c4)C(C)(CC)C(C)=N5)n3)nc2)CC1]

Step 1: Preparation of
1-ethyl-4-(6-nitropyridin-3-yl) piperazine

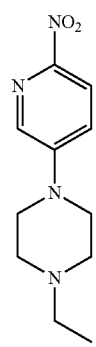

4.00 g (19.7 mmol) of 5-bromo-2-nitropyridine, 3.40 g (2.98 mmol) of 1-ethylpiperazine, 4.10 g (29.6 mmol) of potassium carbonate, 0.4 g (1.2 mmol) of tetrabutylammonium iodide, and 40 mL of DMSO were added to a reaction flask, and reacted at 80° C. for 16 hours. The reaction solution was then poured into ice-water and extracted three times with dichloromethane (20 ml for each time). The organic phases were combined, dried with anhydrous sodium sulfate, filtered, concentrated and separated by column chromatography (DCM/MeOH=100:1-10:1) to give 3.59 g of yellow solid, yield 56.1%.

MS (ESI): m/z 237.2 [M+H]$^+$.

Step 2: Preparation of 5-(4-ethylpiperazin-1-yl)pyridin-2-amino

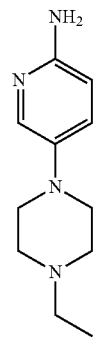

650 mg (2.13 mmol) of 1-ethyl-4-(6-nitropyridin-3-yl) piperazine prepared in Step 1 was dissolved in 45 ml of methanol, 10% palladium carbon (250 mg, cat) was added, the atmosphere was replaced three times with hydrogen gas, and the reaction was carried out at room temperature for 12 hours in the atmosphere of hydrogen gas under 3 atmos. After the reaction stopped, the reaction product was filtered with a small amount of diatomite, and the filter cake was washed once with 20 ml of a mixed solvent of dichloromethane and methanol (V/V=10:1). Then, the filtrate was collected and concentrated under reduced pressure to give 559 mg of crude product of the titled compound (transparent and viscous material) which was used in the subsequent reaction directly without further purification.

MS (ESI): m/z 207.1 [M+H]$^+$.

Step 3: Preparation of 5-(2-chloro-5-fluoropyrimidin-4-yl)-3-ethyl-7-fluoro-2,3-dimethyl-3H-indole

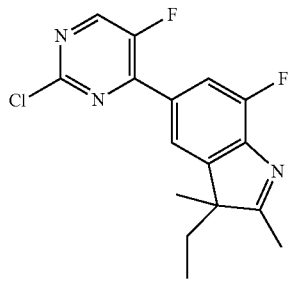 [SMILES: CCC1(C)C(C)=Nc2c(F)cc(-c3nc(Cl)ncc3F)cc21]

This intermediate was prepared by the same method as Steps 1-3 of Example 16.

Step 4: Preparation of 4-(3-ethyl-7-fluoro-2,3-dimethyl-3H-indol-5-yl)-N-(5-(4-ethylpiperazin-1-yl)pyridin-2-yl)-5-fluoropyrimidine-2-amino

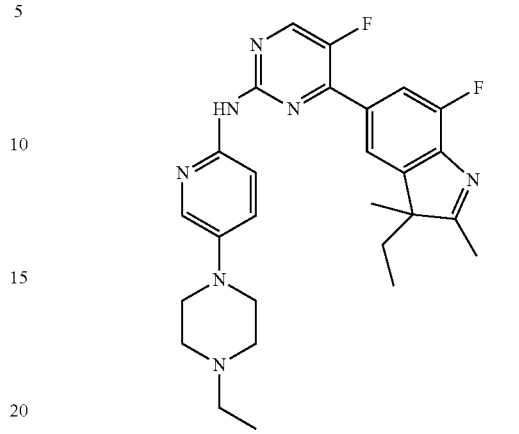

A reaction flask was charged with 321 mg (1 mmol) of 5-(2-chloro-5-fluoropyrimidin-4-yl)-3-ethyl-7-fluoro-2,3-dimethyl-3H-indole prepared in Step 3, 206 mg (1 mmol) of 5-(4-ethylpiperazin-1-yl)pyridin-2-amino obtained in Step 2, 2 ml of 1,4-dioxane, 650 mg (2 mmol) of $Cs_2CO_3$, 91 mg (0.1 mmol) of $Pd_2(dba)_3$, and 58 mg (0.1 mmol) of diphenylphosphine. The mixture was heated to 120° C. to conduct microwave reaction for 1 hour. The reaction product was cooled to room temperature, added with 10 ml of water and then extracted with ethyl acetate three times (40 ml for each time). The organic phases were combined, washed once with 40 ml of saturated salt solution, dried with sodium sulfate, filtered, concentrated under reduced pressure and separated by silica gel column chromatography (DCM/MeOH=10:1) to give the titled compound (49 mg, yellow solid), yield 10%.

$^1$H-NMR (400 MHz, CDCl$_3$) δ9.25 (br s, 1H), 8.46 (d, 1H, J=3.2 Hz), 8.28 (d, 1H, J=9.2 Hz), 8.17 (d, 1H, J=2.0 Hz), 7.90 (d, 1H, J=11.2 Hz), 7.82 (s, 1H), 7.35 (dd, 1H, J=9.2 Hz, 2.8 Hz), 3.20-3.18 (m, 4H), 2.64-2.61 (m, 4H), 2.51 (q, 2H, J=6.8 Hz), 2.31 (s, 3H), 2.03-1.94 (m, 1H), 1.89-1.82 (m, 1H), 1.36 (s, 3H), 1.13 (t, 3H, J=7.2 Hz), 0.48 (t, 3H, J=7.2 Hz).

MS (ESI): m/z 492.3[M+H]$^+$.

Example 20

5-Fluoro-4-(7'-fluoro-2'-methylspiro[cyclopentane-1,3'-indol]-5'-yl)-N-(5-(4-methylpiperazin-1-yl)pyridin-2-yl)pyrimidine-2-amino

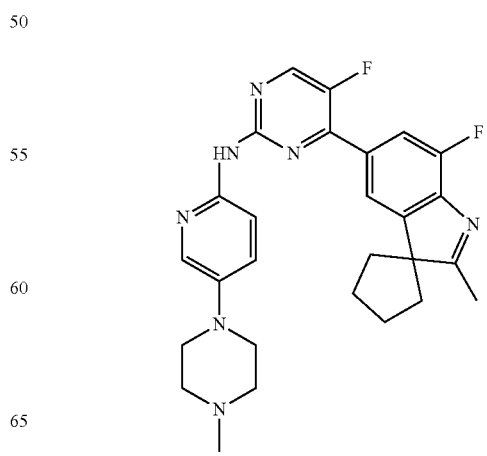

The titled compound was obtained by the steps similar to those of Example 16.

¹H-NMR (400 MHz, DMSO-d₆) δ9.77 (br s, 1H), 8.63 (d, 1H, J=4.0 Hz), 8.02-7.98 (m, 3H), 7.82 (d, 1H, J=11.2 Hz), 7.41 (dd, 1H, J=8.8 Hz, 2.8 Hz), 3.13-3.11 (m, 4H), 2.49-2.46 (m, 4H), 2.33 (s, 3H), 2.26 (s, 3H), 2.23-2.07 (m, 6H), 1.76-1.74 (m, 2H).

MS (ESI): m/z 490.3[M+H]⁺.

Example 21

N-(5-(1-ethylpiperidin-4-yl)pyridin-2-yl)-5-fluoro-4-(2'-methylspiro[cyclopentane-1,3'-indol]-5'-yl)pyrimidine-2-amino

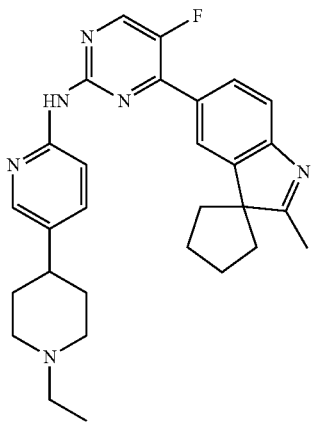 [SMILES: CCN1CCC(c2ccc(Nc3ncc(F)c(-c4ccc5c(c4)C4(CCCC4)C(C)=N5)n3)nc2)CC1]

The titled compound was obtained by the steps similar to those of Example 12.

¹H-NMR (400 MHz, DMSO-d₆) δ9.91 (br s, 1H), 8.65 (d, 1H, J=4.0 Hz), 8.28-8.14 (m, 3H), 8.04 (d, 1H, J=8.4 Hz), 7.43 (dd, 1H, J=8.4 Hz, 2.0 Hz), 7.60 (d, 1H, J=8.0 Hz), 3.00-2.97 (m, 4H), 2.38-2.33 (m, 2H), 2.30 (s, 3H), 2.08-2.07 (m, 6H), 1.99-1.94 (m, 2H), 1.77-1.64 (m, 6H), 1.02 (t, 3H, J=7.2 Hz).

MS (ESI): m/z 485.3[M+H]⁺.

Example 22

N-(5-(4-ethylpiperazin-1-yl)pyridin-2-yl)-5-fluoro-4-(2'-methylspiro[cyclopentane-1,3'-indol]-5'-yl)pyrimidine-2-amino

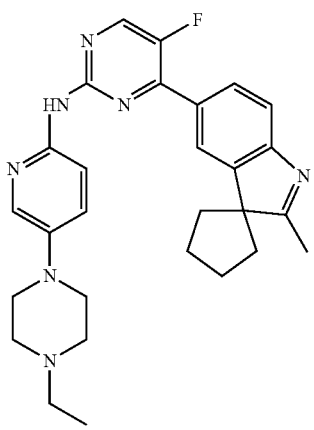 [SMILES: CCN1CCN(c2ccc(Nc3ncc(F)c(-c4ccc5c(c4)C4(CCCC4)C(C)=N5)n3)nc2)CC1]

The titled compound was obtained by the steps similar to those of Example 19.

¹H-NMR (400 MHz, CDCl₃) δ8.87 (br s, 1H), 8.42 (d, 1H, J=3.6 Hz), 8.33 (d, 1H, J=9.2 Hz), 8.13-8.10 (m, 3H), 7.65 (d, 1H, J=8.0 Hz), 7.35 (dd, 1H, J=8.8 Hz, 2.4 Hz), 3.19-3.18 (m, 4H), 2.64-2.63 (m, 4H), 2.53 (q, 2H, J=6.8 Hz), 2.35 (s, 3H), 2.27-2.06 (m, 6H), 1.88-1.85 (m, 2H), 1.14 (t, 3H, J=6.8 Hz).

MS (ESI): m/z 486.4[M+H]⁺.

Example 23

N-(5-(4-methylpiperidin-1-yl)pyridin-2-yl)-5-fluoro-4-(2'-methylspiro [cyclopentane-1,3'-indol]-5'-yl)pyrimidine-2-amino

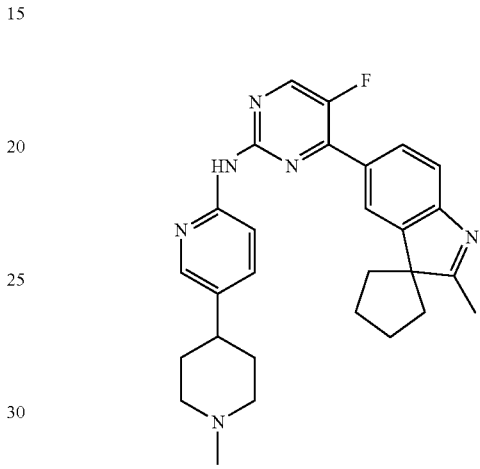

The titled compound was obtained by the steps similar to those of Example 17.

¹H-NMR (400 MHz, CDCl₃) δ9.24 (br s, 1H), 8.47 (d, 1H, J=3.2 Hz), 8.38 (d, 1H, J=8.8 Hz), 8.31 (s, 1H), 8.14-8.09 (m, 2H), 7.64 (d, 1H, J=8.4 Hz), 7.57 (dd, 1H, J=8.4 Hz, 2.4 Hz), 3.00-2.98 (m, 2H), 2.49-2.46 (m, 1H), 2.35 (s, 3H), 2.33 (s, 3H), 2.16-1.99 (m, 8H), 1.85-1.76 (m, 6H).

MS (ESI): m/z 471.3[M+H]⁺.

Example 24

4-(3-ethyl-7-fluoro-2,3-dimethyl-3H-indol-5-yl)-5-fluoro-N-(5-(1-methylpiperidin-4-yl)pyridin-2-yl)pyrimidine-2-amino

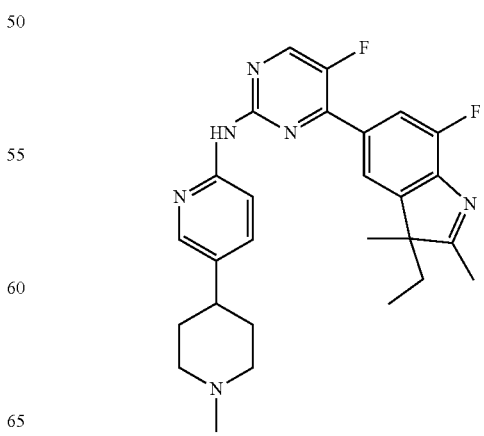

The titled compound was obtained by the steps similar to those of Example 17.

¹H-NMR (400 MHz, CDCl₃) δ9.74 (br s, 1H), 8.50 (d, 1H, J=3.6 Hz), 8.35-8.32 (m, 2H), 7.88-7.82 (m, 2H), 7.57 (d, 1H, J=8.8 Hz), 2.97-2.95 (m, 2H), 2.49-2.42 (m, 1H), 2.30 (s, 6H), 2.24-1.93 (m, 3H), 1.88-1.74 (m, 5H), 1.35 (s, 3H), 0.47 (t, 3H, J=7.2 Hz).

MS (ESI): m/z 477.3[M+H]⁺.

Example 25

5-Fluoro-N-(5-(4-methylpiperazin-1-yl)pyridin-2-yl)-4-(2'-methylspiro [cyclopentane-1,3'-indol]-5'-yl)pyrimidine-2-amino

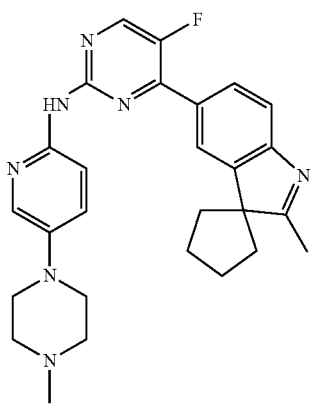 [SMILES: CC1=Nc2ccc(-c3nc(Nc4ccc(N5CCN(C)CC5)cn4)ncc3F)cc2C12CCCC2]

The titled compound was obtained by the steps similar to those of Example 16.

¹H-NMR (400 MHz, CDCl₃) δ9.28 (br s, 1H), 8.44 (d, 1H, J=3.6 Hz), 8.33 (d, 1H, J=9.2 Hz), 8.18 (d, 1H, J=2.0 Hz), 8.12-8.09 (m, 2H), 7.64 (d, 1H, J=8.0 Hz), 7.33 (dd, 1H, J=9.2 Hz, 2.4 Hz), 3.16-3.14 (m, 4H), 2.59-2.58 (m, 4H), 2.35 (s, 3H), 2.34 (s, 3H), 2.15-2.06 (m, 6H), 1.87-1.83 (m, 2H).

MS (ESI): m/z 472.3[M+H]⁺.

Example 26

4-(3-ethyl-7-fluoro-2,3-dimethyl-3H-indol-5-yl)-N-(5-(1-ethylpiperidin-4-yl) pyridin-2-yl)-5-fluoropyrimidine-2-amino

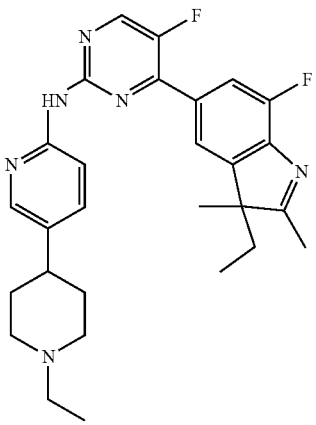 [SMILES: CCN1CCC(c2ccc(Nc3ncc(F)c(-c4cc(F)c5c(c4)C(C)(CC)C(C)=N5)n3)nc2)CC1]

The titled compound was obtained by the steps similar to those of Example 12.

¹H-NMR (400 MHz, DMSO-d₆) δ9.99 (br s, 1H), 8.70 (d, 1H, J=3.2 Hz), 8.19 (s, 1H), 8.14 (d, 1H, J=8.8 Hz), 7.92 (s, 1H), 7.85 (d, 1H, J=11.2 Hz), 7.69 (d, 1H, J=8.4 Hz), 3.04-3.02 (m, 2H), 2.42-2.41 (m, 2H), 2.28 (s, 3H), 2.04-1.99 (m, 3H), 1.89-1.84 (m, 1H), 1.78-1.63 (m, 4H), 1.33 (s, 3H), 1.04 (t, 3H, J=6.8 Hz), 0.36 (t, 3H, J=7.2 Hz).

MS (ESI): m/z 491.3[M+H]⁺.

Example 27

N-(5-(4-ethylpiperazin-1-yl)pyridin-2-yl)-5-fluoro-4-(7'-fluoro-2'-methylspiro [cyclopentane-1,3'-indol]-5'-yl)pyrimidine-2-amino

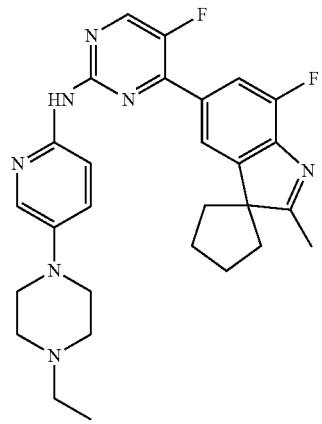 [SMILES: CCN1CCN(c2ccc(Nc3ncc(F)c(-c4cc(F)c5c(c4)C4(CCCC4)C(C)=N5)n3)nc2)CC1]

The titled compound was obtained by the steps similar to those of Example 19.

¹H-NMR (400 MHz, CDCl₃) δ8.92 (br s, 1H), 8.44 (d, 1H, J=3.6 Hz), 8.29 (d, 1H, J=9.2 Hz), 8.15 (d, 1H, J=2.8 Hz), 7.94 (s, 1H), 7.89 (d, 1H, J=11.2 Hz), 7.36 (dd, 1H, J=9.2 Hz, 2.8 Hz), 3.21-3.19 (m, 4H), 2.65-2.63 (m, 4H), 2.51 (q, 2H, J=7.2 Hz), 2.38 (s, 3H), 2.22-2.07 (m, 6H), 1.89-1.86 (m, 2H), 1.15 (t, 3H, J=7.2 Hz).

MS (ESI): m/z 504.3[M+H]⁺.

Example 28

2-(4-(6-((5-fluoro-4-(7'-fluoro-2'-methylspiro[cyclopentane-1,3'-indol]-5'-yl) pyrimidin-2-yl)amino)pyridin-3-yl)piperazin-1-yl)ethanol

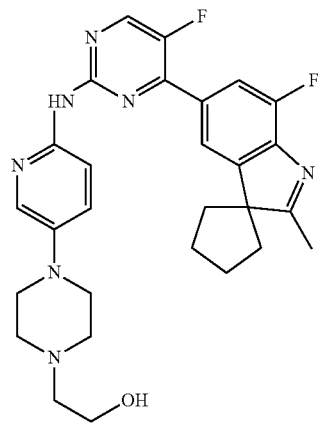

A reaction flask was charged with 5-fluoro-4-(7'-fluoro-2'-methylspiro[cyclopentane-1,3'-indol]-5'-yl)-N-(5-(piperazin-1-yl)pyridin-2-yl)pyrimidine-2-amino 20 mg (0.04 mmol, prepared by the same method as in Example 6), 16 mg (0.12 mmol) of 2-bromoethanol, 2 ml of DMF and 17 mg (0.12 mmol) of cesium carbonate. The mixture was heated to 80° C. and reacted for 1 hour, and then the reaction product was cooled to room temperature, added with 10 ml of water, and extracted three times with ethyl acetate (40 ml for each time). The organic phases were combined, washed once with 40 ml of saturated salt solution, dried with anhydrous sodium sulfate, filtered, concentrated under reduced pressure, and separated by silica gel column chromatography (DCM/MeOH=10:1) to give the titled compound (10 mg, yellow solid), yield 55%.

$^1$H-NMR (400 MHz, CDCl$_3$) δ8.52 (br s, 1H), 8.43 (d, 1H, J=2.8 Hz), 8.29 (d, 1H, J=9.2 Hz), 8.09 (s, 1H), 7.94 (s, 1H), 7.89 (d, 1H, J=10.8 Hz), 7.36 (d, 1H, J=8.8 Hz), 3.70-3.68 (m, 2H), 3.19-3.18 (m, 4H), 2.71-2.63 (m, 7H), 2.39 (s, 3H), 2.25-2.00 (m, 6H), 1.90-1.87 (m, 2H).

MS (ESI): m/z 520.3[M+H]$^+$.

Example 29

4-(3,3-diethyl-7-fluoro-2-methyl-3H-indol-5-yl)-5-fluoro-N-(5-(piperazin-4-yl)pyridin-2-yl)pyrimidine-2-amino

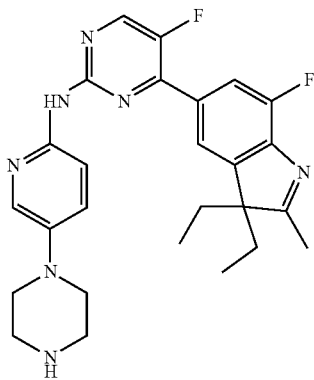

The titled compound was obtained by the steps similar to those of Example 1.

$^1$H-NMR (400 MHz, CDCl$_3$) δ8.66 (br s, 1H), 8.45 (d, 1H, J=3.6 Hz), 8.29 (d, 1H, J=9.2 Hz), 8.11 (d, 1H, J=2.8 Hz), 7.94 (d, 1H, J=11.2 Hz), 7.81 (s, 1H), 7.37 (dd, 1H, J=8.8 Hz, 2.4 Hz), 3.13-3.12 (m, 4H), 3.08-3.07 (m, 4H), 2.30 (s, 3H), 2.08-1.99 (m, 2H), 1.91-1.82 (m, 3H), 0.46 (t, 6H, J=7.6 Hz).

MS (ESI): m/z 478.3[M+H]$^+$.

Example 30

2-(4-(6-((5-fluoro-4-(7'-fluoro-2'-methylspiro[cyclopentane-1,3'-indol]-5'-yl) pyrimidin-2-yl)amino) pyridin-3-yl)piperidin-1-yl)ethanol

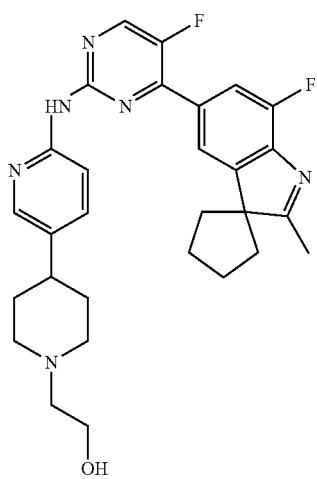 [SMILES: CC1=Nc2c(F)cc(-c3nc(Nc4ccc(C5CCN(CCO)CC5)cn4)ncc3F)cc2C12CCCC2]

A reaction flask was charged with 20 mg (0.04 mmol) of 5-fluoro-4-(7'-fluoro-2'-methylspiro[cyclopentane-1,3'-indol]-5'-yl)-N-(5-(piperidin-4-yl)pyridin-2-yl)pyrimidine-2-amino prepared by the same methods as Example 13, 16 mg (0.12 mmol) of 2-bromoethanol, 2 mL of DMF, and 17 mg (0.12 mmol) of cesium carbonate, and the mixture was heated to 80° C. and reacted for 1 hour. Then, the reaction product was cooled to room temperature, added with 10 ml of water and extracted three times with ethyl acetate (40 ml for each time). The organic phases were combined, washed once with 40 ml of saturated salt solution, dried with anhydrous sodium sulfate, filtered and concentrated under reduced pressure, and separated by silica gel column chromatography (DCM/MeOH=10:1) to give the titled compound (10 mg, yellow solid), yield 55%.

$^1$H-NMR (400 MHz, CDCl$_3$) δ8.63 (br s, 1H), 8.46 (d, 1H, J=3.2 Hz), 8.34 (d, 1H, J=8.4 Hz), 8.26 (s, 1H), 7.96 (s, 1H), 7.90 (d, 1H, J=10.8 Hz), 7.60 (d, 1H, J=8.0 Hz), 3.67-3.66 (m, 2H), 3.08-3.06 (m, 2H), 2.60-2.52 (m, 4H), 2.39 (s, 3H), 2.25-2.11 (m, 8H), 1.89-1.83 (m, 4H), 1.80-1.77 (m, 2H).

MS (ESI): m/z 519.3[M+H]$^+$.

Example 31

5-Fluoro-4-(7-fluoro-2,3,3-trimethyl-3H-indol-5-yl)-N-(5-(1-methylpiperidin-4-yl)pyridin-2-yl)pyrimidine-2-amino

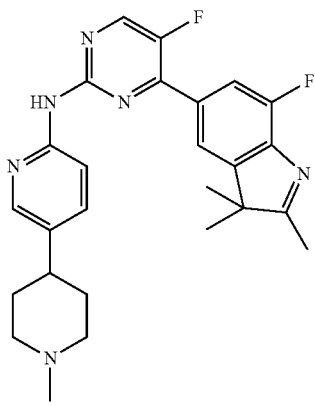 [SMILES: CC1=Nc2c(F)cc(-c3nc(Nc4ccc(C5CCN(C)CC5)cn4)ncc3F)cc2C1(C)C]

The titled compound was obtained by the steps similar to those of Example 17.

$^1$H-NMR (400 MHz, Methanol-d$_4$) δ8.57 (br s, 1H), 8.37 (d, 1H, J=3.6 Hz), 8.18 (s, 1H), 8.13 (d, 1H, J=8.8 Hz), 7.84 (s, 1H), 7.70 (d, 1H, J=11.2 Hz), 7.51 (d, 1H, J=7.2 Hz), 3.21-3.18 (m, 2H), 2.60-2.54 (m, 4H), 2.50-2.44 (m, 2H), 2.37 (s, 3H), 1.90-1.79 (m, 4H), 1.38 (s, 6H).

MS (ESI): m/z 463.3[M+H]$^+$.

Example 32

4-(3-ethyl-2,3-dimethyl-3H-indol-5-yl)-5-fluoro-N-(5-(piperazin-1-yl)pyridin-2-yl)pyrimidine-2-amino

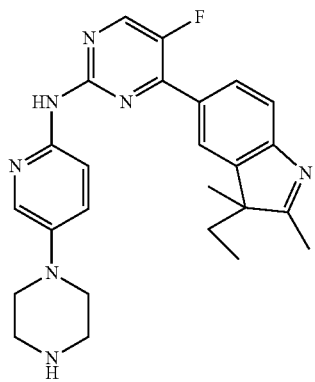 [SMILES: CCC1(C)C(C)=Nc2ccc(-c3nc(Nc4ccc(N5CCNCC5)cn4)ncc3F)cc21]

The titled compound was obtained by the steps similar to those of Example 6.

$^1$H-NMR (400 MHz, CDCl$_3$) δ9.68 (br s, 1H), 8.44 (d, 1H, J=3.6 Hz), 8.32 (d, 1H, J=8.8 Hz), 8.18 (d, 1H, J=2.4 Hz), 8.11 (d, 1H, J=8.0 Hz), 7.98 (s, 1H), 7.64 (d, 1H, J=8.0 Hz), 7.30 (d, 1H, J=2.8 Hz), 3.05-3.04 (m, 4H), 3.00-2.98 (m, 4H), 2.26 (s, 3H), 2.00-1.90 (m, 2H), 1.83-1.74 (m, 1H), 1.32 (s, 3H), 0.45 (t, 1H, J=7.2 Hz).

MS (ESI): m/z 446.3[M+H]$^+$.

Example 33

4-(3-ethyl-2,3-dimethyl-3H-indol-5-yl)-5-fluoro-N-(5-(piperidin-4-yl)pyridin-2-yl)pyrimidine-2-amino

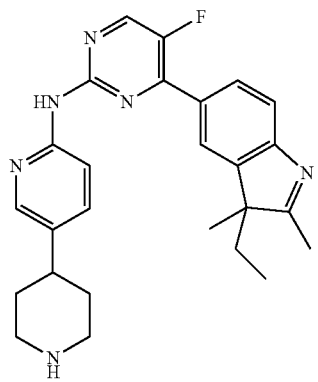 [SMILES: CCC1(C)C(C)=Nc2ccc(-c3nc(Nc4ccc(C5CCNCC5)cn4)ncc3F)cc21]

The titled compound was obtained by the steps similar to those of Example 13.

$^1$H-NMR (400 MHz, Methanol-d$_4$) δ8.33 (d, 1H, J=2.8 Hz), 8.16-8.13 (m, 2H), 7.95-7.93 (m, 2H), 7.48-7.41 (m, 2H), 3.18-3.15 (m, 2H), 2.73 (t, 1H, J=11.6 Hz), 2.59-2.53 (m, 1H), 2.30 (s, 3H), 2.01-1.96 (m, 1H), 1.89-1.83 (m, 1H), 1.79-1.76 (m, 2H), 1.66-1.58 (m, 2H), 1.32 (s, 3H), 0.42 (t, 1H, J=6.8 Hz).

MS (ESI): m/z 445.3[M+H]$^+$.

Example 34

4-(3-ethyl-2,3-dimethyl-3H-indol-5-yl)-5-fluoro-N-(5-(4-methylpiperazin-1-yl)pyridin-2-yl)pyrimidine-2-amino

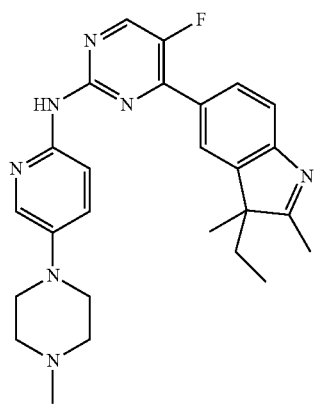 [SMILES: CCC1(C)C(C)=Nc2ccc(-c3nc(Nc4ccc(N5CCN(C)CC5)cn4)ncc3F)cc21]

The titled compound was obtained by the steps similar to those of Example 16.

$^1$H-NMR (400 MHz, Methanol-d$_4$) δ8.42 (d, 1H, J=3.2 Hz), 8.18 (d, 1H, J=8.8 Hz), 8.09-8.01 (m, 3H), 7.57 (d, 1H, J=8.0 Hz), 7.42-7.37 (m, 1H), 3.22-3.15 (m, 4H), 2.61-2.60 (m, 4H), 2.35 (s, 3H), 2.32 (s, 3H), 2.07-2.02 (m, 1H), 1.94-1.89 (m, 1H), 1.38 (s, 3H), 0.43 (t, 1H, J=7.2 Hz).

MS (ESI): m/z 460.3[M+H]$^+$.

Example 35

4-(3-ethyl-2,3-dimethyl-3H-indol-5-yl)-5-fluoro-N-(5-(1-methylpiperidin-4-yl)-pyridin-2-yl)pyrimidine-2-amino

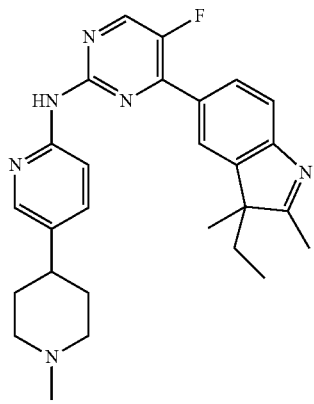 [SMILES: CCC1(C)C(C)=Nc2ccc(-c3nc(Nc4ccc(C5CCN(C)CC5)cn4)ncc3F)cc21]

The titled compound was obtained by the steps similar to those of Example 17.

$^1$H-NMR (400 MHz, CDCl$_3$) δ8.97 (br s, 1H), 8.47 (d, 1H, J=3.6 Hz), 8.39 (d, 1H, J=8.4 Hz), 8.30 (d, 1H, J=2.0 Hz), 8.15 (d, 1H, J=8.4 Hz), 8.04 (s, 1H), 7.68 (d, 1H, J=8.0 Hz), 7.59 (dd, 1H, J=8.8 Hz, 2.4 Hz), 3.01-2.98 (m, 4H), 2.51-2.45 (m, 1H), 2.34 (s, 3H), 2.31 (s, 3H), 2.10-1.97 (m, 3H), 1.85-1.81 (m, 5H), 1.37 (s, 3H), 0.49 (t, 1H, J=7.2 Hz).
MS (ESI): m/z 459.3[M+H]$^+$.

Example 36

4-(3-ethyl-2,3-dimethyl-3H-indol-5-yl)-N-(5-(4-ethylpiperazin-1-yl)pyridin-2-yl)-5-fluoropyrimidine-2-amino

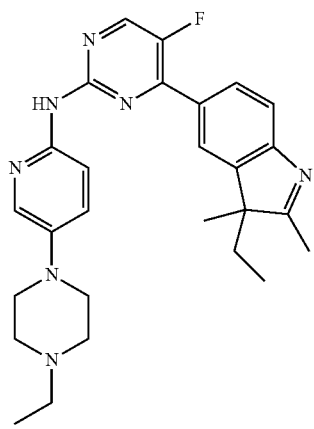 [SMILES: CCN1CCN(c2ccc(Nc3ncc(F)c(-c4ccc5c(c4)C(C)(CC)C(C)=N5)n3)nc2)CC1]

The titled compound was obtained by the steps similar to those of Example 19.

$^1$H-NMR (400 MHz, CDCl$_3$) δ8.93 (br s, 1H), 8.44 (d, 1H, J=3.6 Hz), 8.33 (d, 1H, J=9.2 Hz), 8.15-8.13 (m, 2H), 8.02 (s, 1H), 7.67 (d, 1H, J=8.0 Hz), 7.35 (d, 1H, J=8.0 Hz), 3.19-3.18 (m, 4H), 2.63-2.62 (m, 4H), 2.52-2.47 (m, 2H), 2.30 (s, 3H), 2.02-1.97 (m, 1H), 1.86-1.80 (m, 1H), 1.36 (s, 3H), 1.14 (t, 3H, J=7.2 Hz), 0.57 (t, 1H, J=7.2 Hz).
MS (ESI): m/z 474.3[M+H]$^+$.

Example 37

5-Fluoro-N-(5-(1-methylpiperidin-4-yl)pyridin-2-yl)-4-(2,3,3-trimethyl-3H-indol-5-yl)pyrimidine-2-amino

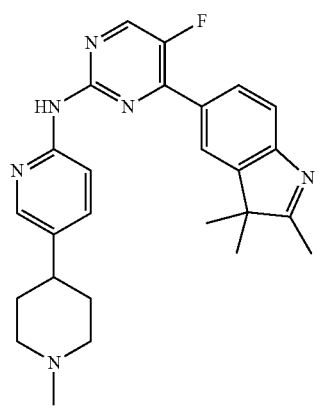 [SMILES: CC1=Nc2ccc(-c3nc(Nc4ccc(C5CCN(C)CC5)cn4)ncc3F)cc2C1(C)C]

The titled compound was obtained by the steps similar to those of Example 17.

$^1$H-NMR (400 MHz, CDCl$_3$) δ9.03 (br s, 1H), 8.46 (d, 1H, J=3.2 Hz), 8.38 (d, 1H, J=8.4 Hz), 8.29 (s, 1H), 7.67 (d, 1H, J=8.0 Hz), 7.60 (dd, 1H, J=8.8 Hz, 1.6 Hz), 3.00-2.97 (m, 2H), 2.49-2.44 (m, 1H), 2.34 (s, 3H), 2.33 (s, 3H), 2.10-2.03 (m, 2H), 1.84-1.79 (m, 4H), 1.37 (s, 6H).
MS (ESI): m/z 445.3[M+H]$^+$.

Example 38

4-(3,3-diethyl-7-fluoro-2-methyl-3H-indol-5-yl)-5-fluoro-N-(5-(1-methylpiperidin-4-yl)pyridin-2-yl)pyrimidine-2-amino

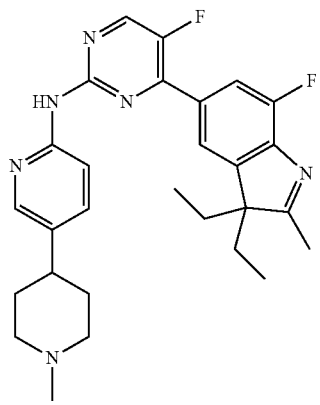 [SMILES: CCC1(CC)C(C)=Nc2c(F)cc(-c3nc(Nc4ccc(C5CCN(C)CC5)cn4)ncc3F)cc21]

The titled compound was obtained by the steps similar to those of Example 17.

$^1$H-NMR (400 MHz, DMSO-d$_6$) δ9.95 (s, 1H), 8.69 (s, 1H), 8.19-8.11 (m, 2H), 7.89-7.84 (m, 2H), 7.67 (d, 1H,

J=7.6 Hz), 2.87-2.85 (m, 2H), 2.25 (s, 3H), 2.19 (s, 3H), 2.02-1.92 (m, 6H), 1.90-1.65 (m, 4H), 0.34 (m, 6H).

MS (ESI): m/z 491.3[M+H]$^+$.

Example 39

1-(2-((4-(3-Ethyl-7-fluoro-2,3-dimethyl-3H-indol-5-yl)-5-fluoropyrimidin-2-yl)amino)-7,8-dihydro-1,6-naphthyridine-6 (5H)-yl)-2-hydroxyacetamide

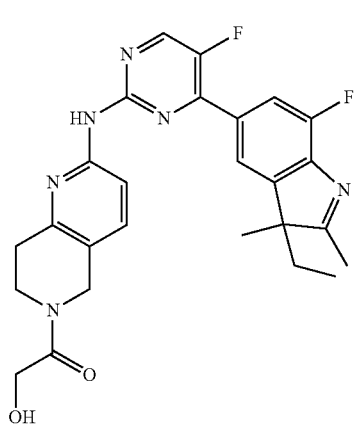 [SMILES: CCC1(C)C(C)=Nc2c(F)cc(-c3nc(Nc4ccc5c(n4)CCN(C(=O)CO)C5)ncc3F)cc21]

Step 1: 2-(2-Chloro-7,8-dihydro-1,6-naphthyridine-6(5H)-yl)-2-acetoxyacetamide

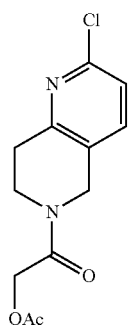 [SMILES: CC(=O)OCC(=O)N1CCc2nc(Cl)ccc2C1]

A reaction flask was charged with 1.0 g (5.95 mmol) of 2-chloro-5,6,7,8-tetrahydro-1,6-naphthyridine, 1.21 g (11.90 mmol) of triethylamine, and 5 ml of dichloromethane, and then 2-chloro-2-acetoxyacetyl chloride (1.22 g, 8.93 mmol) was slowly dropwise added. The mixture was allowed to react for 1 hour at room temperature, and the reaction was quenched with 5 mL of water. The solvent was removed, and the residue was extracted three times with dichloromethane (15 mL for each time). The organic phases were combined, washed once with 10 ml of saturated salt solution, dried with anhydrous sodium sulfate, filtered and concentrated under reduced pressure to give crude product of the titled compound (1.09 g, off-white), yield 68.21%.

MS (ESI): m/z 269.1 [M+H]$^+$.

Step 2: 1-(2-((4-(3-Ethyl-7-fluoro-2,3-dimethyl-3H-indol-5-yl)-5-fluoropyrimidin-2-yl)amino)-7,8-dihydro-1,6-naphthyridine-6(5H)-yl)-2-hydroxyacetamide

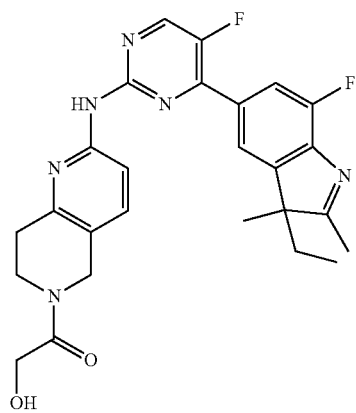 [SMILES: CCC1(C)C(C)=Nc2c(F)cc(-c3nc(Nc4ccc5c(n4)CCN(C(=O)CO)C5)ncc3F)cc21]

A reaction flask was charged with 101 mg (0.34 mmol) of 4-(3-ethyl-7-fluoro-2,3-dimethyl-3H-indol-5-yl)-5-fluoropyrimidine-2-amino prepared by the method similar to Steps 1-3 of Example 1, 85.2 mg (0.32 mmol) of 2-(2-chloro-7,8-dihydro-1,6-naphthyridine-6(5H)-yl)-2-acetoxyacetamide, 10 mL of dioxane, 65.3 mg (0.68 mmol) of sodium tert-butoxide, 31.2 mg (0.034 mmol) of Pd$_2$(dba)$_3$, 19.7 mg (0.034 mmol) of 4,5-bis (diphenylphosphino)-9,9-dimethylxanthene. The mixture was heated to 120° C. and allowed to conduct microwave reaction for 1 hour, and then the reaction product was cooled to room temperature, added with 50 ml of water, and extracted three times with ethyl acetate (50 ml for each time). The organic phases were combined, washed once with 50 ml of saturated salt solution, dried with anhydrous sodium sulfate, filtered, concentrated, and separated by silica gel column chromatography (dichloromethane/methanol=10:1) to give the titled compound (20 mg, white solid), yield 12%.

$^1$H-NMR (400 MHz, DMSO-d$_6$) δ9.98 (s, 1H), 8.70 (d, 1H, J=3.6 Hz), 8.07 (d, 1H, J=8.4 Hz), 7.94 (s, 1H), 7.87 (d, 1H, J=11.2 Hz), 7.64-7.57 (m, 1H), 4.68-4.55 (m, 3H), 4.22-4.21 (m, 2H), 4.21-4.19 (m, 2H), 2.89-2.81 (m, 2H), 2.28 (s, 3H), 2.04-1.84 (m, 2H), 1.33 (s, 3H), 0.37 (t, 3H, J=7.2 Hz).

MS (ESI): m/z 493.2[M+H]$^+$.

Example 40

1-(2-((5-fluoro-4-(7'-fluoro-2'-methylspiro[cyclopentane-1,3'-indol]-5'-yl) pyrimidin-2-yl)amino)-7,8-dihydro-1,6-naphthyridine-6 (5H)-yl)-2-hydroxyacetamide

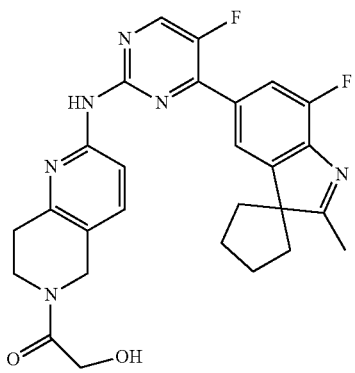 [SMILES: CC1=Nc2c(F)cc(-c3nc(Nc4ccc5c(n4)CCN(C(=O)CO)C5)ncc3F)cc2C12CCCC2]

The titled compound was obtained by the steps similar to those of Example 39.

$^1$H-NMR (400 MHz, DMSO-$d_6$) δ10.07 (brs, 1H), 8.69 (d, 1H, J=3.6 Hz), 8.53 (s, 1H), 8.09-8.02 (m, 1H), 7.98 (s, 1H), 7.88 (d, 1H, J=12.4 Hz), 7.62-7.54 (m, 1H), 4.73 (brs, 1H), 4.62- 4.61 (m, 2H), 4.21-4.19 (m, 2H), 2.89-2.81 (m, 2H), 2.50 (s, 2H), 2.34-2.11 (m, 5H), 1.75-1.72 (m, 2H).

MS (ESI): m/z 505.2[M+H]$^+$.

Example 41

N-(5-(4-(cyclopropylmethyl)piperazin-1-yl)pyridin-2-yl)-5-fluoro-4-(7'-fluoro-2'-methylspiro[cyclopentane-1,3'-indol]-5'-yl)pyrimidine-2-amino

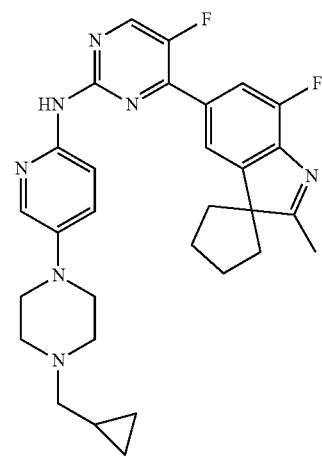 [SMILES: CC1=Nc2c(F)cc(-c3nc(Nc4ccc(N5CCN(CC6CC6)CC5)cn4)ncc3F)cc2C12CCCC2]

The intermediate 5-fluoro-4-(7'-fluoro-2'-methylspiro[cyclopentane-1,3'-indol]-5'-yl)-N-(5-(piperazin-1-yl)pyridin-2-yl)pyrimidine-2-amino was obtained by the steps similar to those of Example 6.

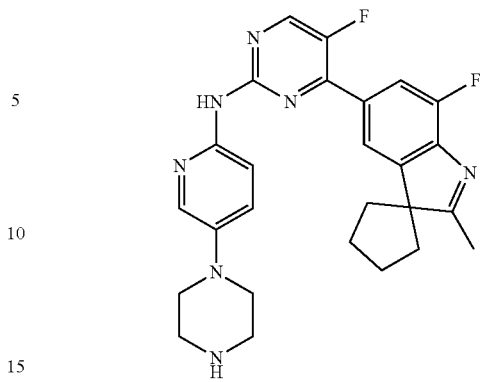

The above intermediate 5-fluoro-4-(7'-fluoro-2'-methylspiro[cyclopentane-1,3'-indol]-5'-yl)-N-(5-(piperazin-1-yl)pyridin-2-yl)pyrimidine-2-amino (150 mg, 0.32 mmol), bromomethyl cyclopropane, acetonitrile (5 ml), and potassium carbonate (130.0 mg, 0.96 mmol) were added to a reaction flask, and heated to 80° C. and reacted for 4 hours. The reaction product was cooled to room temperature, added with 50 ml of water, extracted three times with 10 ml of dichloromethane (10 ml for each time). The organic layers were combined, washed once with 15 mg of saturated salt solution, dried with anhydrous sodium sulfate, filtered, and separated by column chromatography (dichloromethane/Methanol=10:1) to obtain the titled product of this example (42.1 mg, white solid).

$^1$H-NMR (400 MHz, DMSO-$d_6$) δ9.89 (s, 1H), 8.68 (m, 1H), 8.64-8.01 (m, 3H), 7.87 (d, 1H, J=14.4 Hz), 7.42-7.40 (m, 1H), 3.14-3.13 (m, 5H), 2.60-2.51 (m, 5H), 2.33 (s, 3H), 2.24-2.23 (m, 2H), 2.09-2.02 (m, 6H), 1.99-1.97 (m, 2H), 1.75-1.74 (m, 2H), 0.85-0.83 (m, 2H), 0.48-0.47 (m, 2H).

MS (ESI): m/z 530.3[M+H]$^+$.

Example 42

4-(3-ethyl-7-fluoro-2,3-dimethyl-3H-indol-5-yl)-5-fluoro-N-(5-((4-methylpiperazin-1-yl)methyl)pyridin-2-yl)pyrimidine-2-amino

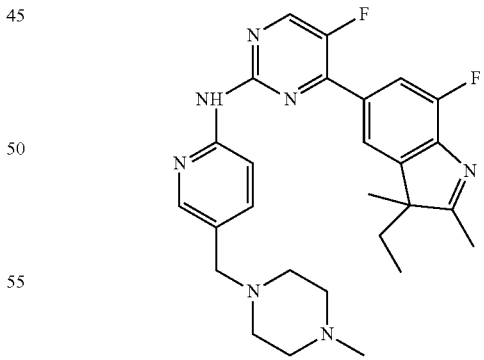

The titled compound was obtained by the steps similar to those of Example 2.

$^1$H-NMR (400 MHz, DMSO-$d_6$) δ10.06 (brs, 1H), 8.72 (d, 1H, J=3.2 Hz), 8.18-8.15 (m, 2H), 7.93 (s, 1H), 7.86 (d, 1H, J=11.6 Hz), 7.67 (d, 1H, J=5.2 Hz), 3.42 (s, 2H), 2.35-2.28 (m, 8H), 2.14 (s, 3H), 2.04-1.98 (m, 1H), 1.89-1.84 (m, 1H), 1.34 (s, 3H), 0.36 (t, 3H, J=7.2 Hz).

MS (ESI): m/z 492.3[M+H]$^+$.

Example 43

5-Fluoro-4-(7'-fluoro-2'-methylspiro[cyclopentane-1,3'-indol]-5'-yl)-N-(5-((4-methylpiperazin-1-yl)methyl)pyridin-2-yl)pyrimidine-2-amino

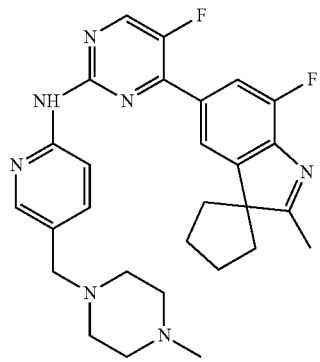 [SMILES: CC1=Nc2c(F)cc(-c3nc(Nc4ccc(CN5CCN(C)CC5)cn4)ncc3F)cc2C12CCCC2]

The titled compound was obtained by the steps similar to those of Example 2.

$^1$H-NMR (400 MHz, DMSO-d$_6$) δ10.09 (s, 1H), 8.71 (d, 1H, J=3.2 Hz), 8.18-8.15 (m, 2H), 8.02 (s, 1H), 7.85 (d, 1H, J=11.2 Hz), 7.67 (d, 1H, J=8.4 Hz), 3.43 (s, 2H), 2.50-2.34 (m, 8H), 2.14 (s, 3H), 2.14-2.08 (m, 6H), 1.75-1.74 (m, 2H), 1.75-1.72 (m, 2H).

MS (ESI): m/z 504.2[M+H]$^+$.

Example 44

N-(5-(1-methylpiperidin-4-yl)-(6-methylpyridin)-2-yl)-5-fluoro-4-(7'-fluoro-2'-methylspiro[cyclopentane-1,3'-indol]-5'-yl)pyrimidine-2-amino

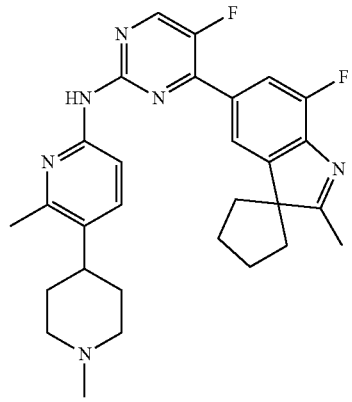 [SMILES: CC1=Nc2c(F)cc(-c3nc(Nc4ccc(C5CCN(C)CC5)c(C)n4)ncc3F)cc2C12CCCC2]

The titled compound was obtained by the steps similar to those of Example 12.

$^1$H NMR (400 MHz, DMSO-d$_6$), δ9.84 (s, 1H), 8.70 (s, 1H), 8.11 (s, 1H), 7.98-8.01 (d, 2H), 7.81-7.85 (d, 1H), 2.87-2.90 (d, 2H), 2.50-2.51 (m, 1H), 2.20-2.34 (m, 6H), 1.78-1.98 (m, 8H), 1.69-1.75 (m, 6H).

MS (ESI): m/z 503.3[M+H]$^+$.

Example 45

N-(5-((1-methylpiperidin-4-yl)oxy)-pyridin-2-yl)-5-fluoro-4-(7'-fluoro-2'-methylspiro[cyclopentane-1,3'-indol]-5'-yl)pyrimidine-2-amino

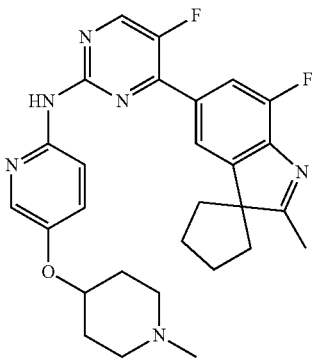 [SMILES: CC1=Nc2c(F)cc(-c3nc(Nc4ccc(OC5CCN(C)CC5)cn4)ncc3F)cc2C12CCCC2]

The intermediate 5'-(2-chloro-5-fluoropyrimidin-4-yl)-7'-fluoro-2'-methylspiro [cyclopentane-1,3'-indole] was prepared by the steps similar to those of Example 1.

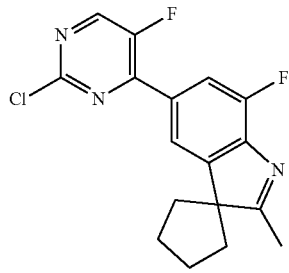 [SMILES: CC1=Nc2c(F)cc(-c3nc(Cl)ncc3F)cc2C12CCCC2]

Step 1: 1-Methylpiperidin-4-yl 4-methylbenzenesulfonate

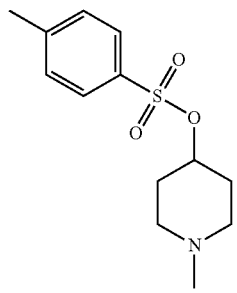 [SMILES: Cc1ccc(S(=O)(=O)OC2CCN(C)CC2)cc1]

4-Hydroxy-1-methylpiperidine (1000 mg, 8.69 mmol), p-toluenesulfonyl chloride (3310 mg, 17.38 mmol), dichloromethane (50 ml) and triethylamine (1 mL) were added to a reaction flask, and allowed to react at room temperature for 2 hours. Then, the reaction product was added with 50 ml of water and extracted three times with 30 ml of dichloromethane (30 ml for each time). The organic layers were combined, washed once with 50 mg of saturated salt solution, dried with anhydrous sodium sulfate, filtered and separated by column chromatography (dichloromethane/methanol=50:1) to give 1.87 g of intermediate, yield 80.0% (pale yellow solid).

Step 2: 2-bromo-5 ((1-methylpiperidin-4-yl) oxy) pyridine

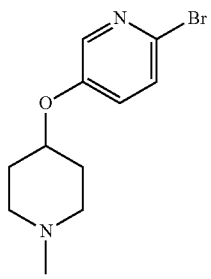

Intermediate 1-methylpiperidin-4-yl 4-methylbenzenesulfonate (1000 mg, 3.70 mmol), 2-bromo-5-hydroxypyridine (637 mg, 3.70 mmol), and DMF (50 ml) were added to a reaction flask, and the mixture was heated to 90° C. and reacted for 2 hours. The reaction product was added with 50 ml of water and extracted three times with dichloromethane (30 ml for each time). The organic layers were combined, washed once with 50 mg of saturated salt solution, dried with anhydrous sodium sulfate, filtered and separated by column chromatography (dichloromethane/methanol=40:1) to give 0.49 g of the intermediate (pale yellow solid), yield of 50.1%.

Step 3: 5 ((1-methylpiperidin-4-yl)oxy)-pyridin-2-amine

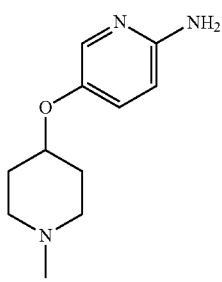

A reaction flask was charged with the intermediate 2-bromo-5-((1-methylpiperidin-4-yl)oxy)pyridine (1000 mg, 3.70 mmol), sodium bis(trimethylsilyl)amide (618 mg, 3.70 mmol), tetrahydrofuran (50 ml), 2-(dicyclohexylphosphino) biphenyl (120 mg, 0.37 mmol), and tris(dibenzylideneindeneacetone) dipalladium (338 mg, 0.37 mmol), and the mixture was heated to 65° C. and reacted for 12 hours. The reaction product was added with 50 ml of water, extracted three times with dichloromethane (30 ml for each time). The organic layers were combined, washed with 50 ml of saturated salt solution, dried with anhydrous sodium sulfate, filtered, and separated by column chromatography (dichloromethane/methanol=10:1) to give the intermediate (0.37 g, yellow solid), yield 49.3%.

Step 4

N-(5-((1-methylpiperidin-4-yl)oxy)-pyridin-2-yl)-5-fluoro-4-(7'-fluoro-2'-methylspiro[cyclopentane-1,3'-indole]-5'-yl)pyrimidine-2-amino was prepared by the method similar to Step 6 of Example 1.

$^1$H NMR (400 MHz, DMSO-d$_6$), δ9.69 (s, 1H), 8.63 (s, 1H), 7.93-7.99 (d, 1H), 7.80-7.83 (d, 1H), 7.81-7.85 (d, 1H), 7.12-7.14 (d, 1H), 5.76-5.82 (m, 1H), 5.02-5.13 (m, 2H), 3.79 (s, 2H), 2.56-2.59 (m, 13H), 2.28-2.33 (m, 6H), 1.74-1.99 (m, 2H).

MS (ESI): m/z 505.2[M+H]$^+$.

The control used in the following experimental examples with No. LY2835219 was prepared according to the preparation method of WO 2010075074, and its structural formula was as shown in the structural formula 3 in the background.

Experimental Example 1

Measurement of CDK kinase inhibitory activity of the compounds of this disclosure.

In vitro inhibitory effect of the compounds of the disclosure on CDK (CDK1, CDK4 and CDK6) kinase activity was tested by the following method.

1.1 Instrument and Kit Information

| Name | Type | Manufacturer |
| --- | --- | --- |
| Plate shaker | MTS2/4 | IKA |
| Microplate reader | M1000pro | TECAN |
| Centrifuge | Avanti J-26XP | Beckman Coulter |
| ADP-Glo ™ Kinase Assay + CDK1/CyclinA2 Kinase Enzyme System | V9211 | Promega |
| ADP-Glo ™ Kinase Assay + CDK4/CyclinE1 Kinase Enzyme System | V4489 | Promega |
| ADP-Glo ™ Kinase Assay + CDK6/CyclinD3 Kinase Enzyme System | V4511 | Promega |
| ADP-Glo ™ Kinase Assay + CDK9/CyclinK Kinase Enzyme System | V4105 | Promega |
| 5 × Reaction Buffer A | V307A-C | Promega |

1.2 Experimental Preparation 1.2.1 Preparation of Kinase Reaction Buffer I: The 5×Reaction Buffer A (Promega; V307A-C) provided in the kit was mixed and diluted with MILLI-Q® H$_2$O and 0.1 M DTT (dithiothreitol) to give 4× kinase buffer, and then MILLI-Q® H$_2$O was further added to finally formulate the solution into 1× Kinase buffer.

Preparation of kinase reaction buffer II: 0.5% DMSO (dimethyl sulfoxide) was added to the 1× kinase reaction buffer and mixed well.

1.2.2 Preparation of kinase solution: Kinase solutions having the concentrations required for each reaction system were prepared from 100 ng/μl kinase stock solution and the 1× kinase reaction buffer.

1.2.3 Preparation of the test compound solution and control LY2835219 solution:

(1) Preparation of control LY2835219 solution
  a. 1 μl of 10 mM standard substance stock solution was taken and added to 9 μl of kinase reaction buffer I and mixed well; then 90 μl of kinase reaction buffer I was added and mixed well; then 100 μl of kinase reaction buffer I was added and mixed well. The final concentration was 50 μM.
  b. 40 μl of kinase reaction buffer II was added into B2 to B10 of a 96-well plate, and 50 μl of the above solution was added into B1;

c. 10 µl of solution was taken from well B1, added into B2, and mixed well; then 10 µl of the resulting solution was taken and added into B3, and dilution was carried out in sequence to B9, so as to obtain control solutions that are diluted by 5-fold sequentially.

(2) Preparation of test compound solution:
a. Test compound solutions at a certain concentration were taken, respectively, diluted with kinase reaction buffer I to a final concentration of 50 µM compound solution;
b. 40 µl of kinase reaction buffer II was added into H2 to H10 of the 96-well plate; and 50 µl of the above solution was added into H1;
c. 10 µl of solution was taken from well H1, added into H2, and mixed well; then 10 µl of the resulting solution was taken and added into H3, and dilution was carried out in sequence to H9, so as to obtain test compound solutions that are diluted by 5-fold sequentially.

1.2.4 Preparation of a mixed solution of reaction substrate and ATP:
a. Preparation of ATP solution:
200 µl of 0.1 mM ATP solution: 2 µl of 10 mM ATP was added to 198 µl of kinase reaction buffer I;
300 µl of 50 µM ATP solution: 150 µl of kinase reaction buffer I was added to 150 µl of the above 0.1 mM ATP solution;
b. Preparation of 300 µl of reaction substrate solution:
150 µl 1 µg/µl reaction substrate stock solution was added to 150 µl kinase reaction buffer I, and mixed well;
c. The above a/b solutions were mixed to obtain mixed solutions, respectively.

1.3 Experimental process:
1.3.1: 2 µl of compound solutions of various concentrations were taken, added to a 384-well plate, and centrifuged 3 minutes;
1.3.2: 4 µl of kinase solution was added to each well, centrifuged at 5000 rpm and 18° C. for 10 minutes, and shaken on a plate shaker for 10 minutes;
1.3.3: 4 µl of mixed solution of substrate and ATP was added to each well, centrifuged at 5000 rpm and 18° C. for 10 minutes, and shaken on a plate shaker at 37° C. for 90 minutes;
1.3.4: The 384-well plate was taken out, and allowed to stand to room temperature;
1.3.5: 10 µl of ADP-GLO™ reagent was added to each well, centrifuged at 5000 rpm and 18° C. for 18 minutes, and shaken on a plate shaker at 25° C. for 40 minutes, and then the reaction was stopped;
1.3.6: 20 µl of kinase detection reagent was added to each well, centrifuged at 5000 rpm and 18° C. for 10 minutes, and shaken on a plate shaker at 25° C. for 30 minutes; and
1.3.7: M1000pro MICROPLATE READER was used to read fluorescence values.

1.4 Data Processing:
The inhibition rate of each compound at each concentration point was calculated by the formula as follows and curve fitting was performed by GraphPad Prism 5 software to obtain the $IC_{50}$ value.

Inhibition rate at each concentration point $(inh\ \%) =$ $$\frac{\text{fluorescence value at zero point concentration} - \text{fluorescence value at each concentration point}}{\text{fluorescenece value at zero concentration}} \times 100\%$$

1.5 Test Results:
The inhibitory effects of LY2835219 disclosed by WO 2010075074 and the compounds of Examples 1-43 on CDK1/CyclinA2 and CDK6/CyclinD3 are expressed by $IC_{50}$, and the specific results are shown in Table 1.

TABLE 1

Detection results of inhibitory activity of test compounds on CDK1/CyclinA2 and CDK6/CyclinD3 ($IC_{50}$: nM)

| Examples | CDK1/CyclinA2 | CDK6/CyclinD3 | CDK1/CDK6 |
|---|---|---|---|
| LY2835219 | 319.43 | 3.81 | 83.83 |
| 1 | 2223.92 | 43.03 | 51.68 |
| 2 | — | 158.7 | — |
| 3 | 1678 | 79.06 | 21.22 |
| 4 | — | 2147 | — |
| 5 | 438.5 | 7.528 | 58.23 |
| 6 | 152.2 | 6.45 | 23.59 |
| 7 | 83.83 | 3.26 | 25.71 |
| 8 | — | 85.77 | — |
| 9 | 268.28 | 20.42 | 13.13 |
| 10 | 435.68 | 47.11 | 9.25 |
| 11 | 110.06 | 5.62 | 19.58 |
| 12 | 1071.23 | 3.78 | 283.33 |
| 13 | 327.00 | 0.39 | 838.46 |
| 14 | 233.64 | 4.07 | 57.40 |
| 15 | 26.92 | 4.31 | 6.25 |
| 16 | 95.70 | 9.02 | 10.61 |
| 17 | 2707.11 | 0.73 | 3708.37 |
| 18 | 189.86 | 2.74 | 69.29 |
| 19 | 64.82 | 65.49 | 0.99 |
| 20 | 1444.45 | 87.60 | 16.49 |
| 21 | 135.19 | 27.67 | 4.89 |
| 22 | 915.35 | 52.50 | 17.43 |
| 23 | 50.27 | 4.53 | 11.10 |
| 24 | 76.44 | 12.86. | 5.94 |
| 25 | 417.16 | 8.78 | 47.51 |
| 26 | 216.08 | 12.51 | 17.27 |
| 27 | 1160.23 | 16.21 | 71.57 |
| 28 | 328.47 | 6.24 | 52.63 |
| 29 | 82.42 | 3.145 | 26.20 |
| 30 | 176.58 | 0.49 | 360.37 |
| 31 | — | 58.84 | — |
| 32 | 142.03 | 10.14 | 14.01 |
| 33 | 166.28 | 15.61 | 10.65 |
| 34 | 111.59 | 5.13 | 21.75 |
| 35 | 64.03 | 8.74 | 7.33 |
| 36 | 100.9 | 3.79 | 26.65 |
| 37 | 73.67 | 22.87 | 3.22 |
| 38 | 19.83 | 0.20 | 99.15 |
| 39 | 38.51 | 5.65 | 6.82 |
| 40 | 161.60 | 24.97 | 6.47 |
| 41 | | 76.65 | |
| 42 | 3681.98 | 2.33 | 1580.25 |
| 43 | 268.90 | 0.90 | 298.78 |
| 44 | — | 37.5 | — |
| 45 | — | 43.9 | — |

The inhibitory effects of some representative compounds of the disclosure on CDK9/CyclinD3, Pim-1 and CDK2/CyclinE1 and CDK4/CyclinE1 are shown in Table 2, Table 3 and Table 4, respectively.

TABLE 2

Detection results of inhibitory activity of some test compounds on CDK9/CyclinD3 (IC$_{50}$: nM)

| Examples | CDK1/CyclinA2 | CDK6/CyclinD3 | CDK9/CyclinD3 | CDK1/CDK6 | CDK9/CDK6 |
|---|---|---|---|---|---|
| LY2835219 | 319.43 | 3.81 | 5.08 | 83.83 | 1.33 |
| 1 | 2223.92 | 43.03 | 244.97 | 51.68 | 5.69 |
| 3 | 1678 | 79.06 | 50.02 | 21.22 | 0.63 |
| 6 | 152.2 | 6.45 | 0.42 | 23.59 | 0.06 |
| 7 | 83.83 | 3.26 | 4.58 | 25.71 | 1.40 |
| 9 | 268.28 | 20.42 | 14.43 | 13.13 | 0.71 |
| 10 | 435.68 | 47.11 | 27.04 | 9.25 | 0.57 |
| 12 | 1071.23 | 3.78 | 57.19 | 283.33 | 18.75 |
| 13 | 327.00 | 0.39 | 2.56 | 838.46 | 6.56 |
| 16 | 95.70 | 9.02 | 16.37 | 10.61 | 1.81 |
| 17 | 2707.11 | 0.73 | 5.36 | 3708.37 | 7.33 |
| 18 | 189.86 | 2.74 | 1.00 | 69.29 | 0.36 |
| 20 | 1444.45 | 87.60 | 0.24 | 16.49 | 0.003 |
| 22 | 915.35 | 52.50 | 0.50 | 17.43 | 0.009 |
| 24 | 76.44 | 12.86. | 1.74 | 5.94 | 0.13 |
| 25 | 417.16 | 8.78 | 1.09 | 47.51 | 0.12 |
| 26 | 216.08 | 12.51 | 10.95 | 17.27 | 0.88 |
| 27 | 1160.23 | 16.21 | 2.83 | 71.57 | 0.17 |
| 28 | 328.47 | 6.24 | 0.96 | 52.63 | 0.15 |
| 30 | 176.58 | 0.49 | 0.43 | 360.37 | 0.88 |

TABLE 3

Detection results of inhibitory activity of some test compounds on Pim-1 (IC$_{50}$: nM)

| Examples | CDK1/CyclinA2 | CDK6/CyclinD3 | CDK9/CyclinD3 | Pim-1 | CDK1/CDK6 | CDK9/CDK6 | Pim-1/CDK6 |
|---|---|---|---|---|---|---|---|
| LY2835219 | 319.43 | 3.81 | 5.08 | 3.92 | 83.83 | 1.33 | 1.03 |
| 1 | 2223.92 | 43.03 | 244.97 | 220.42 | 51.68 | 5.69 | 5.12 |
| 3 | 1678 | 79.06 | 50.02 | 197.8 | 21.22 | 0.63 | 2.50 |
| 6 | 152.2 | 6.45 | 0.42 | 15.09 | 23.59 | 0.06 | 2.33 |
| 7 | 83.83 | 3.26 | 4.58 | 461.39 | 25.71 | 1.40 | 141.53 |
| 9 | 268.28 | 20.42 | 14.43 | 173.89 | 13.13 | 0.71 | 8.51 |
| 12 | 1071.23 | 3.78 | 57.19 | 15.11 | 283.33 | 18.75 | 3.99 |
| 13 | 327.00 | 0.39 | 2.56 | 2.22 | 838.46 | 6.56 | 5.69 |
| 14 | 233.64 | 4.07 | — | 28.65 | 57.40 | — | 7.03 |
| 16 | 95.70 | 9.02 | 16.37 | 686.40 | 10.61 | 1.81 | 76.10 |
| 17 | 2707.11 | 0.73 | 5.36 | 38.27 | 3708.37 | 7.33 | 52.43 |
| 24 | 76.44 | 12.86 | 1.74 | 72.81 | 5.94 | 0.13 | 5.66 |

TABLE 4

Inhibitor effect of a part of test compounds on CDK4 and CDK2 (IC$_{50}$: nM)

| Examples | CDK1/CyclinA2 | CDK2/CyclinE1 | CDK4/CyclinE1 | CDK6/CyclinD3 | CDK9/CyclinD3 | Pim-1 | CDK1/CDK6 | CDK9/CDK6 | Pim-1/CDK6 |
|---|---|---|---|---|---|---|---|---|---|
| LY2835219 | 319.43 | 769.22– | 14.83 | 3.81 | 5.08 | 3.92 | 83.83 | 1.33 | 1.03 |
| 6 | 152.2 | — | 80.9 | 6.45 | 0.42 | 15.09 | 23.59 | 0.06 | 2.33 |
| 12 | 1071.23 | 394.21 | 4.46 | 3.78 | 57.19 | 15.11 | 283.33 | 18.75 | 3.99 |
| 17 | 2707.11 | 2320.88 | 2.62 | 0.73 | 5.36 | 38.27 | 3708.37 | 7.33 | 52.43 |

1.6 Test Conclusion:

1) The compounds of this disclosure have significant inhibitory effect on CDK6 and CDK4.

2) CDK1/CDK6, CDK9/CDK6 and Pim-1/CDK6 can reflect the selectivity of the compound for protein kinases. The larger the number, the better the selectivity of the compound for CDK6, which indicates that the toxicity of the compound for inhibiting pan-kinase may be smaller. The control compound (LY2835219) exhibits CDK1/CDK6=83.83, CDK9/CDK6=1.33, and Pim-1/CDK6=1.03; some of the compounds of the disclosure show better selectivity than LY2835219, especially the compound prepared in Example 17 shows higher enzymatic activity for CDK6 and better selectivity for CDK1, CDK9 and Pim-1.

Experimental Example 2

Measurement of Inhibitory Effect of Representative Compounds of the Present Disclosure on Proliferation of Human Breast Cancer Cell MDB-MA-231

2.1 Experimental Materials: Human breast cancer cells MDA-MB-231 purchased from the Cell Resource Center of Peking Union Medical College, DAPI (5 mg/mL, Beyotime, c1002), 4% paraformaldehyde (DINGGUO BIOTECH- NOLOGY CO. LTD, AR-0211), 96-well plate with black transparent bottom (PE, 6005182), In Cell Analyzer 2200 (GE Healthcare).

2.2 Experimental Preparation:

2.2.1 Preparation of human breast cancer cell MDA-MB-231 medium: RPIM1640+10% FBS+1% penicillin/streptomycin.

2.2.2 Preparation of test compound solutions and solutions of standard LY2835219:

(1) Preparation of solutions of standard LY2835219
   a. 3.6 µl of 10 mM standard stock solution was taken, added to 6.4 µl medium, and mixed well; then 90 µl of medium was added and mixed well; then 200 µl of medium was added, and mixed well to give an initial concentration of 20 mM;
   b. 200 µl of medium containing 0.2% DMSO (dimethylsulfoxide) was added into B2 to B10 of a 96-well plate; 300 µl of the above solution was added into B1; and
   c. 100 µl of solution was taken from well B1, added into B2, and mixed well; then 100 µl of the resulting solution was taken and added into B3, and dilution was carried out in sequence to B9, so as to obtain standard solutions diluted by 3-fold sequentially.

(2) Preparation of Test Compound Solutions
   a. Test compound solution at a certain concentration was taken, and diluted with a medium to give a compound solution with a final concentration of 20 µM;
   b. 200 µl of medium containing 0.2% DMSO (dimethylsulfoxide) was added into H2 to H10 of the 96-well plate; and 300 µl of the above solution was added into H1; and
   c. 100 µl of solution was taken from well H1, added into H2, and mixed well; then 100 µl of the resulting solution was taken and added into H3, and dilution was carried out in sequence to B9, so as to obtain test compound solutions diluted by 3-fold sequentially.

2.3 Experimental Process:

2.3.1: MDA-MB-231 cells were inoculated into a 96-well cell plate with black transparent bottom at 4000 cells/100 µl/well, and cultured overnight at 37° C.;

2.3.2: The above samples were added at 100 µl/well to a culture plate inoculated with cells, gently patted to mix well, and incubated at 37° C. for 72 hours;

2.3.3: Fixation: the cell plate was taken out, the medium was removed, and 50 µl of 4% paraformaldehyde was added per well to fix for 10 minutes;

2.3.4: 50 µl of 0.1M glycine was added to neutralize for 10 minutes;

2.3.5: 1×PBS (phosphate buffer pH 7.2) was used to wash twice;

2.3.6: Permeabilization: 50 µl of 0.2% TRITON-X®100 (Triton) was added per well, and permeabilization was carried out at room temperature for 10 minutes;

2.3.7: 1×PBS (Phosphate buffer pH 7.2) was used to wash twice;

2.3.8: 5 mg/mL DAPI stock solution was diluted at a ratio of 1:5000 (final concentration of 1 µg/ml), and staining was performed at room temperature for 20 minutes;

2.3.9: 1×PBS (Phosphate buffer pH 7.2) was used to wash three times; and 2.3.10: Scanning and analysis were performed by an IN cell analyzer 2200.

2.4 Data Processing:

The inhibition rate of each compound at each concentration point was calculated by the formula as follows and curve fitting was performed by GraphPad Prism 5 software to obtain the $IC_{50}$ value.

$$\text{Inhibition rate at each concentration point } (inh \%) = \frac{\text{cell value at zero point concentration} - \text{cell value at each concentration point}}{\text{cell value at zero point concentration}} \times 100\%$$

2.5 Determination Results:

The detection results of the cytological activity of LY2835219 disclosed by WO 2010075074 and the compounds of Examples 12 and 17 were expressed by $IC_{50}$, and the specific results are shown in Table 5.

TABLE 5

Inhibitory activity of the representative compounds of this disclosure on the proliferation of human breast cancer cell MDB-MA-231 ($IC_{50}$: nM)

| Examples | $IC_{50}$ |
|---|---|
| LY2835219 | 229.05 |
| 12 | 182.72 |
| 17 | 109.82 |

2.6 Experimental Conclusion:

The compounds of Examples 12 and 17 have significant inhibitory activity on proliferation of the MDA-MB-231 cell line, and the representative compounds of this disclosure have a higher proliferation inhibitory activity relative to the control compound LY2835219.

Experimental Example 3

Rat Pharmacokinetic Determination of Representative Compounds of the Present Disclosure 3.1 Experimental Summary SD rats were used as the test animals, and the concentrations of the drugs in the plasma of rats at different time points after the intravenous administration and intragastric administration of the representative compounds were determined by LC/MS/MS, so as to study the pharmacokinetic behavior of the compounds of the disclosure in rats and evaluate the pharmacokinetic characteristics thereof.

3.2 Experimental Scheme 3.2.1 Test drugs:

The compound prepared in Example 17 of this disclosure. Control drug LY2835219, prepared by ourselves.

3.2.2 Test animals:

Twelve health adult SD rats, male, 6-8 weeks old, weighing 200-250 g, purchased from Zhaoyan (Suzhou) New Drug Research Center Co., Ltd., Animal Production License No: SCXK (Su) 2013-0003.

3.2.3 Preparation of the test drugs

Intragastric administration: An appropriate amount of sample was weighed, and added with 0.1% hydroxyethyl cellulose/0.5% TWEEN®80 to a final volume to give 1 mg/ml solution.

Intravenous injection: An appropriate amount of sample was weighed, and added with 10% of N-methyl-2-pyrrolidone and 90% of 18% sulfobutyl-β-cyclodextrin to a final volume to give 0.4 mg/ml solution for intravenous injection.

3.2.4 Administration of the test drugs

Intravenous administration: for each test compound, 3 male SD rats were administered intravenously at a dose of 2 mg/kg and administration volume of 1 ml/kg after fasting overnight.

Intragastric administration: for each test compound, 3 male SD rats were administrated intragastrically at a dose of 5 mg/kg and an administration volume of 5 ml/kg after fasting overnight.

3.3 Experimental Operation

Before administration and 0.0833, 0.25, 0.5, 1, 2, 4, 8, 12 and 24 hours after administration, blood was taken through the carotid artery cannula. Whole blood was anticoagulated with EDTA-K2 and centrifuged, the supernatant was removed, and the residue was frozen at −20° C. until sample analysis. Plasma samples were analyzed by LC-MS/MS, sample pretreatment was performed using a protein precipitation method, the linear range of sample analysis was 1-2000 ng/ml, and the lowest quantification limit was 1 ng/ml.

3.4 Pharmacokinetic Data Results

The pharmacokinetic parameters of the compounds of this disclosure are shown in Table 6 and Table 7.

TABLE 6

PK parameters of compound 17 of the present disclosure in rats undergoing single intravenous administration (Mean ± SD)

| PK parameters | LY2835219 | Example 17 |
|---|---|---|
| Half life T1/2(hr) | 3.69 ± 1.40 | 8.67 ± 4.98 |
| Area under curve $AUC_{0-t}$(ng · hr/mL) | 1499 ± 337.3 | 1018 ± 239 |
| Area under curve $AUC_{0-\infty}$(ng · hr/mL) | 1535 ± 346.9 | 1220 ± 456 |
| Apparent volume of distribution $V_Z$(L/Kg) | 6.95 ± 2.43 | 19.42 ± 5.89 |
| Clearance rate Cl (mL/min/kg) | 22.4 ± 4.49 | 30.0 ± 11.1 |
| Retention time MRT(hr) | 3.82 ± 1.44 | 7.78 ± 1.30 |

TABLE 7

PK parameters of compound 17 of this disclosure in rats undergoing single intragastric administration (Mean ± SD)

| PK parameters | LY2835219 | Example 17 |
|---|---|---|
| Half life T1/2(hr) | 4.07 | 2.00 |
| Blood concentration $C_{max}$(ng/mL) | 312 ± 33.0 | 188 ± 75 |
| Area under curve $AUC_{0-t}$(ng · hr/mL) | 3275 ± 731 | 2608 ± 1217.8 |
| Area under curve $AUC_{0-\infty}$(ng · hr/mL) | 3438 | 5256 |
| Retention time MRT(hr) | 7.97 ± 1.17 | 10.21 ± 0.27 |
| Bioavailability(%) | 87.4 | 102.5 |

3.5 Experimental Conclusion: The representative compound of the disclosure (prepared in Example 17) has higher bioavailability in rats relative to compound LY2835219, and has a good oral absorbing effect.

Experimental Example 4

Pharmacokinetic Determination of Representative Compounds of this Disclosure in Mouse 4.1 Experimental Summary The ICR mice were used as the test animals, and the concentrations of the drugs in the plasma of mice at different time points after intragastric administration and intravenous administration of the representative compound of the present disclosure were determined by LC/MS/MS, so as to study the pharmacokinetic behavior of the compounds of the disclosure in mice and evaluate the pharmacokinetic characteristics thereof.

4.2 Experimental Scheme 4.2.1 Test drugs:

The compound prepared in Example 17 of the disclosure. Control drug LY2835219, prepared by ourselves.

4.2.2 Test animals:

Twelve health adult ICR mice, males, 6-8 weeks old, weighing 20-25 g, purchased from Zhaoyan (Suzhou) New Drug Research Center Co., Ltd. Animal Production License No. SCXK (Su) 2013-0003.

4.2.3 Preparation of the test drugs

An appropriate amount of sample was weighed, and added with 0.1% hydroxyethyl cellulose/0.5% TWEEN®80 to a final volume to give 0.5 mg/ml solution for intragastric administration.

An appropriate amount of sample was weighed, and added with 10% of N-methyl-2-pyrrolidone and 90% of 18% sulfobutyl-β-cyclodextrin to a final volume to give 0.2 mg/ml solution for intravenous administration.

4.2.4 Administration of the test drugs

For each test drug, 3 male ICR mice were administered intragastrically at a dose of 5 mg/kg and administration volume of 10 ml/kg after fasting overnight.

For each test drug, 3 male ICR mice were administered intravenously at a dose of 2 mg/kg and administration volume of 10 ml/kg after fasting overnight.

4.3 Experimental Operation

Before administration and 0.25, 0.5, 1, 2, 4, 8, 12 and 24 hours after administration, blood of the intragastrically administered group was taken through carotid artery cannula. Whole blood was anticoagulated with EDTA-K2 and centrifuged, the supernatant was removed, and the residue was frozen at −20° C. until sample analysis. Before administration and 0.083, 0.25, 0.5, 1, 2, 4, 8, 12 and 24 hours after administration, blood of the intravenously administered group was taken through carotid artery cannula. The plasma samples were treated in the same manner as that employed for plasma samples of the intragastrically administered group. Plasma samples were analyzed by LC-MS/MS, sample pretreatment was performed using protein precipitation method, the linear range of sample analysis was 1-2000 ng/ml, and the lowest quantification limit was 1 ng/ml.

4.4 Pharmacokinetic data results: see Table 8 and Table 9.

TABLE 8

PK parameters of compound 17 of this disclosure in mice undergoing single intravenous administration (Mean ± SD)

| PK parameters | LY2835219 | Example 17 |
|---|---|---|
| Half life T1/2(hr) | 1.68 ± 0.10 | 9.1 ± 0.26 |
| Area under curve $AUC_{0-t}$(ng · hr/mL) | 674 ± 82.1 | 1137 ± 77.8 |
| Area under curve $AUC_{0-\infty}$(ng · hr/mL) | 679 ± 81.0 | 1327 ± 4 |
| Apparent volume of distribution $V_Z$(L/Kg) | 7.21 ± 1.08 | 19.8 ± 0.81 |
| Clearance rate Cl (mL/min/kg) | 49.6 ± 5.72 | 25.2 ± 1.72 |
| Retention time MRT(hr) | 1.64 ± 0.17 | 7.51 ± 0.28 |

TABLE 9

PK parameters of compound 17 ofin mice undergoing single intragastric administration (Mean ± SD)

| PK parameters | LY2835219 | Example 17 |
|---|---|---|
| Half life T1/2(hr) | 1.70 ± 0.02 | 8.38 ± 3.16 |
| Blood concentration $C_{max}$(ng/mL) | 154 ± 6.4 | 134 ± 11.8 |
| Area under curve $AUC_{0-t}$(ng · hr/mL) | 756 ± 34 | 2134 ± 96.9 |
| Area under curve $AUC_{0-\infty}$(ng · hr/mL) | 765 ± 34 | 2504 ± 387 |

TABLE 9-continued

PK parameters of compound 17 ofin mice undergoing single intragastric administration (Mean ± SD)

| PK parameters | LY2835219 | Example 17 |
|---|---|---|
| Retention time MRT(hr) | 3.08 ± 0.02 | 9.45 ± 1.05 |
| Bioavailability(%) | 45.1 | 75.1 |

4.5 Experimental Conclusion: The representative compound 17 of the present disclosure has higher bioavailability and longer half-life in mice relative to the compound LY2835219, and has a good oral absorbing effect.

Experimental Example 5

Determination of plasma and brain exposure levels of the representative compound 17 of the disclosure.
5.1 Experimental Summary
The CD-1 mice were used as the test animals, the concentrations of the drugs in the plasma and brain tissue of mice at different time points after single intragastric administration of the representative compound of this disclosure were determined by LC/MS/MS, so as to study the plasma level and brain exposure level of the compounds of the disclosure in mice.
5.2 Experimental Scheme
5.2.1 Test drugs:
The compound prepared in Example 17 of this disclosure. Control drug LY2835219, prepared by ourselves.
5.2.2 Test animals:
Twenty-four health adult CD-1 mice, male, 6-8 weeks old, body weight 20-25 g, purchased from Shanghai SIPPR-BK Laboratory Animal Co., Ltd., Animal Production License No: SCXK (Shanghai) 2013-0016.
5.2.3 Preparation of the test drugs
An appropriate amount of sample was weighed, and added with 0.1% hydroxyethylcellulose/0.5% TWEEN®80 to a final volume to give 1.0 mg/ml solution.
5.2.4 Administration of test drug
For each test drug, 12 male CD-1 mice were administered intragastrically at a dose of 10 mg/kg and an administration volume of 10 ml/kg after fasting overnight.
5.3 Experimental Operation
LY2835219: Before administration and 0.25, 1.5 and 6 hours after administration, blood was taken through carotid artery cannula, and three mice were killed at the same time. The whole brain was collected, mashed and frozen in liquid nitrogen. Ten hours after administration, the remaining animals were sacrificed, whole blood was collected by cardiac puncture, and the whole brain was collected, mashed and frozen in liquid nitrogen.
Example 17: Before administration and 2, 4 and 24 hours after administration, blood was taken through carotid artery cannula, and three mice were killed at the same time. The whole brain was collected, mashed and frozen in liquid nitrogen. 48 hours after administration, the remaining animals were sacrificed, whole blood was collected by cardiac puncture, and the whole brain was collected, mashed and frozen in liquid nitrogen.
Treatment of the whole blood sample: The collected whole blood was anticoagulated with EDTA-K2, and centrifuged, the supernatant was removed, and the residue was frozen and stored at −20° C. until the sample was analyzed by LC-MS/MS.
Brain homogenate sampling: Brain homogenate were dispersed with PBS (pH=7.4): MeOH (v:v, 2:1) solution in a volume 5 times of the volume of the brain homogenate. 100 μl of solution was taken, and the protein therein was precipitated with 600 μl IS. The mixture was centrifuged at 13,000 rpm and 20-25° C. for 15 minutes. 50 μL of the supernatant was mixed with 150 μL of water containing 0.3% FA and centrifuged at 4° C. 5 μL of the sample was analyzed by LC-MS/MS.
The linear range of sample analysis was 1-2000 ng/ml, and the lowest quantification limit was 1 ng/ml.
5.4 Measurement results of blood brain exposure level are shown in Table 10.

TABLE 10

Mean exposure of test compound in plasma and brain of CD-1 mice

| Parameters | | LY2835219 | 17 |
|---|---|---|---|
| Blood concentration | Plasma | 836 | 639 |
| $C_{max}$(ng/mL) | Brain | 188 | 1270 |
| | Brain/Plasma | 0.22 | 1.98 |
| The time for blood | Plasma | 1.50 | 4.00 |
| concentration reaching peak $T_{max}$ (h) | Brain | 6.00 | 4.00 |
| Area under curve | Plasma | 4247 | 7661 |
| $AUC_{0-last}$(ng · hr/mL) | Brain | 1113 | 16786 |
| | Brain/Plasma | 0.28 | 2.19 |

5.5 Experimental Conclusion: The representative compound of the disclosure (prepared in Example 17) has better blood brain distribution, higher $AUC_{0-last}$ ratio (brain/plasma) and higher $C_{max}$ ratio (brain/plasma) relative to compound LY2835219, and the $T_{max}$ in the brain equals to $T_{max}$ in plasma, indicating that the drug has similar PK behavior in the brain and plasma. It is suggested that the compounds of this disclosure can cross the blood-brain barrier to inhibit the growth of brain tumors (brain cancer) and treat brain cancer.

Experimental Example 6

Determination of inhibitory effect of the representative compound 17 of the disclosure on proliferation of the U87 MG cell line.
6.1 Experimental Materials:
Human glioma cell line U87 MG was purchased from the Cell Bank of Chinese Academy of Sciences, Shanghai, DAPI (5 mg/mL, Beyotime, c1002), 4% paraformaldehyde (DINGGUO BIOTECHNOLOGY CO. LTD AR-0211), 96-well plate with black transparent bottom (PE, 6005182), IN Cell Analyzer 2200 (GE Healthcare).
6.2 Experimental Preparation:
6.2.1 Preparation of U87 MG medium: RPIM1640+10% FBS+1% penicillin/streptomycin.
6.2.2 Preparation of test compound solutions and solutions of standard LY2835219:
(1) Preparation of solutions of standard LY2835219
  a. 3.6 μl of 10 mM standard stock solution was taken, added with to 6.4 μl medium, and mixed well; then 90 μl of medium was added, and mixed well; then 200 μl of medium was added, and mixed well to give an initial concentration of 20 μM
  b. 200 μl of medium containing 0.2% DMSO (dimethylsulfoxide) was added into B2 to B10 of a 96-well plate; 300 μl of the above solution was added into B1;
  c. 100 μl of solution was taken from well B1, added into B2, and mixed well; then 100 μl of the resulting solution was taken and added into B3, and dilution was carried out in sequence to B9, so as to obtain standard solutions diluted by 3-fold sequentially.

(2) Preparation of test compound solutions:
a. Test compound solution at a certain concentration was taken, and diluted with a medium to give a compound solution with a final concentration of 20 μM;
b. 200 μl of medium containing 0.2% DMSO (dimethylsulfoxide) was added into H2 to H10 of the 96-well plate; and 300 μl of the above solution was added into H1;
c. 100 μl of solution was taken from well H1, added into H2, and mixed well; then 100 μl of the resulting solution was taken and added into H3, and dilution was carried out in sequence to H9, so as to obtain test compound solutions diluted by 3-fold sequentially.

6.3 Experimental Process:
6.3.1: U87 MG cells were inoculated into a 96-well plate with black transparent bottom at 4000 cells/100 μl/well, and cultured at 37° C. overnight;
6.3.2: The above samples were added at 100 μl/well to a culture plate inoculated with cells, gently patted to mix well, and incubated at 37° C. for 72 hours;
6.3.3: Fixation: the cell plate was taken out, the medium was removed, and 50 μl of 4% paraformaldehyde was added per well to fix for 10 minutes;
6.3.4: 50 μl of 0.1 M glycine was added to neutralize for 10 minutes;
6.3.5: 1×PBS (phosphate buffer pH 7.2) was used to wash twice;
6.3.6: Permeabilization: 50 μl of 0.2% TRITON-X®-100 (Triton) was added per well, and permeabilization was carried out at room temperature for 10 minutes;
6.3.7: 1×PBS (Phosphate buffer pH 7.2) was used to wash twice;
6.3.8: 5 mg/mL DAPI stock solution was diluted at a ratio of 1:5000 (final concentration of 1 μg/ml), and staining was performed at room temperature for 20 minutes;
6.3.9: 1×PBS (Phosphate buffer pH 7.2) was used to wash three times; and
6.3.10: Scanning and analysis were performed by In cell analyzer.

6.4 Data Processing:
The inhibition rate of each compound at each concentration point was calculated by the formula as follows and curve fitting was performed by GraphPad Prism 5 software to obtain the $IC_{50}$ value.

$$\text{Inhibition rate at each concentration point } (inh\ \%) = \frac{\text{cell value at zero point concentration} - \text{cell value at each concentration point}}{\text{cell value at zero point concentration}} \times 100\%$$

6.5 Determination Results:
The detection results of the cytological activity of LY2835219 disclosed by WO2010075074 and the compound of Example 17 were expressed by $IC_{50}$, and the specific results are shown in Table 11.

TABLE 11

Inhibitory activity of the representative compound of the disclosure on the proliferationof U87MG Cell Line ($IC_{50}$: nM)

| Examples | $IC_{50}$ |
|---|---|
| LY2835219 | 150.70 |
| 17 | 35.43 |

6.6 Experimental Conclusion:
The compound of Example 17 has significant inhibitory activity on proliferation of the U87MG cell line, and the representative compound of this disclosure has a higher proliferation inhibitory activity relative to the control compound LY2835219.

Experimental Example 7

Pharmacodynamic study of the compound 17 of this disclosure and the combination of compound 17 of the disclosure and temozolomide in a U87-luc orthotopic brain xenograft model 7.1 Experimental Summary
Adult female BALB/c nude mice were used as test animals. A U87-luc orthotopic brain xenograft model was used to study the effect of representative compound 17 of this disclosure on the median survival of female BALB/c nude mice after intragastric administration.

7.2 Experimental Scheme
7.2.1 Test drugs:
The compound prepared in Example 17 of the disclosure.
Control drug LY2835219, made by ourselves.
Temozolomide was purchased from Selleck Chemicals.
7.2.2 Test animals:
Healthy adult female BALB/c nude mice, 8 mice/group, 6-8 weeks old, weighing 18-22 g, purchased from Shanghai SIPPR-BK Laboratory Animal Co., Ltd., Animal Production License No: 2008001658261; 2008001658263.
7.2.3 Preparation of the test compounds
An appropriate amount of compound 17 was weighed, and added with 0.1% hydroxyethyl cellulose/0.5% TWEEN®80 as vehicle to 0.3125 mg/ml;
An appropriate amount of Temozolomide sample was weighed, and added with 0.1% CMC-Na+0.25% TWEEN®80 as vehicle to 0.3 mg/ml.
7.3 Orthotopic Brain Xenograft Model
Adult female BALB/c nude mice were anesthetized by intraperitoneal injection of sodium pentobarbital at a dose of 80 mg/kg. To relieve pain, animals were injected subcutaneously with buprenorphine at the time points 30 minutes before operation and 6 hours after operation at a dose of 0.1 mg/kg. Animals were observed after anesthesia until all animals had awakened.
The anesthetized animals were properly fixed, the animals' head skin was sterilized with 70% ethanol, and an approximately 10 mm long incision was made on the right side of the midline from the forehead to the ear line. $3 \times 10^5$ U87-luc cells (3 μl, mixture of PBS and Matrigel at a ratio of 4:1) were inoculated at the right frontal lobe that is 2 mm away from the right side of the bregma and is 1 mm away from the front side of the coronal suture in each animal. The incision was sutured with a No. 6 suture, and sterilized with polyvinylpyrrolidone. Animals are kept warm until anabiosis. Six days after tumor cell transplantation, tumor animals were grouped by stratified randomization based on fluorescence signal intensity values, and the average bioluminescence reached 2.812E+07 photons/sec when the groups were administered in groups. Different animal groups were administered at different doses for a total of 35 days.

7.4 Median survival (days) of the compound 17 of this disclosure and the combination of compound 17 of the present invention with Temozolomide in a U87-luc orthotopic brain xenograft model.

TABLE 12

Median survival caused by the compound 17 and the combination of compound 17 with temozolomide

| Groups | Medium survival (days) | P value[b] | P value[c] |
|---|---|---|---|
| Vehicle | 30(29-37)[a] | — | — |
| Compound 17 3.125 mg/kg QD | 38.5(26-59) | 0.0822 | — |
| Compound 17 6.25 mg/kg QD | 43.5(31-48) | 0.0007 | — |
| Compound 17 12.5 mg/kg QD | 44.5(31-114) | 0.0004 | — |
| Compound 17 25 mg/kg QD | 61(41-76) | <0.0001 | — |
| Compound 17 50 mg/kg QD | 78.5(63->114) | <0.0001 | — |
| Temozolomide 3 mg/kg IP Day 0, 7, 14, 21 and 28 | 47(38-83) | <0.0001 | — |
| Compound 17 6.25 mg/kg QD + Temozolomide 3 mg/kg IP Day 0, 7, 14, 21 and 28 | 57(42->114) | <0.0001 | 0.0454 |

[a]Survival time range.
[b]p values when each group was compared with Vehicle group.
[c]p values when each group was compared with temozolomide single-dose group.

7.5 Experimental Conclusion: The representative compound 17 of the present disclosure can significantly prolong the median survival of animals in a U87-luc orthotopic brain xenograft model in a dose-dependent manner. In the study on combined medication with temozolomide, the combined medication further prolongs the median survival of the animals compared to temozolomide used alone.

In summary, the disclosure provides a series of novel compounds having selective CDK4/6 kinase inhibitory activity which is superior to, or comparable to, that of LY2835219, a candidate drug presently in Phase III clinical trials, with some of the compounds exhibiting better selectivity. Moreover, the preferred compound exhibits good oral absorbing effect, and good blood-brain distribution, and has significant pharmacological effect on the U87-luc orthotopic brain xenograft model, suggesting that the compounds of this disclosure are promising to be developed into new drugs for the treatment of diseases related with cell proliferation, in particular malignant tumors, especially brain cancers, and to offer new options for clinicians and patients.

Kits

The disclosure also provides a kit comprising the compounds of structural formulas I-V and VIII or their respective tautomer, mesomer, racemate, enantiomers, diastereomer, deuterated compound, prodrug, or mixture thereof, or pharmaceutically acceptable salts or solvates of the compounds of structural formulas I-V and VIII, or their respective tautomer, mesomers, racemate, enantiomer, diastereomer deuterated compound, prodrug or mixture thereof.

In addition, the kit may further comprise operation instruction.

Pharmaceutical Compositions

This disclosure also relates to a combination product for treating a cell proliferative disorder, wherein the combination product comprises a pharmaceutically acceptable carrier, and the compounds of structural formulas I-V and VIII, or their respective tautomer, mesomer, racemate, enantiomer, diastereomer, deuterated compound, prodrug, or mixture thereof; or pharmaceutically acceptable salts or solvates of the compounds of formulas I-V and VIII or their respective tautomer, mesomer, racemate, enantiomer, diastereomer, deuterated compound, prodrug or mixture thereof. The compounds or their respective tautomer, mesomer, racemate, enantiomer, diastereomer, deuterated compound, prodrug, or mixture thereof or pharmaceutically acceptable salts or solvates of the compounds of formulas I-V and VIII or their respective tautomer, mesomer, racemate, enantiomer, diastereomer, deuterated compound, prodrug or mixture may be in an effective amount or a therapeutically effective amount in the pharmaceutical composition.

As used herein, "an effective amount" refers to an amount that is functional and active to humans and/or animals and acceptable to humans and/or animals.

As used herein, "pharmaceutically acceptable" ingredients are suitable for use in humans and/or animals (such as mammals or birds) without undue adverse side effects (such as toxicity, irritation and allergy), i.e., a substance with reasonable benefit/risk ratio. "Pharmaceutically acceptable carrier" means a carrier for administration and may include various excipients and diluents and the like. Such carriers may include, but are not limited to, water, normal saline, liposomes, lipids, proteins, protein-antibody conjugates, peptides, cellulose, nanogel, buffer, glucose, glycerol, ethanol, and combinations thereof. The choice of carrier should generally be compatible with the mode of administration, as is well known to a person skilled in the art.

The effective amount of the disclosure may vary depending on the mode of administration and the severity of the disease to be treated. The preferred effective amount can be determined by a person skilled in the art based on various factors (e.g., through clinical trials). Such factors include, but are not limited to: the pharmacokinetic parameters of the active ingredient such as bioavailability, metabolism, half-life, etc.; the severity of the disease of the patient to be treated, the body weight of the patient, the immunological status of the patient, administration route and so on.

Treatment Method

The disclosure also provides a method for treating a cell proliferative disorder, comprising administering to a patient, orally or non-orally, an effective amount of the compounds of structural formulas I-V and VIII, or their respective tautomer, mesomer, racemate, enantiomer, diastereomer, deuterated compound, prodrug, or mixture thereof; or pharmaceutically acceptable salts or solvates of the compounds of formulas I-V and VIII or their respective tautomer, mesomer, racemate, enantiomer, diastereomer, deuterated compound, prodrug or mixture thereof, or the aforementioned pharmaceutical composition.

The oral or non-oral routes can be gastrointestinal administration, nasal administration, intratracheal administration, intrapulmonary administration, administration through veins or epidermis at non-lesional sites, intradermal administration, subcutaneous administration, intracardiac administration, intramuscular administration, intraosseous administration, intraperitoneal administration, epidural administration, buccal administration, sublingual administration, ophthalmic administration, rectal administration, vaginal administration, urethral administration, ear canal administration and other ways. Preferred modes of administration include oral administration, respiratory tract administration, injection, transdermal administration, mucosal administration, or cavitary administration.

Wherein, oral administration includes swallowing, sublingual and the like. The respiratory tract administration mode includes inhalation, such as ultrasonic atomizing inhalation, oxygen atomizing aerosol inhalation, manual press atomizing inhalation and the like. The administration mode of injection includes arterial injection, intravenous injection, intramuscular injection, intracardiac injection, intradermal injection and the like. The transdermal administration methods include iontophoresis, electroporation and the like. The mucosal administration mode includes nasal mucosal administration, oral mucosal administration, ophthalmic mucosal administration, rectal mucosal administration, uterine mucosal administration and vaginal mucosal administration. The cavitary administration mode includes rectal administration, vaginal administration, urethral administration, nasal administration, and ear canal administration.

All references mentioned in this disclosure (including patent documents or non-patent documents) are incorporated herein by reference as if each was individually incorporated by reference.

Although the embodiments have been described with a certain degree, apparently suitable changes of various conditions may be made without departing from the spirit and scope of the invention. It can be understood that the invention is not limited to the described embodiments, but defined by the scope of the claims, which includes equivalents of each described element.

What is claimed is:

1. A compound of structural formula I,

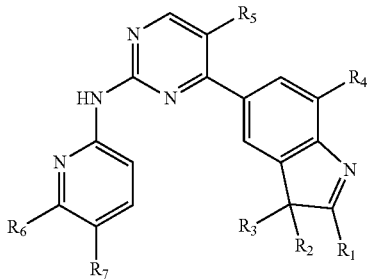

wherein $R_1$, $R_2$ and $R_3$ are each independently selected from a hydrogen atom, an unsubstituted $C_1$-$C_6$ hydrocarbon group, or a $C_1$-$C_6$ hydrocarbon group substituted by one or more substituents selected from a $C_1$-$C_6$ hydrocarbon group, $C_3$-$C_6$ cycloalkane, $C_1$-$C_6$ haloalkyl, $C_1$-$C_6$ alkoxy, hydroxyl, halogen, cyano, —$NR_8R_9$,

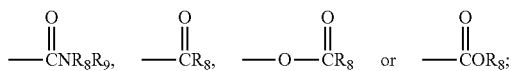

or any two of $R_1$, $R_2$ and $R_3$, together with the C atoms to which they are attached respectively, form a saturated or unsaturated 3- to 7-membered ring;

$R_4$ and $R_5$ are each independently selected from the group consisting of hydrogen and halogen, and at least one of $R_4$ and $R_5$ is halogen;

$R_6$ is selected from a hydrogen atom, $C_1$-$C_6$ alkyl, $C_1$-$C_6$ alkoxy, hydroxyl or halogen;

$R_7$ is

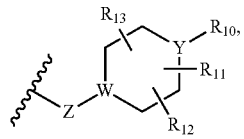

wherein Z is carbonyl, O, S, imino, sulfonyl or

and n is an integer from 0 to 4; W and Y are each independently C, N, O or S, but W and Y cannot both be C at the same time, and when Z is O or S, W is C;

$R_{10}$, $R_{11}$, $R_{12}$ and $R_{13}$ are each independently selected from a hydrogen atom, $C_1$-$C_6$ alkyl, $C_3$-$C_6$ cycloalkyl, $C_1$-$C_6$ hydroxyalkyl, $C_1$-$C_6$ haloalkyl, $C_1$-$C_6$ alkoxy, hydroxyl, halogen, cyano, —$NR_8R_9$,

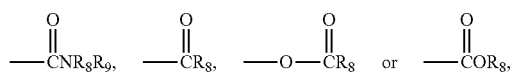

and when Y=N, $R_{10}$ cannot be $NH_2$, —$NHR_8$, —$NR_8R_9$,

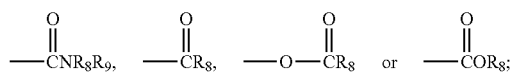

or $R_6$ and $R_7$ together with the C atoms to which they are attached form a 5- to 7-membered heterocycle containing one or more atoms selected from N, O or S, and the 5- to 7-membered heterocycle is substituted by one or more substituents selected from $C_1$-$C_6$ alkyl, $C_3$-$C_6$ cycloalkyl, $C_1$-$C_6$ haloalkyl, $C_1$-$C_6$ alkoxy, $C_1$-$C_6$ hydroxyalkyl, hydroxyl, halogen, cyano, —$NH_2$, —$NHR_8$, —$NR_8R_9$,

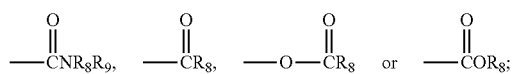

wherein $R_8$ and $R_9$ are each independently selected from the group consisting of a hydrogen atom, $C_1$-$C_6$ alkyl and $C_1$-$C_6$ hydroxyalkyl;

or a tautomer, a mesomer, a racemate, an enantiomer, a diastereomer, or a mixture thereof or pharmaceutically acceptable salts or solvates of the compound of structural formula I or its tautomer, mesomer, racemate, enantiomer, diastereomer or a mixture thereof.

2. The compound according to claim 1, wherein $R_1$, $R_2$ and $R_3$ are each independently selected from a hydrogen atom, an unsubstituted $C_1$-$C_6$ hydrocarbon group, or a $C_1$-$C_6$ hydrocarbon group substituted by one or more substituents selected from a $C_1$-$C_6$ hydrocarbon group, $C_3$-$C_6$ cycloalkyl, $C_1$-$C_6$ haloalkyl, $C_1$-$C_6$ alkoxy, hydroxyl, or halogen.

3. The compound according to claim 1, wherein $R_2$ and $R_3$, together with the C atoms to which they are both attached, form a saturated or unsaturated 3- to 7-membered ring.

4. The compound according to claim 1, wherein $R_4$ and $R_5$ are each independently selected from hydrogen, fluorine or chlorine, and at least one of $R_4$ and $R_5$ is fluorine or chlorine.

5. The compound according to claim 1, wherein $R_6$ is selected from a hydrogen atom or $C_1$-$C_6$ alkyl.

6. The compound according to claim 1, wherein Z is a carbonyl group, O or

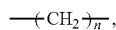

and n is an integer from 0 to 4;
wherein W and Y are each independently selected from C or N, but W and Y cannot both be C at the same time; and
wherein $R_{10}$, $R_{11}$, $R_{12}$ and $R_{13}$ are each independently selected from a hydrogen atom, $C_1$-$C_6$ alkyl, $C_3$-$C_6$ cycloalkyl, $C_1$-$C_6$ hydroxyalkyl, $C_1$-$C_6$ haloalkyl, $C_1$-$C_6$ alkoxy, hydroxyl, or —$NR_8R_9$, and when Y=N, $R_{10}$ cannot be —$NR_8R_9$.

7. The compound according to claim 1, wherein $R_7$ is selected from the substituents of the following structures:

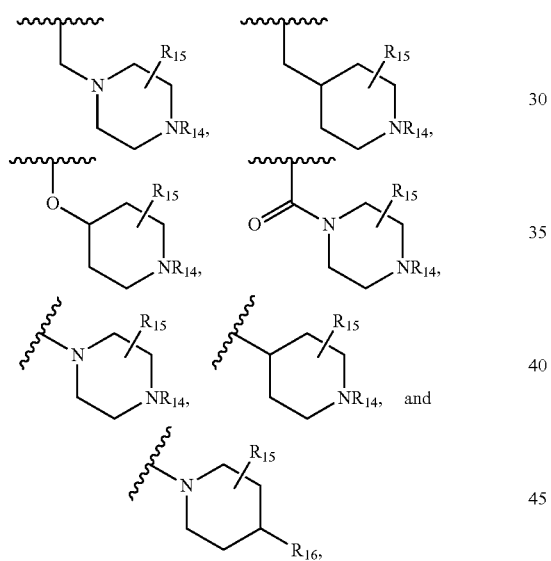

wherein $R_{14}$ and $R_{15}$ are each independently selected from a hydrogen atom, $C_1$-$C_6$ alkyl, $C_3$-$C_6$ cycloalkyl, $C_1$-$C_6$ haloalkyl, $C_1$-$C_6$ hydroxyalkyl, $C_1$-$C_6$ alkoxy or hydroxyl; Rib is selected from a hydrogen atom, $C_3$-$C_6$ cycloalkyl, $C_1$-$C_6$ haloalkyl, $C_1$-$C_6$ hydroxyalkyl, $C_1$-$C_6$ alkoxy, hydroxyl, or —$NR_8R_9$;
$R_{16}$ is selected from a hydrogen atom, $C_1$-$C_6$ alkyl, $C_3$-$C_6$ cycloalkyl, $C_1$-$C_6$ hydroxyalkyl or —$NR_8R_9$; and
$R_8$ and $R_9$ are independently selected from a hydrogen atom and $C_1$-$C_4$ alkyl.

8. The compound according to claim 1, wherein $R_6$ and $R_7$ together with the C atoms to which they are attached form a 6-membered heterocycle containing one or more atoms selected from N, O or S.

9. The compound according to claim 1, wherein the compound is represented by structural formula II, III, IV or V,

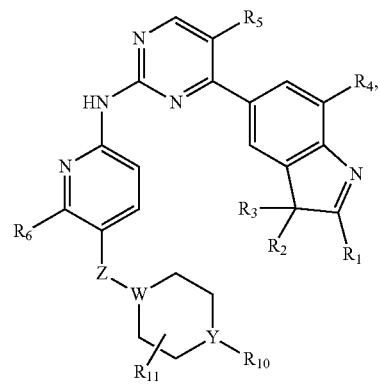

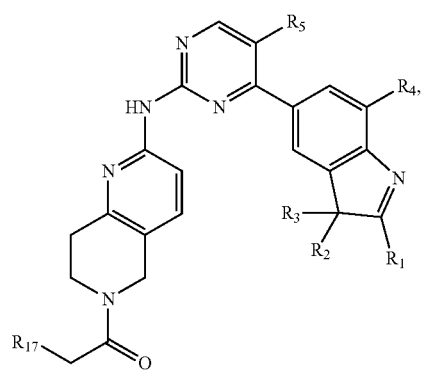

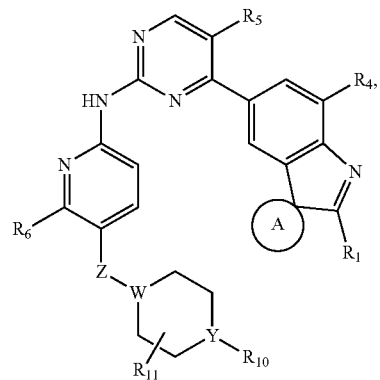

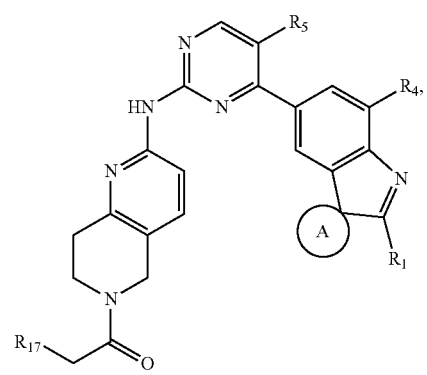

wherein $R_{17}$ is selected from hydroxyl or $C_1$-$C_3$ alkoxy; and ring A is a saturated 3- to 7-membered ring.

10. The compound according to claim 1, wherein the compound is represented by structural formula VIII,

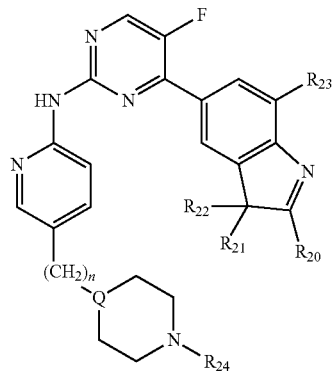

VIII wherein $R_{20}$, $R_{21}$, $R_{22}$ are each independently selected from $C_1$-$C_4$ alkyl, or $R_{20}$ is $C_1$-$C_4$ alkyl, and $R_{21}$ and $R_{22}$ together with the C atom to which they are attached form a saturated 5- to 6-membered ring;

$R_{23}$ is selected from hydrogen or fluorine;

n=0 or 1; and $R_{24}$ is selected from hydrogen, $C_1$-$C_4$ alkyl or $C_1$-$C_4$ hydroxyalkyl, and Q is C or N.

11. The compound according to claim 1, wherein the compound is represented by one of the following structures:

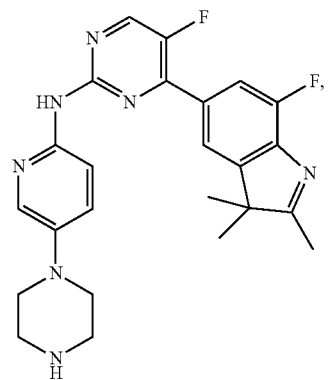

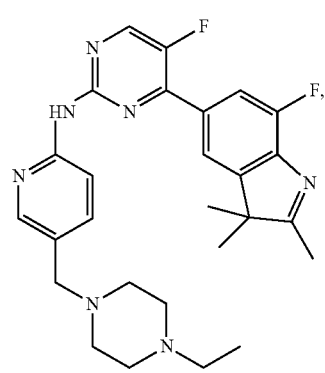

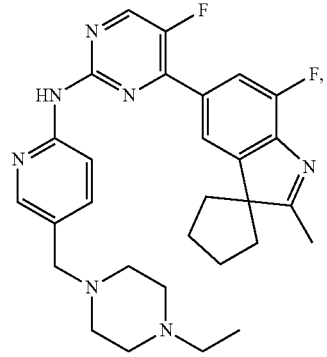

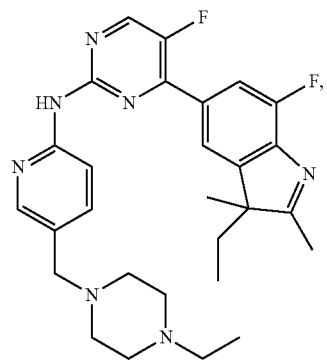

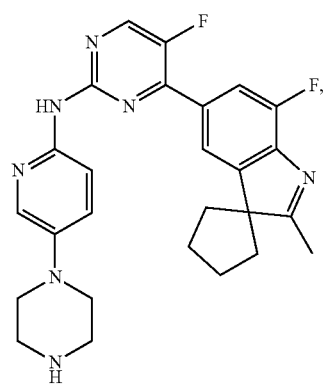

91
-continued
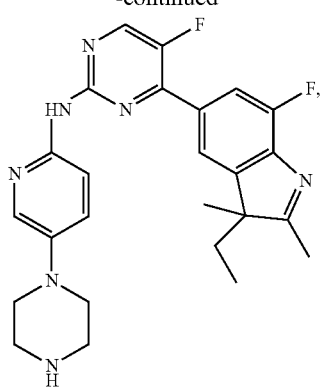
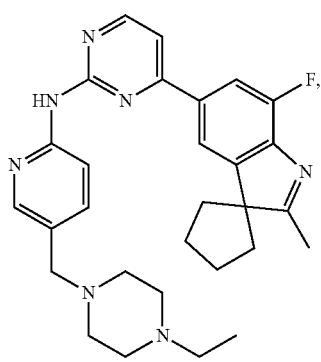
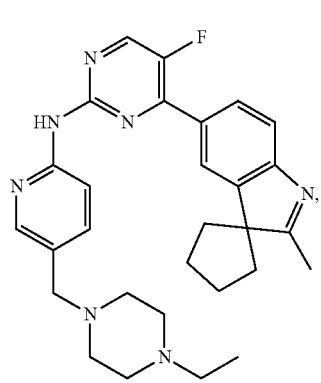
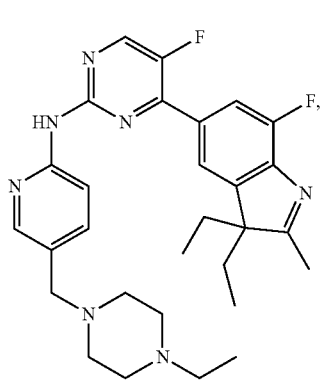
92
-continued
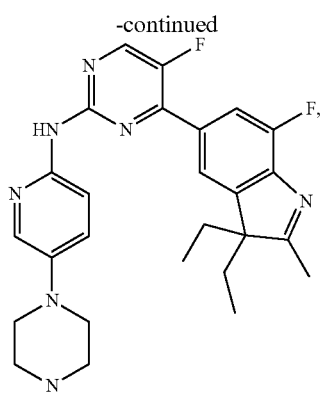
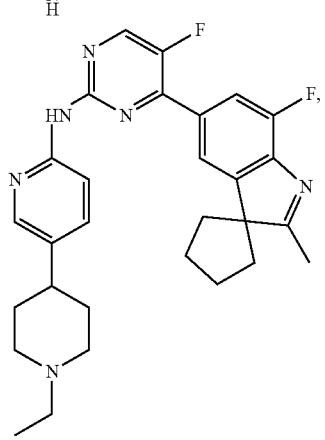
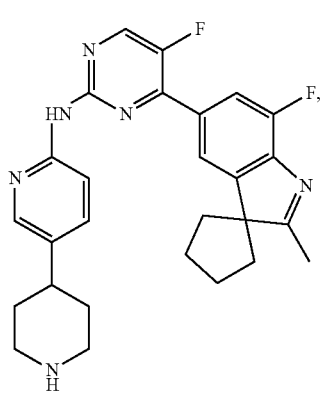
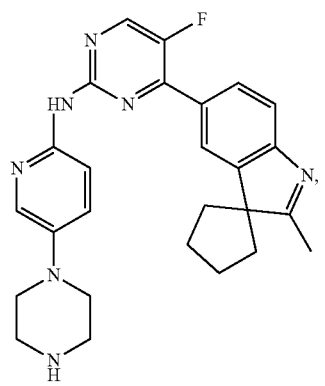

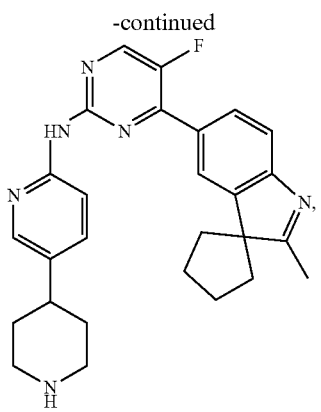
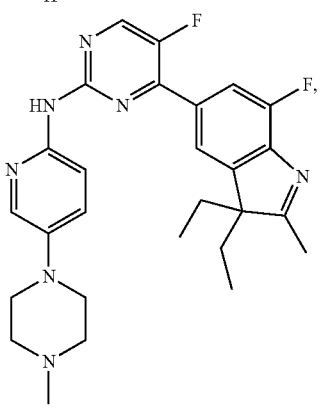
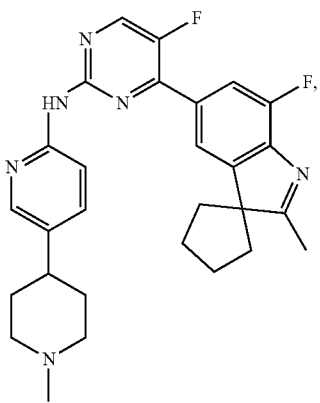
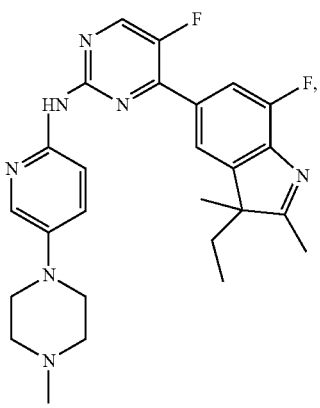
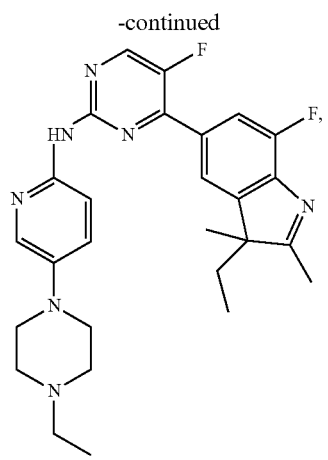
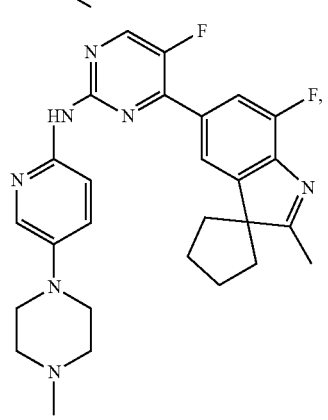
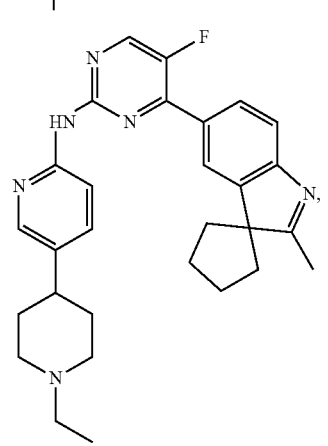
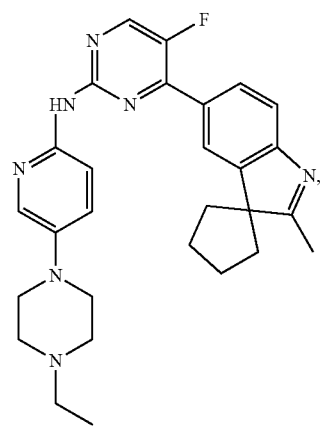

-continued
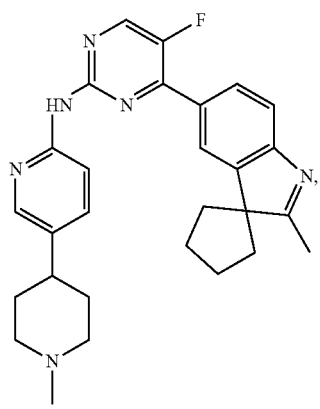
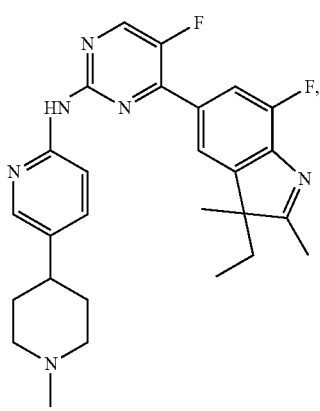
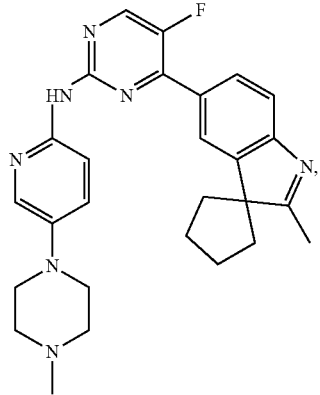
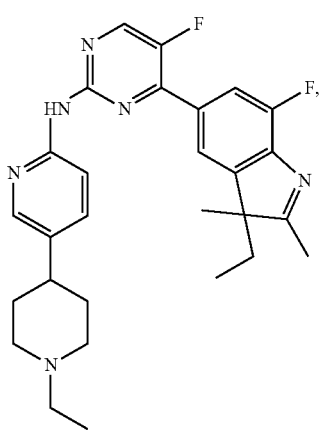
-continued
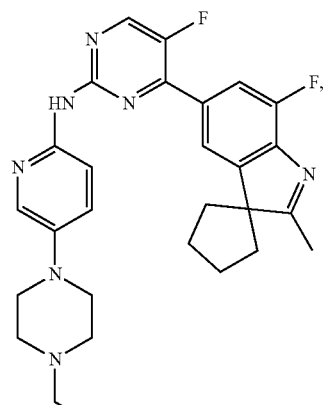
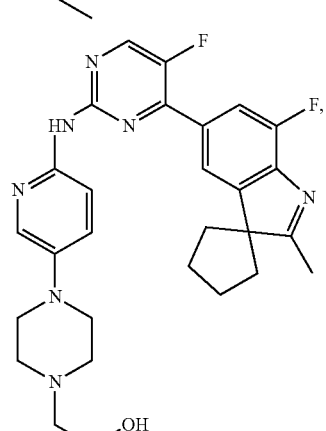
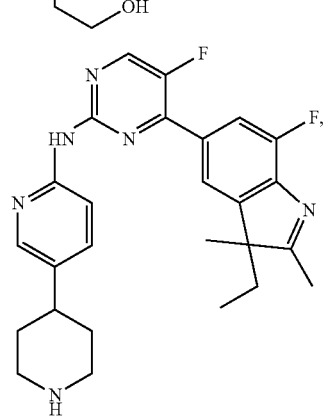
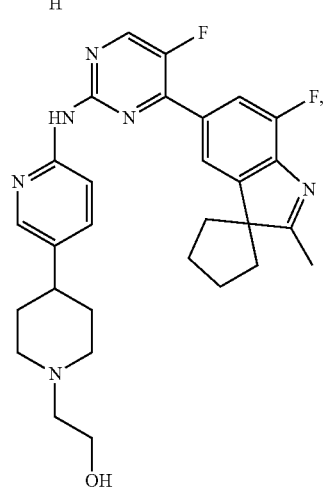

97
-continued
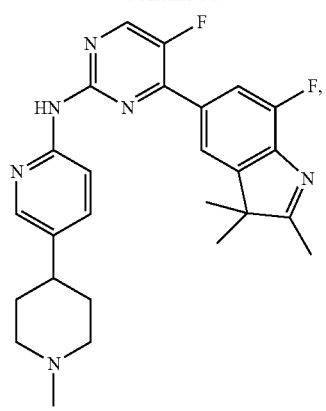
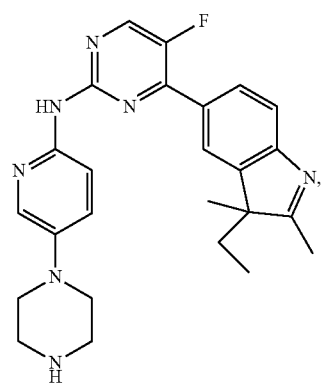
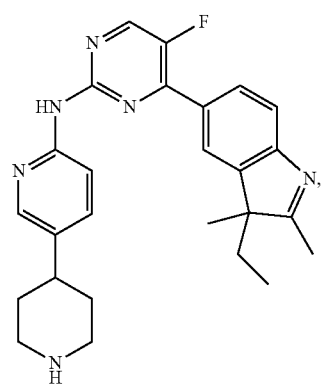
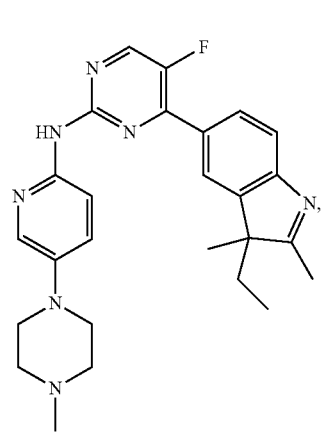
98
-continued
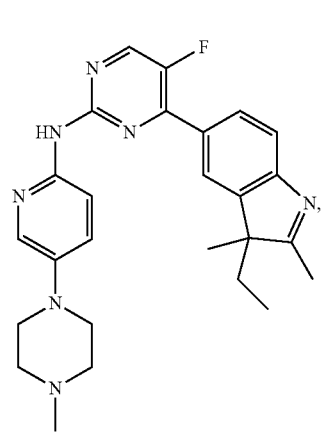
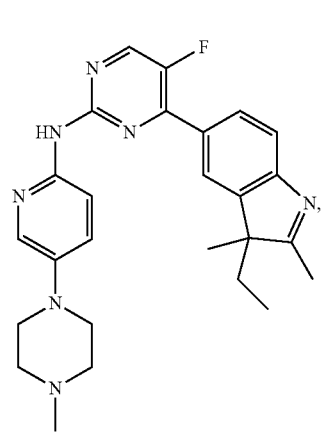
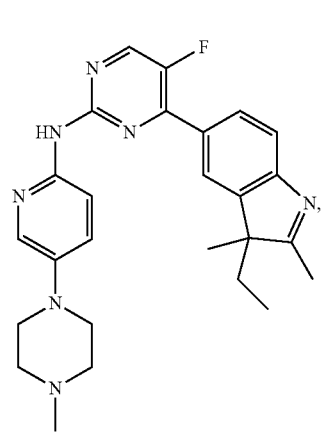
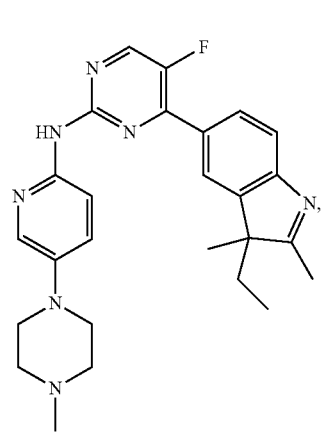

-continued
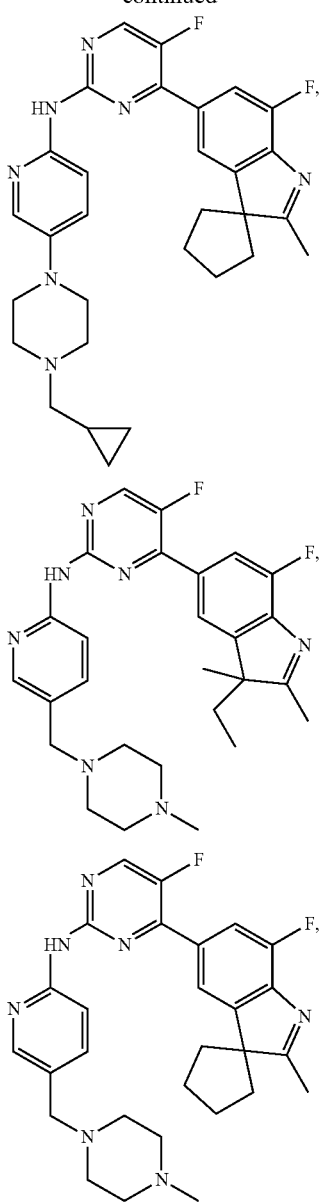
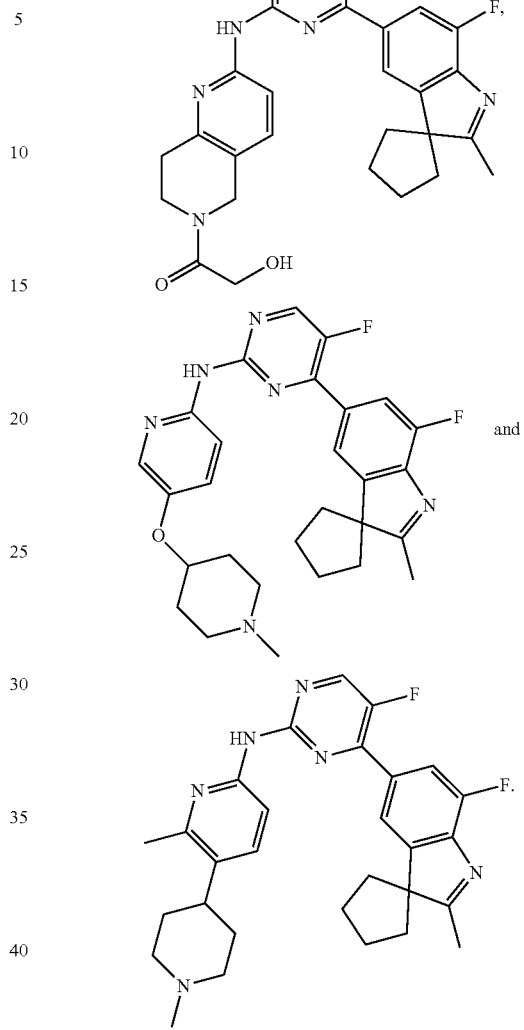
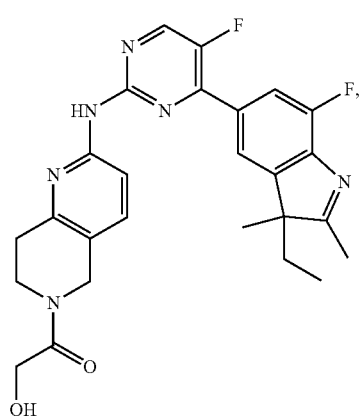
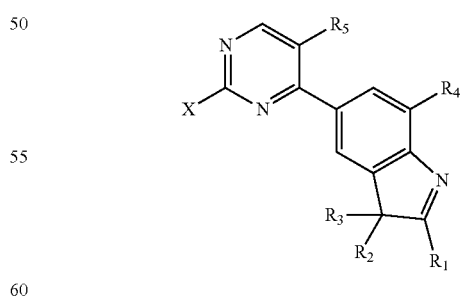
12. A compound of structural formula VI,
wherein R₁ is independently selected from a hydrogen atom, an unsubstituted $C_1$-$C_6$ hydrocarbon group, or a $C_1$-$C_6$ hydrocarbon group substituted by one or more substituents selected from a $C_1$-$C_6$ hydrocarbon group, $C_3$-$C_6$ cycloalkane, $C_1$-$C_6$ haloalkyl, $C_1$-$C_6$ alkoxy, hydroxyl, halogen, cyano, —NR₈R₉,

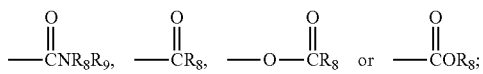

$R_2$ and $R_3$ are each independently selected from a hydrogen atom, an unsubstituted $C_1$-$C_6$ hydrocarbon group, or a $C_1$-$C_6$ hydrocarbon group substituted by one or more substituents selected from a $C_1$-$C_6$ hydrocarbon group, $C_3$-$C_6$ cycloalkane, $C_1$-$C_6$ haloalkyl, $C_1$-$C_6$ alkoxy, hydroxyl, halogen, cyano, —$NR_8R_9$,

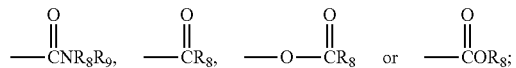

or any two of $R_1$, $R_2$ and $R_3$, together with the C atoms to which they are attached respectively, form a saturated or unsaturated 3- to 7-membered ring;

$R_4$ and $R_5$ are each independently selected from the group consisting of hydrogen and halogen, and at least one of $R_4$ and $R_5$ is halogen;

wherein $R_8$ and $R_9$ are each independently selected from the group consisting of a hydrogen atom, $C_1$-$C_6$ alkyl and $C_1$-$C_6$ hydroxyalkyl;

X is a halogen or amino group;

or a tautomer, a mesomer, a racemate, an enantiomer, a diastereomer, or a mixture thereof; or pharmaceutically acceptable salts or solvates of the compound of structural formula VI or its tautomer, mesomer, racemate, enantiomer, diastereomer, or a mixture thereof.

13. A method for preparing a compound of structural formula I, or a tautomer, a mesomer, a racemate, an enantiomer, a diastereomer, or a mixture thereof; or pharmaceutically acceptable salts or solvates of the compound of structural formula I or its tautomer, mesomer, racemate, enantiomer, diastereomer, or a mixture thereof comprising:

carrying out a palladium-catalyzed coupling reaction between a compound of formula VI and a compound of formula VII in a solvent to give a compound of structural formula I,

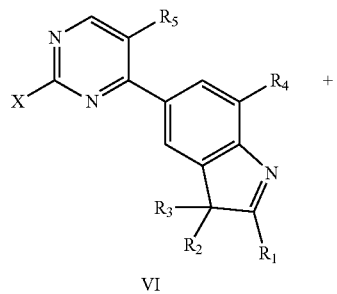

VI

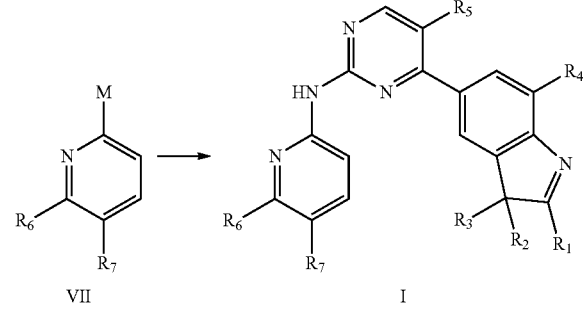

VII    I wherein $R_1$, $R_2$, and $R_3$ are each independently selected from a hydrogen atom, an unsubstituted $C_1$-$C_6$ hydrocarbon group, or a $C_1$-$C_6$ hydrocarbon group substituted by one or more substituents selected from a $C_1$-$C_6$ hydrocarbon group, $C_3$-$C_6$ cycloalkane, $C_1$-$C_6$ haloalkyl, $C_1$-$C_6$ alkoxy, hydroxyl, halogen, cyano, —$NR_8R_9$,

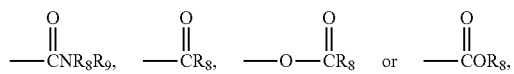

or any two of $R_1$, $R_2$ and $R_3$, together with the C atoms to which they are attached respectively, form a saturated or unsaturated 3- to 7-membered ring;

$R_4$ and $R_5$ are each independently selected from the group consisting of hydrogen and halogen, and at least one of $R_4$ and $R_5$ is halogen;

$R_6$ is selected from a hydrogen atom, $C_1$-$C_6$ alkyl, $C_1$-$C_6$ alkoxy, hydroxyl or halogen;

$R_7$ is

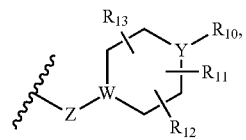

wherein Z is carbonyl, O, S, imino, sulfonyl or

and n is an integer from 0 to 4;

W and Y are each independently C, N, O or S, but W and Y cannot both be C at the same time, and when Z is O or S, W is C;

$R_{10}$, $R_{11}$, $R_{12}$ and $R_{13}$ are each independently selected from a hydrogen atom, $C_1$-$C_6$ alkyl, $C_3$-$C_6$ cycloalkyl, $C_1$-$C_6$ hydroxyalkyl, $C_1$-$C_6$ haloalkyl, $C_1$-$C_6$ alkoxy, hydroxyl, halogen, cyano, —$NR_8R_9$,

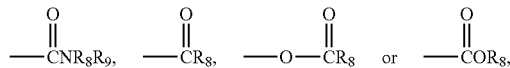

and when Y=N, $R_{10}$ cannot be $NH_2$, —$NHR_8$, —$NR_8R_9$,

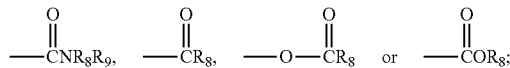

or $R_6$ and $R_7$ together with the C atoms to which they are attached form a 5- to 7-membered heterocycle containing one or more atoms selected from N, O or S, and the 5- to 7-membered heterocycle is substituted by one or more substituents selected from $C_1$-$C_6$ alkyl, $C_3$-$C_6$ cycloalkyl, $C_1$-$C_6$ haloalkyl, $C_1$-$C_6$ alkoxy, $C_1$-$C_6$ hydroxyalkyl, hydroxyl, halogen, cyano, —$NH_2$, —$NHR_8$, —$NR_8R_9$,

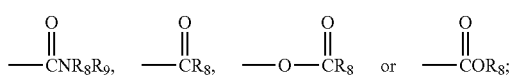

wherein $R_8$ and $R_9$ are each independently selected from the group consisting of a hydrogen atom, $C_1$-$C_6$ alkyl and $C_1$-$C_6$ hydroxyalkyl;

X and M are each independently a halogen or amino group, and only one of X and M is amino and one of the two must be amino.

14. A pharmaceutical composition comprising:

one or more compounds selected from the compounds of structural formulas I-V and VIII,

I

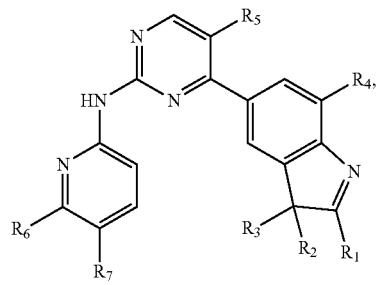

II

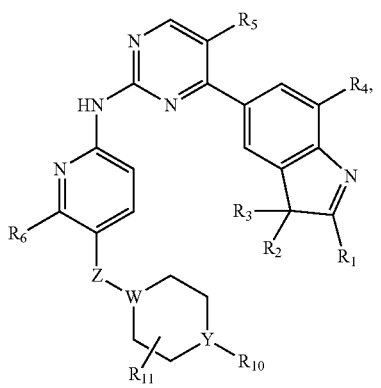

III

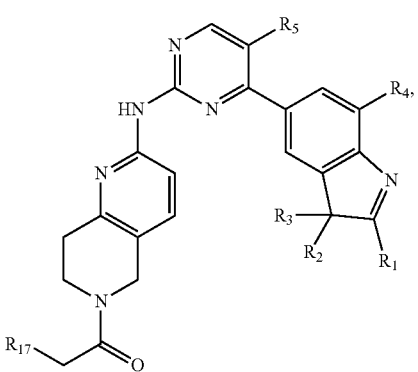

-continued

IV

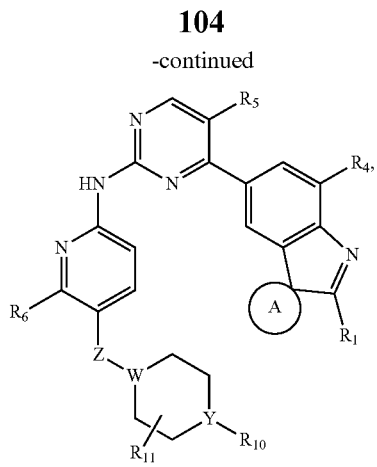

V

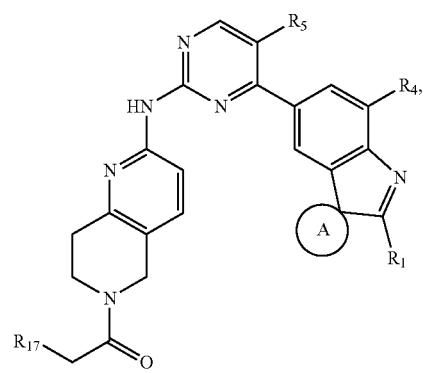

VIII

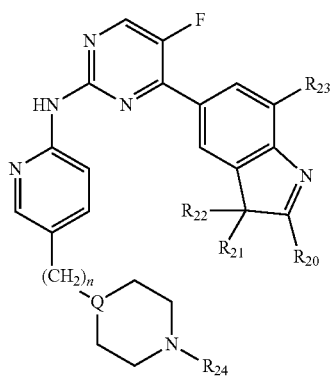

wherein $R_1$, $R_2$ and $R_3$ are each independently selected from a hydrogen atom, an unsubstituted $C_1$-$C_6$ hydrocarbon group, or a $C_1$-$C_6$ hydrocarbon group substituted by one or more substituents selected from a $C_1$-$C_6$ hydrocarbon group, $C_3$-$C_6$ cycloalkane, $C_1$-$C_6$ haloalkyl, $C_1$-$C_6$ alkoxy, hydroxyl, halogen, cyano, —$NR_8R_9$,

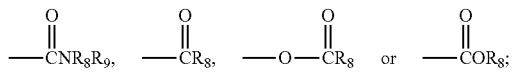

or any two of $R_1$, $R_2$ and $R_3$, together with the C atoms to which they are attached respectively, form a saturated or unsaturated 3- to 7-membered ring;

$R_4$ and $R_5$ are each independently selected from the group consisting of hydrogen and halogen, and at least one of $R_4$ and $R_5$ is halogen;

$R_6$ is selected from a hydrogen atom, $C_1$-$C_6$ alkyl, $C_1$-$C_6$ alkoxy, hydroxyl or halogen;

$R_7$ is

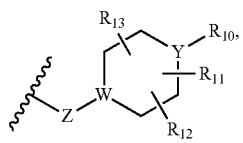

wherein Z is carbonyl, O, S, imino, sulfonyl or

and n is an integer from 0 to 4; W and Y are each independently C, N, O or S, but W and Y cannot both be C at the same time, and when Z is O or S, W is C; $R_{10}$, $R_{11}$, $R_{12}$ and $R_{13}$ are each independently selected from a hydrogen atom, $C_1$-$C_6$ alkyl, $C_3$-$C_6$ cycloalkyl, $C_1$-$C_6$ hydroxyalkyl, $C_1$-$C_6$ haloalkyl, $C_1$-$C_6$ alkoxy, hydroxyl, halogen, cyano, —$NR_8R_9$,

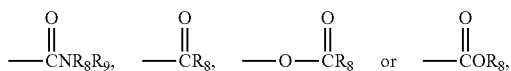

and when Y=N, $R_{10}$ cannot be $NH_2$, —$NHR_8$, —$NR_8R_9$,

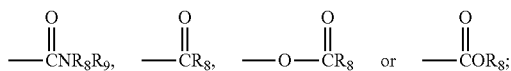

or $R_6$ and $R_7$ together with the C atoms to which they are attached form a 5- to 7-membered heterocycle containing one or more atoms selected from N, O or S, and the 5- to 7-membered heterocycle is substituted by one or more substituents selected from $C_1$-$C_6$ alkyl, $C_3$-$C_6$ cycloalkyl, $C_1$-$C_6$ haloalkyl, $C_1$-$C_6$ alkoxy, $C_1$-$C_6$ hydroxyalkyl, hydroxyl, halogen, cyano, —$NH_2$, —$NHR_8$, —$NR_8R_9$,

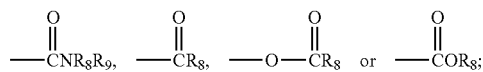

wherein $R_8$ and $R_9$ are each independently selected from the group consisting of a hydrogen atom, $C_1$-$C_6$ alkyl and $C_1$-$C_6$ hydroxyalkyl;

wherein $R_{17}$ is selected from hydroxyl or $C_1$-$C_3$ alkoxy; ring A is a saturated 3- to 7-membered ring;

wherein $R_{20}$, $R_{21}$, $R_{22}$ are each independently selected from $C_1$-$C_4$ alkyl, or $R_{20}$ is $C_1$-$C_4$ alkyl, and $R_{21}$ and $R_{22}$ together with the C atom to which they are attached form a saturated 5- to 6-membered ring;

$R_{23}$ is selected from hydrogen or fluorine;

n=0 or 1;

$R_{24}$ is selected from hydrogen, $C_1$-$C_4$ alkyl or $C_1$-$C_4$ hydroxyalkyl, and Q is C or N;

or their respective tautomer, mesomer, racemate, enantiomer, diastereomer, or a mixture thereof; or pharmaceutically acceptable salts or solvates of the compounds of formulas I-V and VIII or their respective tautomer, mesomer, racemate, enantiomer, diastereomer, or a mixture thereof; and a pharmaceutically acceptable carrier.

15. A method for treating a cell proliferative disorder, comprising:

administering to a subject in need thereof, orally or parenterally, an effective amount of one or more compounds of structural formulas I-V and VIII, or their respective tautomer, mesomer, racemate, enantiomer, diastereomer, or a mixture thereof; or pharmaceutically acceptable salts or solvates of the one or more compounds of formulas I-V and VIII or their respective tautomer, mesomer, racemate, enantiomer, diastereomer, or a mixture thereof, or a pharmaceutical composition wherein the pharmaceutical composition comprises:

a pharmaceutically acceptable carrier and one or more compounds selected from the compounds of structural formulas I-V and VIII, or their respective tautomer, mesomer, racemate, enantiomer, diastereomer, or a mixture thereof; or pharmaceutically acceptable salts or solvates of the one or more compounds of formulas I-V and VIII or their respective tautomer, mesomer, racemate, enantiomer, diastereomer, or a mixture thereof;

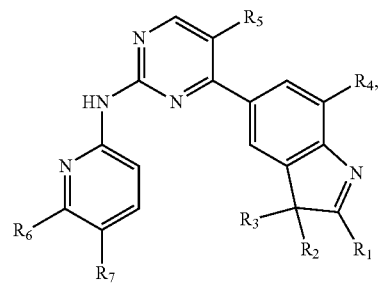

I

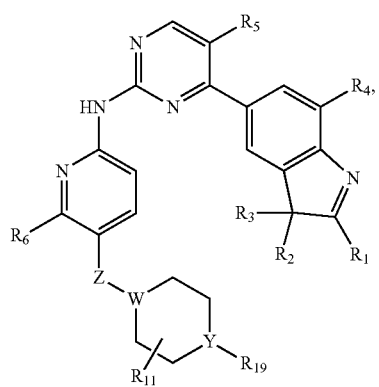

II

-continued

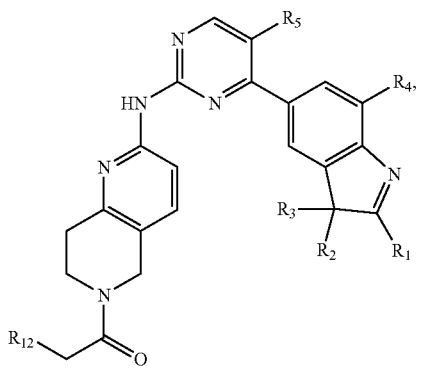

III

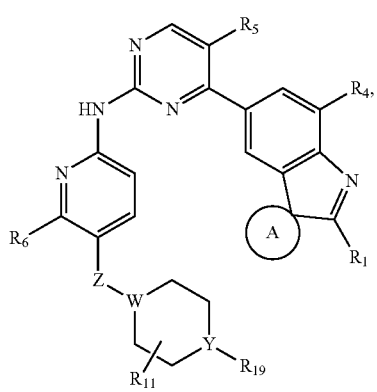

IV

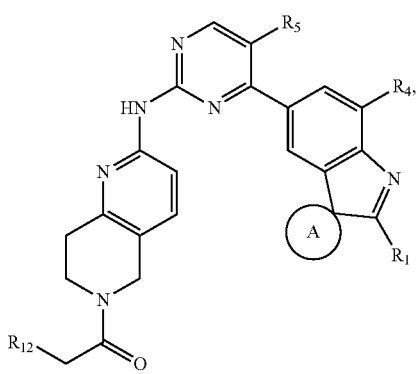

V

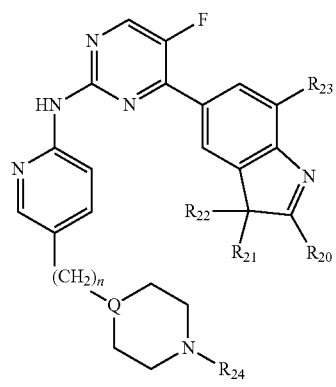

VIII wherein $R_1$, $R_2$ and $R_3$ are each independently selected from a hydrogen atom, an unsubstituted $C_1$-$C_6$ hydrocarbon group, or a $C_1$-$C_6$ hydrocarbon group substituted by one or more substituents selected from a $C_1$-$C_6$ hydrocarbon group, $C_3$-$C_6$ cycloalkane, $C_1$-$C_6$ haloalkyl, $C_1$-$C_6$ alkoxy, hydroxyl, halogen, cyano, —$NR_8R_9$,

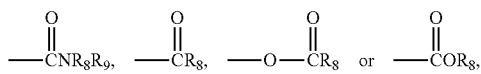

or any two of $R_1$, $R_2$ and $R_3$, together with the C atoms to which they are attached respectively, form a saturated or unsaturated 3- to 7-membered ring;

$R_4$ and $R_5$ are each independently selected from the group consisting of hydrogen and halogen, and at least one of $R_4$ and $R_5$ is halogen;

$R_6$ is selected from a hydrogen atom, $C_1$-$C_6$ alkyl, $C_1$-$C_6$ alkoxy, hydroxyl or halogen;

$R_7$ is wherein Z is carbonyl, O, S, imino, sulfonyl or $$-(CH_2)_n-,$$

and n is an integer from 0 to 4; W and Y are each independently C, N, O or S, but W and Y cannot both be C at the same time, and when Z is O or S, W is C; $R_{10}$, $R_{11}$, $R_{12}$ and $R_{13}$ are each independently selected from a hydrogen atom, $C_1$-$C_6$ alkyl, $C_3$-$C_6$ cycloalkyl, $C_1$-$C_6$ hydroxyalkyl, $C_1$-$C_6$ haloalkyl, $C_1$-$C_6$ alkoxy, hydroxyl, halogen, cyano, —$NR_8R_9$,

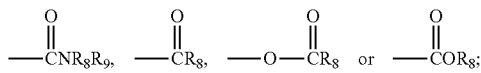

and when Y=N, $R_{10}$ cannot be $NH_2$, —$NHR_8$, —$NR_8R_9$,

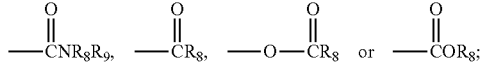

or $R_6$ and $R_7$ together with the C atoms to which they are attached form a 5- to 7-membered heterocycle containing one or more atoms selected from N, O or S, and the 5- to 7-membered heterocycle is substituted by one or more substituents selected from $C_1$-$C_6$ alkyl, $C_3$-$C_6$ cycloalkyl, $C_1$-$C_6$ haloalkyl, $C_1$-$C_6$ alkoxy, $C_1$-$C_6$ hydroxyalkyl, hydroxyl, halogen, cyano, —$NH_2$, —$NHR_8$, —$NR_8R_9$,

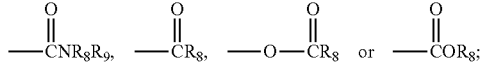

wherein $R_8$ and $R_9$ are each independently selected from the group consisting of a hydrogen atom, $C_1$-$C_6$ alkyl and $C_1$-$C_6$ hydroxyalkyl;

wherein $R_{17}$ is selected from hydroxyl or $C_1$-$C_3$ alkoxy;

ring A is a saturated 3- to 7-membered ring;

wherein $R_{20}$, $R_{21}$, $R_{22}$ are each independently selected from $C_1$-$C_4$ alkyl, or $R_{20}$ is $C_1$-$C_4$ alkyl, and $R_{21}$ and $R_{22}$ together with the C atom to which they are attached form a saturated 5- to 6-membered ring;

$R_{23}$ is selected from hydrogen or fluorine;

n=0 or 1;

$R_{24}$ is selected from hydrogen, $C_1$-$C_4$ alkyl or $C_1$-$C_4$ hydroxyalkyl, and Q is C or N;

wherein the cell proliferative disorder is glioma or breast cancer; and/or wherein the compounds of structural formulas I-V and VIII, or their respective tautomer, mesomer, racemate, enantiomer, diastereomer, or a mixture thereof; or pharmaceutically acceptable salts or solvates of the compounds of formulas I-V and VIII or their respective tautomer, mesomer, racemate, enantiomer, diastereomer, or mixture are administered to the subject in need thereof as the sole active ingredient or in combination with other biologically active substances, the other biologically active substances comprising anticancer agents, immunosuppressive agents and antiviral agents, wherein the anticancer agent is one or more agents selected from cyclophosphamide, ifosfamide, thiotepa, semustine, mechlorethamine hydrochloride, busulfan, chlorambucil, melphalan, nitrocaphane, formylmelphalan, carmustine, lomustine, altretamine, dibromomannitol, cytarabine, fluorouracil, methotrexate, hydroxyurea, tegafur, meisoindigo, mercaptopurine, cisplatin, carboplatin, oxaliplatin, actinomycin D, mitomycin, doxorubicin, pingyangmycin, epirubicin, pirarubicin, daunorubicin, bleomycin, homoharringtonine and its derivatives, vincristine and its derivatives, hydroxycamptothecin and its derivatives, etoposide and its derivatives, vindesine and its derivatives, vinblastine and its derivatives, vinorelbine bitartrate, taxol and its derivatives, colchicine and its derivatives, elemene and its derivatives, aminoglutethimide, tamoxifen, dexamethasone, dutasteride, flutamide, gonadorelin, leuprolide acetate, letrozole, sunitinib, sorafenib, imatinib, gefitinib, erlotinib, vandetanib, pazopanib, lapatinib, canertinib, afatinib, mubritinib, dasatinib, neratinib, temozolomide, trastuzumab, pertuzumab, rituximab, panitumumab, bevacizumab, ipilimumab, ofatumumab, ramucirumab, everolimus, sirolimus and zotarolimus.

16. The compound according to claim 2, wherein $R_1$, $R_2$ and $R_3$ are each independently selected from a hydrogen atom, unsubstituted linear or branched $C_1$-$C_6$ alkyl, or unsubstituted linear or branched $C_2$-$C_4$ alkenyl.

17. The compound according to claim 16, wherein $R_1$, $R_2$ and $R_3$ are each independently selected from a hydrogen atom, unsubstituted linear or branched $C_1$-$C_4$ alkyl.

18. The compound according to claim 6, wherein Z is

and n is an integer from 0 to 2.

19. The compound according to claim 18, wherein n=0 or 1.

20. The compound according to claim 7, wherein $R_8$ and $R_9$ are independently selected from hydrogen atom and $C_1$-$C_4$ alkyl.

21. The compound according to claim 8, wherein $R_6$ and $R_7$ together with the C atoms to which they are attached form the following chemical structure:

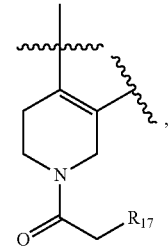

wherein $R_{17}$ is selected from hydroxyl or $C_1$-$C_3$ alkoxy.

22. The compound according to claim 9, wherein ring A is a saturated 3- to 6-membered ring.

23. The compound according to claim 12, wherein X halogen.

24. The compound according to claim 23, wherein X is fluorine, bromine or chlorine.

25. The method according to claim 13, wherein one of X and M is halogen.

26. The method according to claim 25, wherein one of X and M is fluorine, bromine or chlorine.

27. The pharmaceutical composition according to claim 14, wherein ring A is a saturated 3- to 6-membered ring.

28. A kit, comprising:
the pharmaceutical composition defined in claim 14; and instructions for the operation of the kit.

29. The method according to claim 15, wherein ring A is a saturated 3- to 6-membered ring.

* * * * *